US012404542B2

(12) United States Patent
Shao et al.

(10) Patent No.: US 12,404,542 B2
(45) Date of Patent: Sep. 2, 2025

(54) VISUAL AND MODULAR DETECTION OF NUCLEIC ACIDS WITH ENZYME-ASSISTED NANOTECHNOLOGY

(71) Applicants: National University of Singapore, Singapore (SG); Agency for Science, Technology and Research, Singapore (SG)

(72) Inventors: Huilin Shao, Singapore (SG); Nicholas Rui Yuan Ho, Singapore (SG)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 1279 days.

(21) Appl. No.: 17/257,479

(22) PCT Filed: Jul. 2, 2019

(86) PCT No.: PCT/SG2019/050328
§ 371 (c)(1),
(2) Date: Dec. 31, 2020

(87) PCT Pub. No.: WO2020/009660
PCT Pub. Date: Jan. 9, 2020

(65) Prior Publication Data
US 2021/0130870 A1 May 6, 2021

(30) Foreign Application Priority Data
Jul. 3, 2018 (SG) .............................. 10201805745P

(51) Int. Cl.
*C12Q 1/68* (2018.01)
*C12M 3/00* (2006.01)
(Continued)

(52) U.S. Cl.
CPC ............. *C12Q 1/682* (2013.01); *C12M 23/16* (2013.01); *C12M 23/42* (2013.01); *C12N 15/115* (2013.01); *C12N 2310/16* (2013.01)

(58) Field of Classification Search
None
See application file for complete search history.

(56) References Cited

U.S. PATENT DOCUMENTS

2017/0335381 A1* 11/2017 Park ..................... C12Q 1/6851

OTHER PUBLICATIONS

Urmann et al. (BioNanoMat, 2017, 18(1-2):20160012, p. 1-17) (Year: 2017).*

(Continued)

*Primary Examiner* — Stephanie K Mummert
(74) *Attorney, Agent, or Firm* — Meunier Carlin & Curfman LLC

(57) ABSTRACT

The present invention provides methods and devices for specific detection of nucleic acids using an integrated circuit of two independent enzyme-DNA nanostructures—an easily adjustable recognition element and a sensitive universal signaling element—to decouple target recognition and visual signal amplification. The recognition element comprises a DNA polymerase enzyme, a DNA polymerase enzyme-specific DNA aptamer and an inverter oligonucleotide. In the presence of a target nucleic acid, the inverter oligonucleotide binds to the target nucleic acid and releases the DNA polymerase enzyme from inhibition by the DNA aptamer. The activated DNA polymerase enzyme is then contacted with a signaling nanostructure comprising a self-priming portion responsive to the DNA polymerase enzyme, in the presence of labelled dNTPs and signal development reagents, wherein the activated DNA polymerase enzyme would add the labelled dNTPs to the self-priming portion, (Continued)

followed by the binding of the signal development reagents to the labelled dNTPs.

29 Claims, 21 Drawing Sheets

Specification includes a Sequence Listing.

(51) Int. Cl.
    *C12M 3/06*     (2006.01)
    *C12N 15/115*     (2010.01)
    *C12Q 1/682*     (2018.01)

(56) References Cited

OTHER PUBLICATIONS

Cheung et al. (PNAS, 2013, 110(40):15967-15972) (Year: 2013).*
Aktas et al., "Nucleic acid sensing with enzyme-DNA binding protein conjugates cascade and simple DNA nanostructures," Anal Bioanal Chem (2017) 409(14):3623-3632.
Jauset-Rubio et al., "Ultrasensitive and rapid detection of B-conglutin combining aptamers and isothermal recombinase polymerase amplification," Anal Bioanal Chem (2016) 409(1):143-149.
Ho et al., "Visual and modular detection of pathogen nucleic acids with enzyme-DNA molecular complexes," Nat Commun (2018) 9(1):e3238.
International Search Report and Written Opinion for PCT/SG2019/050328, dated Aug. 29, 2019, 13 pages.

* cited by examiner

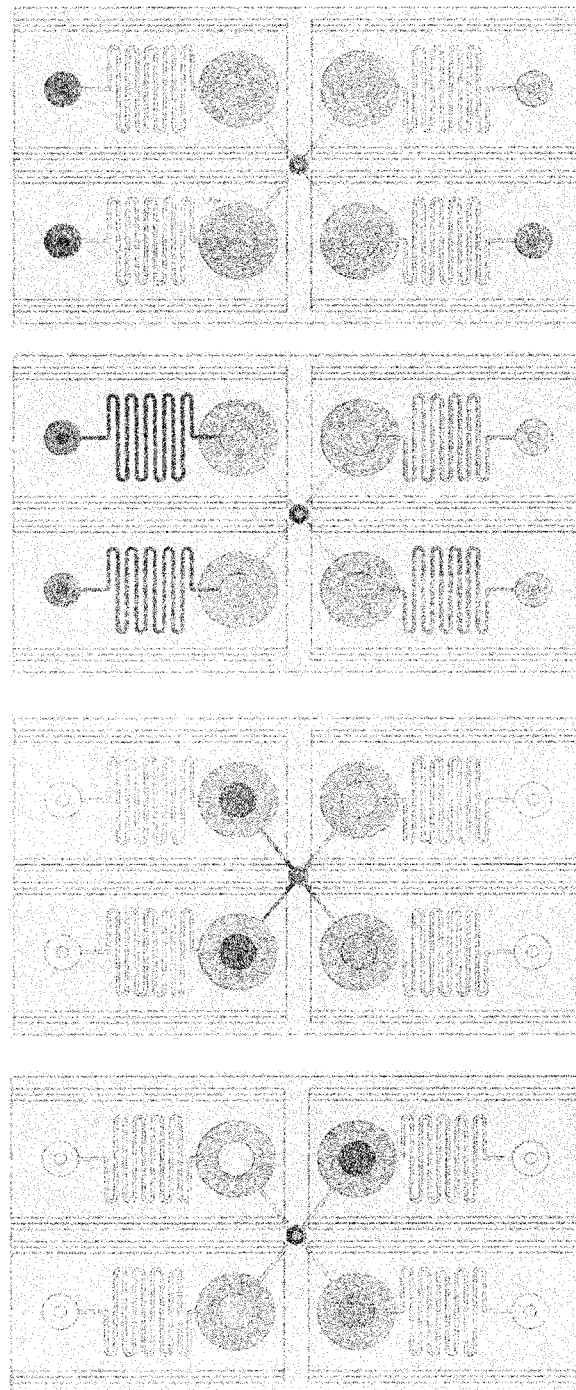

Step 1: Sample loading

Samples are added to the inlets of individual assay cassettes, each preloaded with recognition nanostructures targeting for specific DNA sequences.

Step 2: Recognition

The assay cassettes are mounted onto the common cartridge. A negative pressure is used to actuate parallel fluid flow. Diffusive mixing in the serpentine channel improves sequence recognition and activation of the inactive polymerase if target is present.

Step 3: Target-independent signal enhancement

The active polymerases are transferred into the reaction chambers, where they add HRP to the immobilized universal signaling nanostructures through biotinylated dNTPs.

Step 4: Visual detection

Unbound HRP is removed and HRP substrate is introduced uniformly into the reaction chambers. Development of the HRP substrates leads to direct visual readout.

Legend:

 Different enVision assays with unique recognition nanostructures

Figure 7

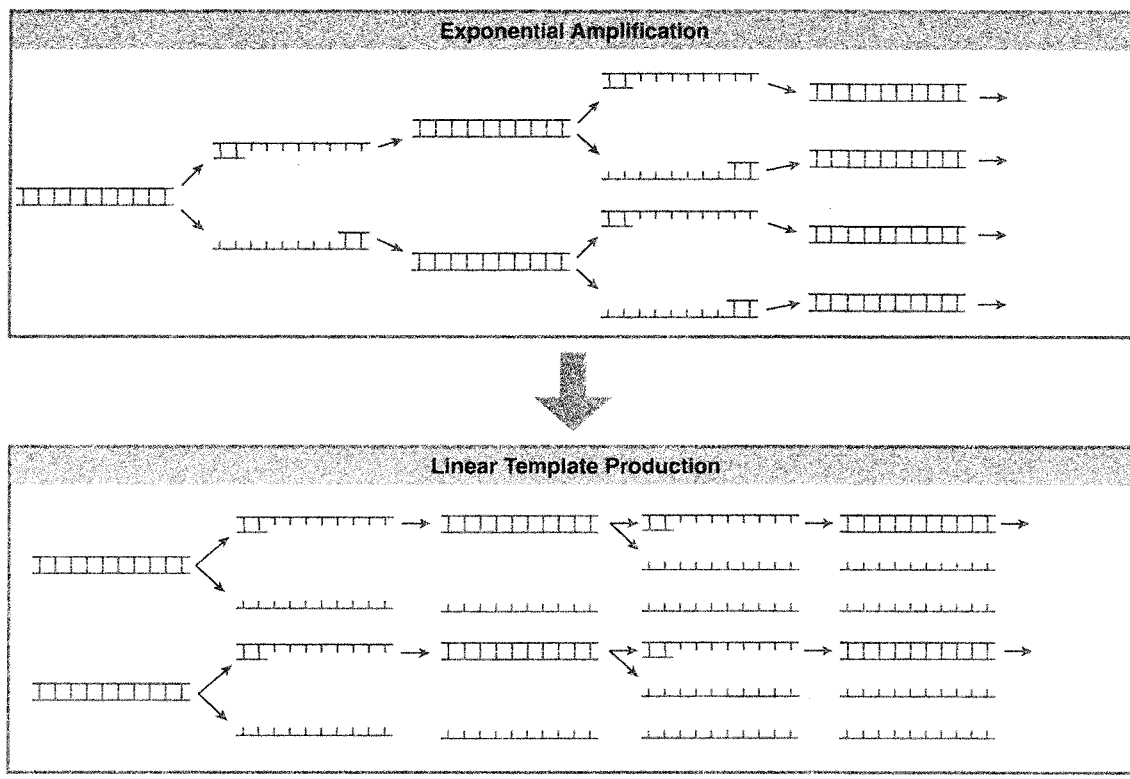
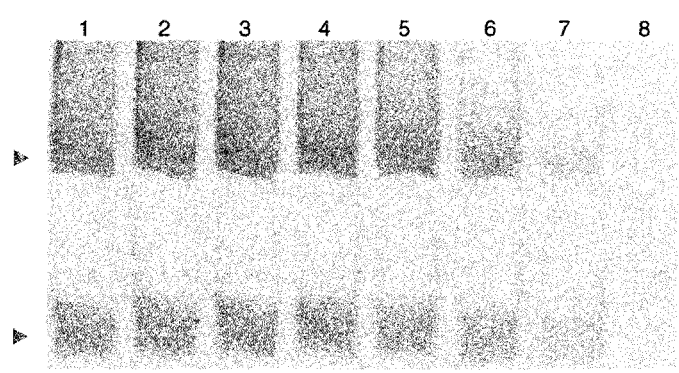
Figure 11 a
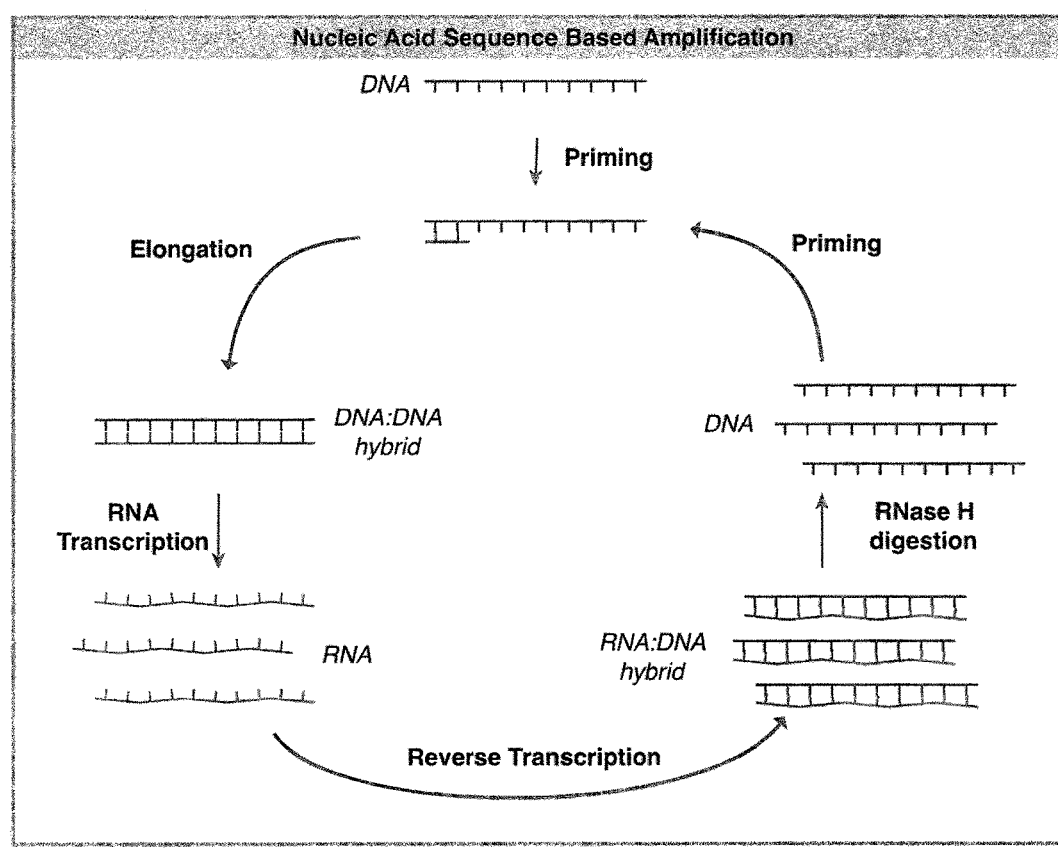
b
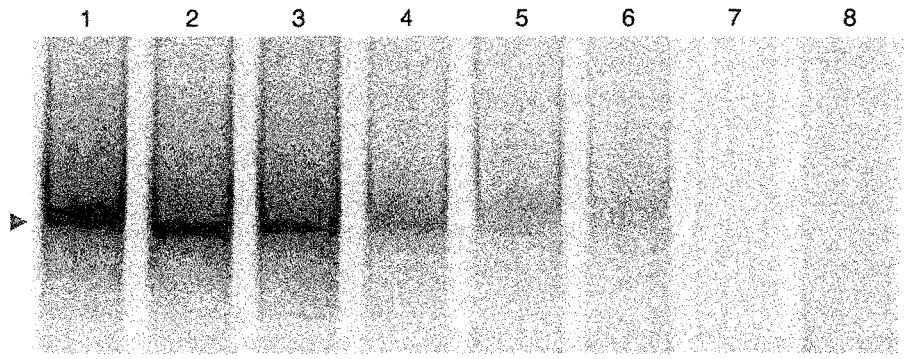
Figure 12

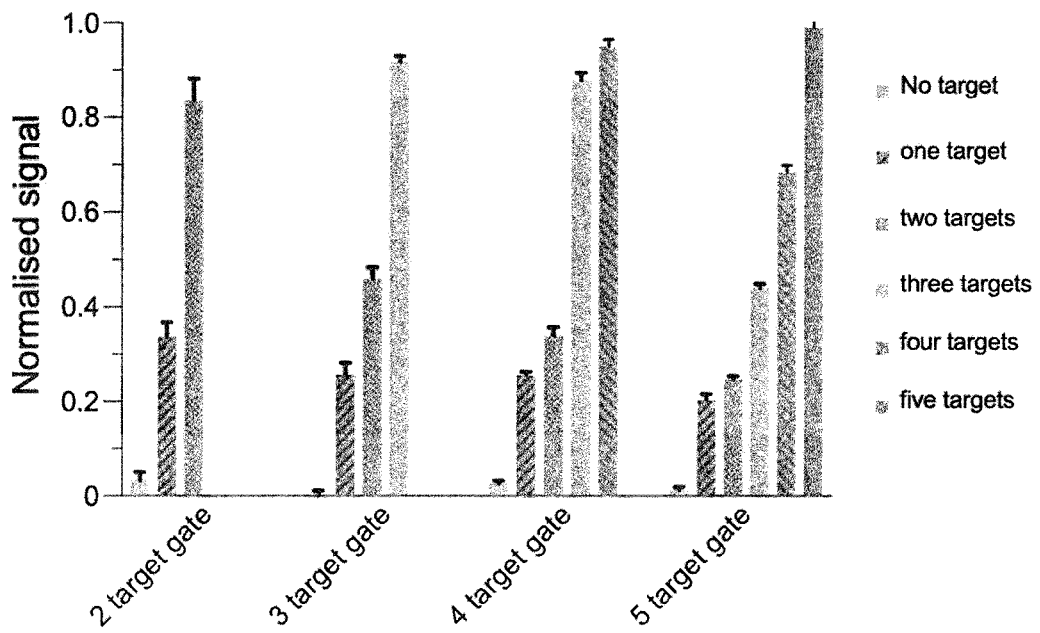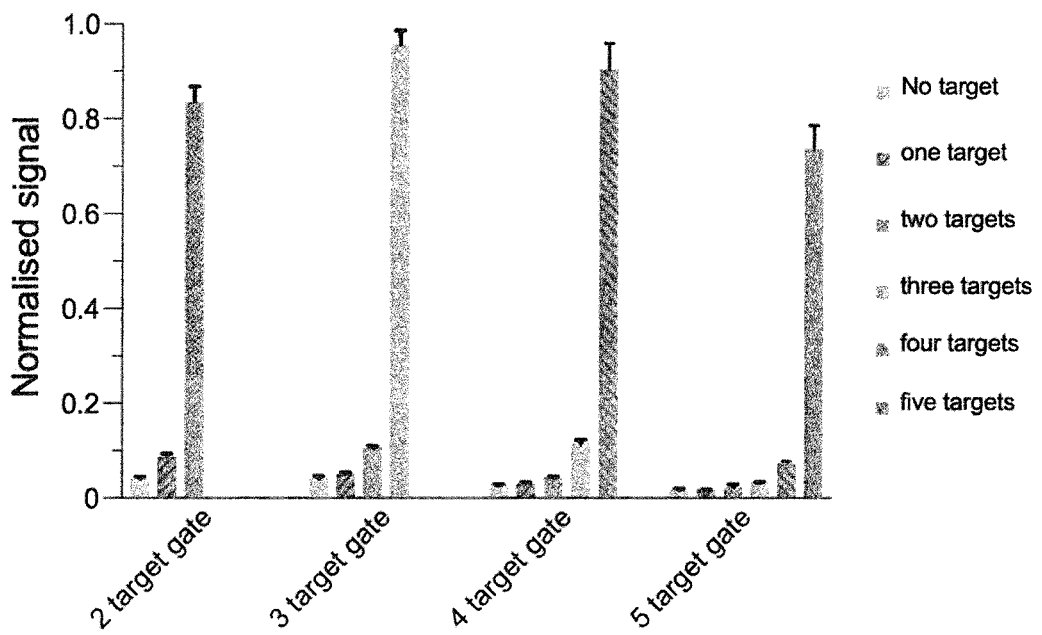
Figure 16

VISUAL AND MODULAR DETECTION OF NUCLEIC ACIDS WITH ENZYME-ASSISTED NANOTECHNOLOGY

CROSS REFERENCE TO RELATED APPLICATIONS

This application is a national stage application under 35 U.S.C. § 371 of International Application No. PCT/SG2019/050328, filed internationally on Jul. 2, 2019, which claims the benefit of priority to Singaporean Application No. SG10201805745P, filed Jul. 3, 2018, the contents of which are hereby incorporated by reference in their entirety for all purposes.

SUBMISSION OF SEQUENCE LISTING ON ASCII TEXT FILE

The present application is being filed along with a Sequence Listing in electronic format. The Sequence Listing is provided as a file entitled 255352004900SeqList.txt, created Dec. 31, 2020, which is 32,226 bytes in size. The information in the electronic format of the Sequence Listing is incorporated by reference in its entirety.

FIELD OF THE INVENTION

The present invention relates to the detection of nucleic acids using enzyme-assisted nanotechnology. More specifically, the present invention provides methods and devices for specific detection of nucleic acids using an integrated circuit of two independent enzyme-DNA nanostructures—an easily adjustable recognition element and a sensitive universal signaling element—to decouple target recognition and visual signal amplification.

BACKGROUND OF THE INVENTION

Detection of pathogen nucleic acids has broad applications in infection diagnostics and management. As an alternative to conventional pathogen culture, which entails long processing time (i.e., several days) and requires species-specific protocols (e.g., bacteria vs. viruses), nucleic acid technologies have been increasingly adopted in clinical laboratories to provide unprecedented molecular information about infections (and beyond)[Niemz, A., Ferguson, T. M. & Boyle, D. S. *Trends Biotechnol* 29: 240-250 (2011); Nong, R. Y., et al., *Expert Rev Proteomics* 9: 21-32 (2012); Zumla, A. et al. *Lancet Infect Dis* 14: 1123-1135 (2014)]. For example, nucleic acid-based human papillomavirus (HPV) testing is essential to contemporary cervical cancer testing. HPV, the most common sexually transmitted infection, is the primary cause of cervical cancer [Crosbie, E. J., et al., *Lancet* 382: 889-899 (2013)]. There are >100 subtypes of HPV, of which 15 are considered of high malignancy risk [Bouvard, V. et al. *Lancet Oncol* 10: 321-322 (2009)]. HPV infection is a global epidemic; while mostly benign, some of these infections can progress to cause deadly cervical cancer. This complex etiology, carcinogenesis and disease progression are primarily linked to two factors: 1) infection from specific HPV molecular subtypes, and 2) the persistence of infection [Bodily, J. & Laimins, L. *Trends Microbiol* 19: 33-39 (2011); Schiffman, M. et al. *Nat Rev Dis Primers* 2: 16086 (2016)].

Current detection of pathogen nucleic acids, is almost exclusively performed in large centralized clinical laboratories. This limited reach arises from the high complexity and cost associated with conventional technologies. In the case of HPV detection, commercial assays leverage primarily on polymerase chain reaction (PCR, e.g., Cobas HPV) to amplify and detect specific DNA targets [Rao, A. et al. *J Clin Microbiol* 51: 1478-1484 (2013); Cui, M. et al. *J Clin Microbiol* 52: 2210-2211 (2014)]. Such systems not only necessitate bulky and specialized equipment, for PCR thermal cycling and fluorescence measurements, but also require trained personnel to operate. Advanced isothermal amplification assays have been developed to relieve the instrument needs for temperature cycling; nevertheless, these assays have their own limitations. For example, loop-mediated isothermal amplification (LAMP) has stringent sequence requirements and cannot be easily generalized [Zhao, Y., et al., *Chem Rev* 115: 12491-12545 (2015)]. Importantly, as with other nucleic acid amplification approaches, LAMP is prone to false-positives (e.g., from primer-dimer formation). Alternatively, sequence-specific signaling probes (e.g., fluorescent Taqman reporter) could be used to improve the detection accuracy; however, these probes are expensive and complex to implement [Gardner, S. N., et al., *J Clin Microbiol* 41: 2417-2427 (2003)]. As each piece of DNA target requires a dedicated, sequence-specific probe for coupled signaling during target amplification, the approach becomes increasingly costly and challenging to multiplex or perform complex computations [Juskowiak, B. *Anal Bioanal Chem* 399: 3157-3176 (2011)].

There is a need for a molecular platform to enable rapid, visual and modular detection of nucleic acids.

SUMMARY OF THE INVENTION

Instead of relying on target nucleic acid amplification, the technology of the present invention exponentially enhances visual signal from direct and independent target hybridization. Termed enzyme-assisted nanotechnology for visual identification of nucleic acids (enVision), the present invention consists of an integrated circuit of two independent enzyme-DNA nanostructures—an easily adjustable recognition element and a sensitive universal signaling element—to decouple target recognition and visual signal amplification. DNA nanostructures were chosen as the functional elements as they can be designed to harbor stable three-dimensional conformations to facilitate diverse enzymatic activities and have minimal cross-talk, even when packed closely, to enable independent operations [Lee, H. et al. *Nat Nanotechnol* 7: 389-393 (2012); Wang, L., et al., *Nucleic Acids Res* 45: 12090-12099 (2017); Li, J., et al., *Nat Chem* 9: 1056-1067 (2017)].

In a first aspect there is provided a method of detecting target nucleic acids in a sample, comprising the steps of:
  (a) providing a sample comprising nucleic acid;
  (b) providing a composition comprising at least one DNA polymerase enzyme and at least one recognition nanostructure, wherein the recognition nanostructure comprises a DNA polymerase enzyme-specific DNA aptamer having a conserved sequence region and a variable sequence region, wherein the variable sequence region comprises an overhang segment which is at least 10 nucleotides complementary to a target nucleic acid in the sample; or
  (c) providing a composition comprising at least one DNA polymerase enzyme and at least one recognition nanostructure, wherein the recognition nanostructure comprises a DNA polymerase enzyme-specific DNA aptamer and an inverter oligonucleotide, wherein the aptamer has a conserved sequence region and a variable sequence region, wherein the variable sequence region comprises an overhang segment which is at least 10 nucleotides complementary to, and forms a duplex with, a portion of the inverter oligonucleotide, wherein the inverter oligonucleotide is at least one nucleotide longer than the aptamer-inverter duplex, thereby creating an inverter overhang, and has more than 10 nucleotides complementary to a target nucleic acid in the sample;
(d) contacting the sample comprising nucleic acid with the composition of (b) or (c), wherein target nucleic acid binding to:
  (i) the variable sequence region of the aptamer in (b) promotes the formation of a stable aptamer-DNA polymerase enzyme complex, thereby inhibiting DNA polymerase enzyme activity; or
  (ii) the inverter oligonucleotide in (c) destabilizes the recognition nanostructure, thereby releasing the DNA polymerase enzyme from inhibition by the DNA aptamer;
(e) providing a signaling nanostructure that is reactive to active DNA polymerase enzyme from step (d), wherein the signaling nanostructure comprises a self-priming portion responsive to the DNA polymerase enzyme;
(f) contacting the signaling nanostructure with active DNA polymerase enzyme from step (d) in the presence of labelled oligonucleotides (dNTPs) and signal development reagents, wherein the activated DNA polymerase enzyme adds labelled oligonucleotides to the signaling nanostructure and the signal development reagents bind to the labelled oligonucleotides incorporated into the self-primed portion;
(g) detecting signal development, wherein the intensity of signal indicates;
  (i) absence of target nucleic acid in the sample when using composition (b); or
  (ii) the presence of target nucleic acid in the sample when using composition (c).

In some embodiments the DNA polymerase enzyme is Taq polymerase, a thermostable DNA polymerase named after the thermophilic bacterium *Thermus aquaticus* from which it was originally isolated.

In some embodiments the DNA aptamer conserved sequence region comprises the nucleic acid sequence 5'-CAATGTACAGTATTG-3' (SEQ ID NO: 153).

In some embodiments the inverter oligonucleotide is at least one nucleotide longer than the aptamer duplex region. Preferably, the inverter oligonucleotide is about twice as long as the aptamer duplex region.

In some embodiments, about half of the inverter oligonucleotide length forms the aptamer-inverter duplex and about half forms an overhang segment.

In some embodiments the method according to any aspect of the invention, further comprises providing a second recognition nanostructure complementary to a target nucleic acid different from the target nucleic acid of a first recognition nanostructure in the sample, for duplex detection.

In some embodiments the method provides additional recognition nanostructure(s) each having an inverter sequence which is complementary to a target nucleic acid different from the target nucleic acids of other recognition nanostructures in the sample, for multiplex detection. Examples of suitable aptamer and inverter oligonucleotide sequences for multi-loci HPV detection are shown in Table 4.

In some embodiments mismatches are introduced into the inverter oligonucleotide overhang to accommodate target nucleic acid sequence variability, useful for pan detection. Examples of suitable aptamer and inverter oligonucleotide sequences for pan detection of HPV are shown in Table 2.

In some embodiments mismatches are introduced into the variable sequence region duplex to confer strong sequence specificity, useful for multiplex detection of closely related target nucleic acids such as for subtyping virus. Examples of suitable aptamer and inverter oligonucleotide sequences for subtyping HPV are shown in Table 2.

In some embodiments the method further comprises providing one or more additional recognition nanostructures complementary to one or more target nucleic acids different from the target nucleic acid of a first recognition nanostructure in the sample, for multiplex detection.

In some embodiments each of the recognition nanostructures comprise a combination of DNA aptamer:inverter oligonucleotide:DNA polymerase enzyme ratio of each recognition nanostructure to form a logic gate selected from a group comprising AND, OR, NOT, NAND and NOR. Examples of suitable aptamer and inverter oligonucleotide sequences for logic gate detection of HPV are shown in Table 5.

In some embodiments the combination of recognition nanostructure and DNA aptamer:inverter oligonucleotide:DNA polymerase enzyme ratio of each recognition nanostructure are selected from the group (i) to (v) comprising:
  (i) two nanostructures each having 1:1:0.5 DNA aptamer:inverter oligonucleotide:DNA polymerase enzyme ratio to form a AND logic gate;
  (ii) two nanostructures each having 1:1:1 DNA aptamer:inverter oligonucleotide:DNA polymerase enzyme ratio to form a OR logic gate;
  (iii) one nanostructure having 1:0:1 to form a NOT logic gate;
  (iv) two nanostructures each having 1:0:1 DNA aptamer:inverter oligonucleotide:DNA polymerase enzyme ratio to form a NAND gate; and
  (v) two nanostructures each having 1:0:0.5 DNA aptamer:inverter oligonucleotide:DNA polymerase enzyme ratio to form a NOR gate.

In some embodiments a combination of logic gate groups (i) to (v) as described above allows more than two targets to be detected.

In some embodiments the logic functions can be used to perform molecular computation, such as wherein the OR function improves detection coverage and/or the AND function improves detection specificity.

In some embodiments the self-priming portion of the signaling nanostructure comprises the nucleic acid sequence:

(SEQ ID NO: 5)
5'-AGCAGGCAGTTACGGGCTGGTGCGATGAGAGACGCGGAGTGTGGCGG

CCGGATAGTAATGACTGCGACCGGTGTACCAGTGGCGTGAGGCAGGTCGT

GAGGCGGCGTACGTAGAGCGTTGAGCAGGATGCCAACAGTCGATCAGGAC

GAGTGCTAACGCATTGTCGATAGCTCAGCTGTCTGAGCTATCGACAATGC

GTT-3'.

In some embodiments the target is at least one nucleic acid selected from the group comprising DNA, RNA, PNA and other nucleic acid analogs.

In some embodiments the target is at least one nucleic acid associated with a non-human or human disease, genetic variants, forensic, strain identification, environmental and/or food contamination.

In some embodiments the target is a pathogen. In some embodiments the pathogen is a virus. A non-limiting example of a virus is HPV as shown herein, which can be detected and/or characterized according to the methods of the invention.

In some embodiments the dNTP label used in the signaling step is biotin.

In some embodiments the signal development reagents comprise a fusion protein comprising avidin or a derivative thereof and an enzyme, selected from a group comprising but not limited to HRP, beta-lactamase, amylase, beta-galactosidase, and respective substrates selected from a group comprising but not limited to DAB, TMB, ABTS, nitrocefin, luminol, starch and iodine, wherein signals can be measured and quantified as but not limited to colour, fluorescence, luminescence or electrochemical changes.

In some embodiments step (a) is preceded by amplification of the target nucleic acid in the sample.

In some embodiments the amplification of the target nucleic acid in the sample is by nested asymmetric PCR or isothermal amplification methods.

In some embodiments the detection and signaling steps are physically and/or spatially separated.

In some embodiments the detection and signaling nanostructures are attached to a substrate.

In some embodiments the signaling nanostructures are attached to beads.

In some embodiments the detection and signaling nanostructures are attached to a microfluidic device or lateral flow device.

In some embodiments one or more of the method the steps a) to e) are performed at a temperature in the range from 16° C. to 40° C. In some embodiments steps d) to g) are performed at a temperature in the range from 16° C. to 40° C.

In some preferred embodiments one or more of the method the steps a) to e) are performed at ambient temperature. In some preferred embodiments steps d) to g) are performed at ambient temperature.

In some embodiments steps a) to d) are independent of steps e) to g). Alternative mechanisms to release enzyme activity in response to a stimulus can be used in steps a) to d). Alternative mechanisms may include enzyme inhibition through proximity with its inhibitors, temperature changes, alternative DNAzymes, etc. Alternative mechanisms to readout enzyme activity can be used in steps e) to g) for detection of different stimuli after activation of steps a) to d).

According to another aspect of the invention, there is provided an isolated signaling nanostructure nucleic acid comprising a self-priming portion which comprises the nucleic acid sequence:

```
                                        (SEQ ID NO: 5)
5'-AGCAGGCAGTTACGGGCTGGTGCGATGAGAGACGCGGAGTGTGGCGG

CCGGATAGTAATGACTGCGACCGGTGTACCAGTGGCGTGAGGCAGGTCGT

GAGGCGGCGTACGTAGAGCGTTGAGCAGGATCCAACAGTCGATCAGGACG

AGTGCTAACGCATTGTCGATAGCTCAGCTGTCTGAGCTATCGACAATGCG

TT-3'.
```

According to another aspect of the invention there is provided a device comprising said composition b) or composition c), as hereinbefore defined at a $1^{st}$ location, said signaling nanostructures, as hereinbefore defined, attached at a $2^{nd}$ location and an intermediate stage for mixing of said detection nanostructures with sample nucleic acid to release active enzyme to said $2^{nd}$ location.

In some embodiments the intermediate stage is a fluid channel connecting the $1^{st}$ and $2^{nd}$ locations.

A device according to the above improves the reaction kinetics and sensitivity of the method of detecting specific nucleic acids in a sample according to the invention, in part due to optimizing the duration of different enzyme activities.

An alternative device configuration according to the invention comprises said detection and said signaling nanostructures in a first location, wherein the signaling nanostructures are attached to beads and mixed with the detection nanostructures in the first location, after which the beads can be trapped in place at that location or at a $2^{nd}$ location to release active enzyme at its given location.

In some embodiments the device is selected from a group comprising a microfluidic device and a lateral flow device.

Preferably, the device is a microfluidic device as hereinbefore described. Examples of such a device are shown in FIGS. 1, 6 and 7. With reference to FIG. 1 and FIG. 6, it would be understood that in some embodiments the $1^{st}$ location may be where the sample to be tested is loaded onto a microfluidic device and comes into contact with pre-loaded detection nanostructures. The sample and detection nanostructures may then mix and interact while passing through an intermediate fluid channel, whereby positive detection releases active polymerase enzyme. The active enzyme then enters a $2^{nd}$ location (reaction chamber) which is pre-loaded with immobilized universal signaling nanostructures, where it polymerizes the generation of signaling molecules comprising labelled oligonucleotides and signal development reagents bind to the incorporated labelled oligonucleotides.

According to another aspect of the invention there is provided a nucleic acid detection kit comprising;
 (a) a composition comprising at least one DNA polymerase enzyme and at least one recognition nanostructure, wherein the recognition nanostructure comprises a DNA polymerase enzyme-specific DNA aptamer having a conserved sequence region and a variable sequence region, wherein the variable sequence region comprises an overhang segment which is at least 10 nucleotides complementary to a target nucleic acid; and/or
 (b) a composition comprising at least one DNA polymerase enzyme and at least one recognition nanostructure, wherein the recognition nanostructure comprises a DNA polymerase enzyme-specific DNA aptamer and an inverter oligonucleotide, wherein the aptamer has a conserved sequence region and a variable sequence region, wherein the variable sequence region comprises an overhang segment which is at least 10 nucleotides complementary to, and forms a duplex with, a portion of the inverter oligonucleotide, wherein the inverter oligonucleotide is at least one nucleotide longer than the aptamer-inverter duplex and has more than 10 nucleotides complementary to a target nucleic acid; and/or
 (c) a signaling nanostructure that is reactive to active DNA polymerase enzyme, wherein the signaling nanostructure comprises a self-priming portion responsive to the DNA polymerase enzyme; and/or
 (d) labelled oligonucleotides (dNTPs) and signal development reagents, wherein active DNA polymerase enzyme adds labelled oligonucleotides to the signaling nanostructure and the signal development reagents bind to the labelled oligonucleotides incorporated into the self-primed portion.

In some embodiments the nucleic acid detection kit of the invention comprises (a) to (d) as hereinbefore defined according to any aspect of the invention.

In some embodiments the nucleic acid detection kit of the invention is configured into a device as hereinbefore defined according to any aspect of the invention.

According to another aspect of the invention there is provided a method of diagnosing a disease in a subject, comprising the steps of:
(a) providing a sample comprising nucleic acid from the subject;
(b) providing a composition comprising at least one DNA polymerase enzyme and at least one recognition nanostructure, wherein the recognition nanostructure comprises a DNA polymerase enzyme-specific DNA aptamer having a conserved sequence region and a variable sequence region, wherein the variable sequence region comprises an overhang segment which is at least 10 nucleotides complementary to a target nucleic acid in the sample; or
(c) providing a composition comprising at least one DNA polymerase enzyme and at least one recognition nanostructure, wherein the recognition nanostructure comprises a DNA polymerase enzyme-specific DNA aptamer and an inverter oligonucleotide, wherein the aptamer has a conserved sequence region and a variable sequence region, wherein the variable sequence region comprises an overhang segment which is at least 10 nucleotides complementary to, and forms a duplex with, a portion of the inverter oligonucleotide, wherein the inverter oligonucleotide is at least one nucleotide longer than the aptamer-inverter duplex, thereby creating an inverter overhang, and has more than 10 nucleotides complementary to a target nucleic acid in the sample;
(d) contacting the sample comprising nucleic acid with the composition of (b) or (c), wherein target nucleic acid binding to:
    (i) the variable sequence region of the aptamer in (b) promotes the formation of a stable aptamer-DNA polymerase enzyme complex, thereby inhibiting DNA polymerase enzyme activity; or
    (ii) the inverter oligonucleotide in (c) destabilizes the recognition nanostructure, thereby releasing the DNA polymerase enzyme from inhibition by the DNA aptamer;
(e) providing a signaling nanostructure that is reactive to active DNA polymerase enzyme from step (d), wherein the signaling nanostructure comprises a self-priming portion responsive to the DNA polymerase enzyme;
(f) contacting the signaling nanostructure with active DNA polymerase enzyme from step (d) in the presence of labelled oligonucleotides (dNTPs) and signal development reagents, wherein the activated DNA polymerase enzyme adds labelled oligonucleotides to the signaling nanostructure and the signal development reagents bind to the labelled oligonucleotides incorporated into the self-primed portion;
(g) detecting signal development, wherein the intensity of signal indicates;
    (i) absence of the target nucleic acid in the sample when using composition (b); or
    (ii) the presence of the target nucleic acid in the sample when using composition (c)
(h) diagnosing the subject with the disease when presence of target nucleic acid in the sample is detected.

In some embodiments, the disease is a pathogenic disease. In some embodiments the disease is HPV-related.

In some embodiments, HPV is detected using one or more aptamer and/or inverter oligonucleotides listed in Tables 2, 4 and 5.

According to any aspect of the present invention, at least one of the aptamer and/or inverter and/or signaling nanostructure oligonucleotides is structurally and/or chemically modified from its natural nucleic acid.

In some embodiments, said structural and/or chemical modifications are selected from the group comprising the addition of phosphorothioate (PS) bonds, 2'-O-Methyl modifications, phosphoramidite C3 Spacers and 5' additions such as amino, thiol, acryldite or azide groups during synthesis.

BRIEF DESCRIPTION OF FIGURES

FIG. 7 shows a schematic of the operation of a device according to the invention.

FIG. 11 shows nested asymmetric amplification. (a) Schematic of the nested amplification. To significantly expand the population of single-stranded DNA for minuscule amounts of samples, a nested asymmetric PCR amplification was employed. The samples were first exponentially amplified, in the presence of equally concentrated dual primers, and subsequently linearly amplified, using an excess of a single primer. (b) Efficiency of the nested asymmetric amplification. Amplification products from (1) 1 pmole, (2) 100 fmole, (3) 10 fmole, (4) 1 fmole, (5) 100 amole, (6) 10 amole, (7) 1 amole, and (8) no template control of synthetic HPV16 sequence were analyzed on an 8% PAGE gel. The upper arrow indicates larger, double-stranded products while the lower arrow corresponds to single-stranded products.

FIG. 12 shows nucleic acid sequence based amplification (NASBA). (a) Schematic of NASBA. DNA targets were first primed for RNA transcription and single-stranded RNA amplification via the T7 RNA polymerase. The RNA products were then reverse transcribed into cDNA before being subjected to RNA digestion to produce single-stranded DNA products. (b) Efficiency of NASBA. Amplification products from (1) 1 pmole, (2) 100 fmole, (3) 10 fmole, (4) 1 fmole, (5) 100 amole, (6) 10 amole, (7) 1 amole, and (8) no template control of synthetic HPV 16 sequence were analyzed on an 8% PAGE gel. The arrow indicates the expected size of the DNA products.

FIG. 16 shows the use of enVision OR and AND logic gates to detect combinations of multiple targets. By varying the combination of recognition nanostructures as well as the ratio of different components (i.e., aptamer, inverter and polymerase) in each nanostructure, we show the use of logic gates to detect multiple targets simultaneously. All measurements were performed in triplicate, and the data are displayed as mean±s.d.

DETAILED DESCRIPTION OF THE INVENTION

Figure 1:
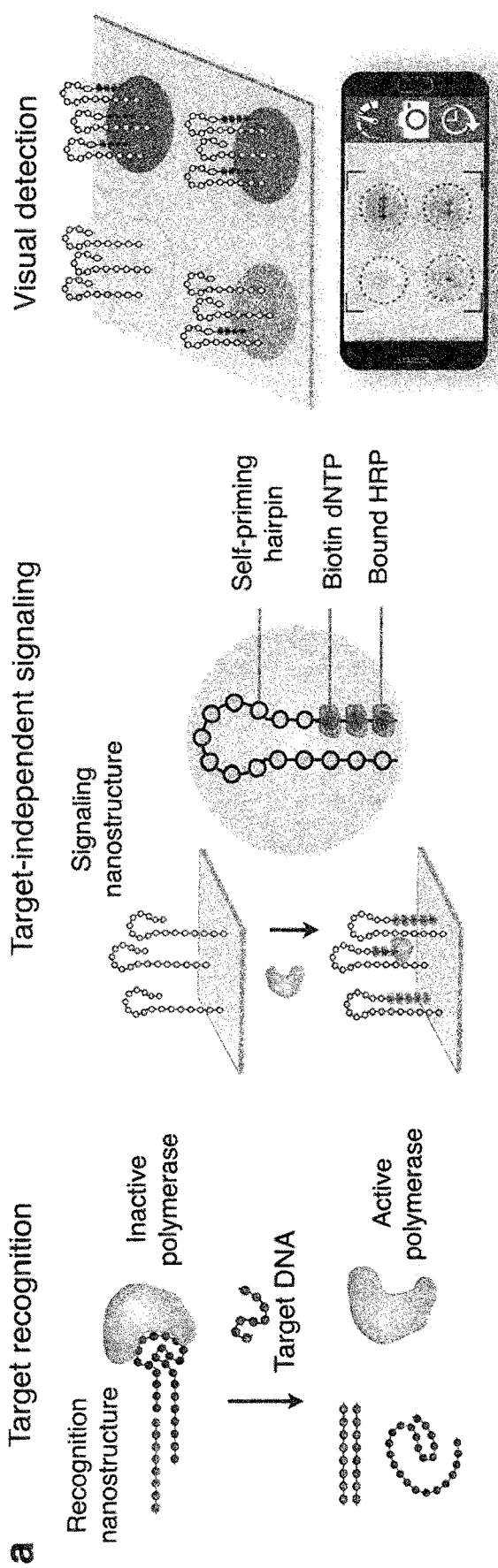
FIG. 1 shows visual and modular detection of pathogen nucleic acids. (a) The enVision system consists of a series of enzyme-DNA nanostructures to enable target recognition, target-independent signaling, and visual detection. The nanostructures are designed to decouple recognition from signaling. The recognition nanostructure is a hybrid complex, composed of an inactivating aptamer and a Taq DNA polymerase. In the presence of complementary target DNA, the complex dissociates to activate the polymerase activity. The active polymerase proceeds to elongate a universal, self-priming signaling nanostructure, in a target-independent manner. Modified deoxynucleotides (dNTPs) are incorporated to immobilize horseradish peroxidase (HRP) onto the signaling nanostructures. Upon the addition of optical substrate, visual signals can be enzymatically enhanced, detected by the naked eye and quantified with a smartphone camera. Photograph (inset) shows an example of the actual visual readouts in the presence of none (−) and varying (+) amounts of target DNA on a smartphone application. (b) Schematic of the enVision microfluidic system. The platform is designed to complement the modular enVision workflow. Independent assay cassettes, preloaded with specific recognition nanostructures at the inlets, can be mounted on-demand onto a common signaling cartridge. The common cartridge houses the universal signaling nanostructures, which are immobilized on embedded membranes, for target-independent signaling and visual detection. Direction of cassette sliding is indicated by an arrow. (c) Photograph of the microfluidic enVision prototype, developed for versatile assay integration and parallel processing.
Figure 1:
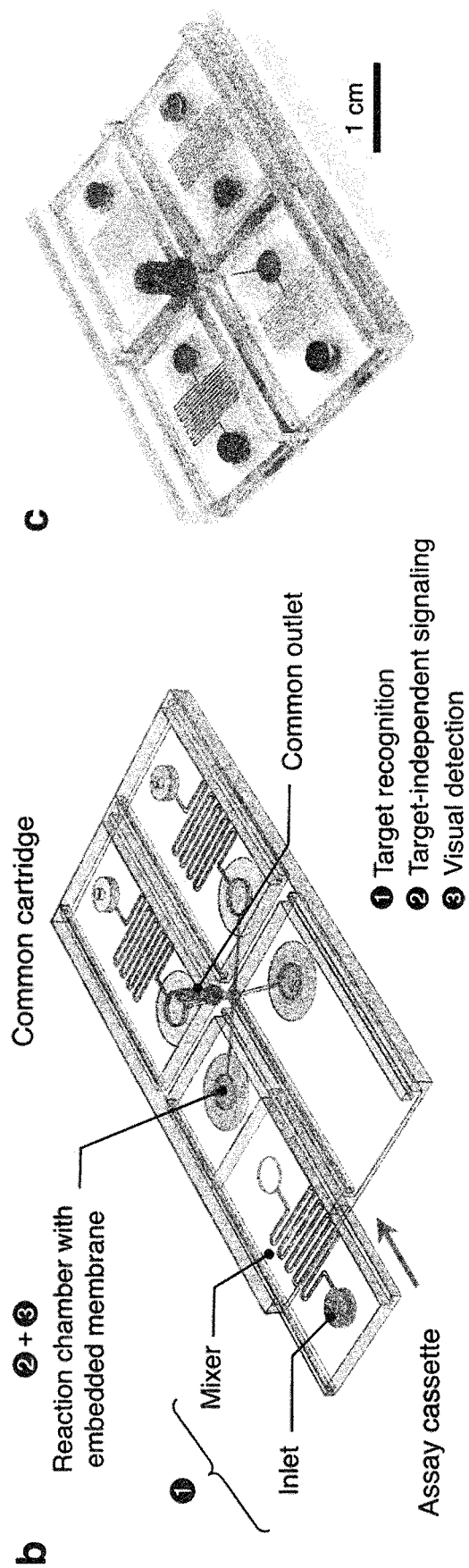

The advantages of the present invention are multifold. First, sensing mechanism—the technology activates immediately upon target hybridization to transduce significant signal enhancement. By incorporating a dual-enzyme signaling cascade (e.g., DNA polymerase and horseradish peroxidase), the technology benefits from the activities of both enzymes for visual detection of diverse targets. Even in the absence of target nucleic acid amplification, the enVision platform produces a rapid and sensitive color readout that is visible to the naked eye and quantifiable by smartphones. Due to this sensing mechanism, the technology could be applied to detect different types of nucleic acids accurately and directly (e.g., DNA and RNA, no need for cDNA conversion), without requiring extensive equipment. Second, assay programmability—by decoupling recognition from signaling, the technology enables modular detection and versatile integration. New assays could be readily designed by modifying a single sequence region in the highly programmable recognition element alone and configured to perform logic computations. The universal signaling element could be used for all visual measurements. When implemented on a configurable microfluidic platform, the enVision technology thus showed a high detection sensitivity and programmability, to enable visual profiling of diverse pathogen nucleic acids from infected cells at room temperature. Through multi-loci multiplexing in a single reaction, we further developed a high-coverage enVision system to interrogate various virus-host genome integration loci. Using HPV as a clinical model, we demonstrated the technology's clinical utility for molecular-typing of infections in patient endocervical samples, by improving inter-subtype differentiation as well as intra-subtype detection coverage.

Bibliographic references mentioned in the present specification are for convenience listed in the form of a list of references and added at the end of the Examples. The whole content of such bibliographic references is herein incorporated by reference.

Definitions

Unless defined otherwise, all technical and scientific terms used herein have the same meaning as is commonly understood by one of skill in the art to which the invention belongs. Certain terms employed in the specification, examples and appended claims are collected here for convenience.

It must be noted that as used herein and in the appended claims, the singular forms "a," "an," and "the" include plural reference unless the context clearly dictates otherwise. Thus, for example, a reference to "a target sequence" includes a plurality of such target sequences, and a reference to "an enzyme" is a reference to one or more enzymes and equivalents thereof known to those skilled in the art, and so forth.

As used herein, the term "aptamer", refers to single stranded DNA or RNA molecules. An aptamer is capable of binding various molecules with high affinity and specificity. For example, as used herein, in the absence of target DNA, the DNA aptamer binds strongly with the polymerase to inhibit polymerase activity.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material.

As used herein, the term "oligonucleotide", refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

Figure 3:
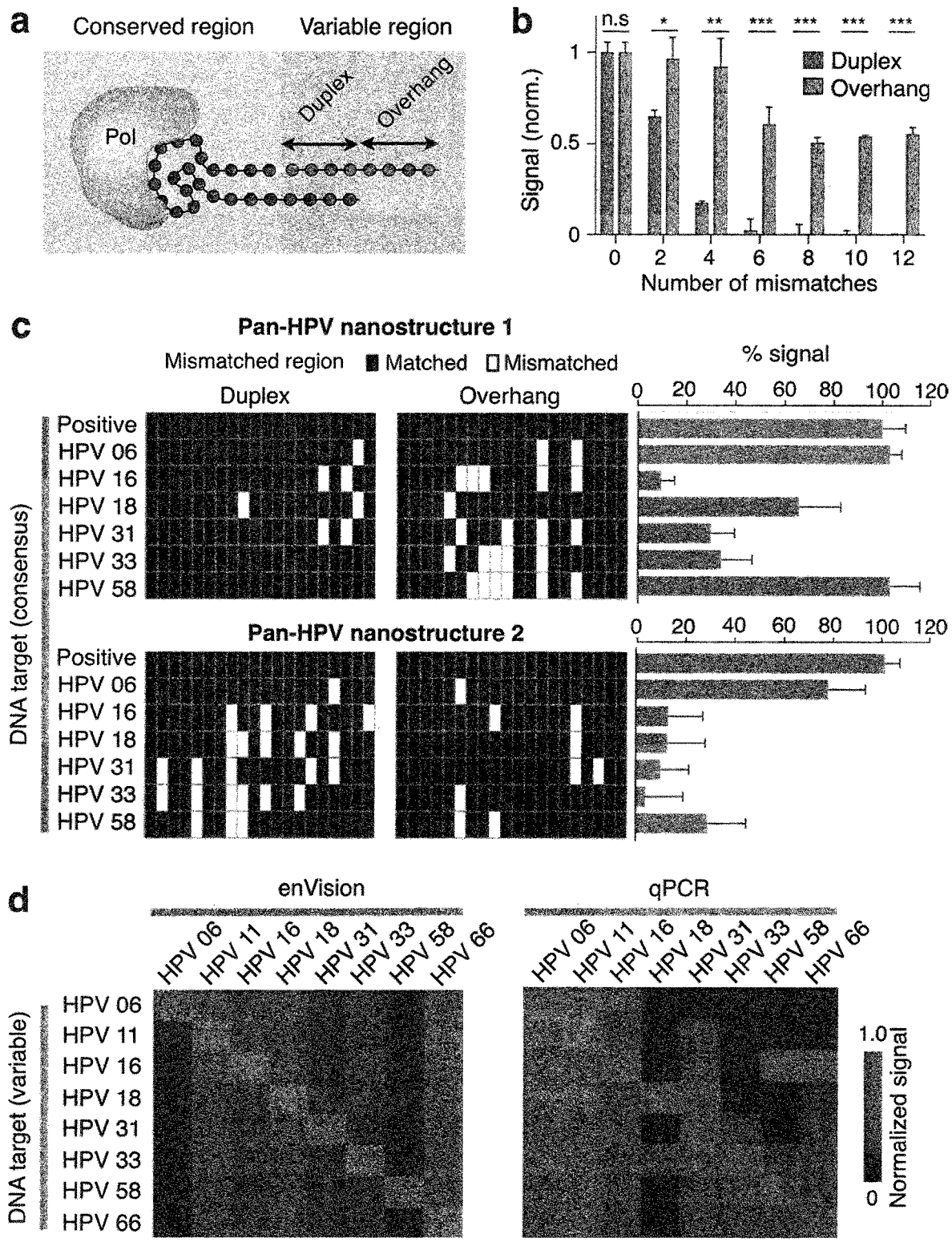
FIG. 3 shows the programmability of enVision. (a) Schematic of the programmable recognition nanostructure. The hybrid structure consists of a conserved sequence region, that binds to inactivate DNA polymerase (pol), and a variable region (duplex and overhang segments) that can be made complementary to target DNA. Not drawn to scale. (b) Effects of target mismatches in the variable region. Synthetic DNA targets, designed to have varying numbers of mismatches against the variable region, were incubated with the recognition nanostructure. All signals were normalized against that of the complementary DNA target (0 mismatch). Mismatches against the duplex region produced significantly lower signals (*$P<0.05$,  $P<0.005$, *$P<0.0005$, n.s. not significant, Student's t test). (c) Pan-HPV recognition. Two pan-HPV recognition nanostructures were developed according to the HPV consensus genome, to harbor different numbers of mismatches against DNA targets obtained from six HPV subtypes. All mismatches were mapped to the duplex and overhang regions. Nanostructure 1, which accommodated more mismatches in the overhang region, demonstrated better pan-recognition capability. All signals were normalized against that of the complementary DNA target (positive). (d) Comparison of enVision and qPCR measurements for specific HPV subtyping. Specific nanostructures were designed according to a highly variable region of the HPV genome with sequence variations contained within the sensitive duplex region. DNA targets from different HPV subtypes were measured via color intensity through the enVision smartphone platform (left) and cycle counts through the SYBR®-Green qPCR system (right). All signals were acquired relative to appropriate controls (i.e., water as a no-template control). Signals from respective detection systems were globally presented in the form of heat maps for comparisons of assay performance. All measurements were performed in triplicate, and the data are displayed as mean±s.d. in (b) and (c).

As used herein, the term "inverter sequence" or "inverter oligonucleotide" refers to an oligonucleotide which is complementary to a target nucleic acid sequence, of which a portion is involved in forming a duplex and a portion is involved in an overhang. Herein it is shown that a longer sequence of 20 nucleotides each for the duplex and overhang sequence robustly produces its inhibitory effect by stabilizing the aptamer binding to the DNA polymerase enzyme. This inhibitory effect can be removed in the presence of a complementary target at ambient temperatures. The presence/absence of the inverter sequence determines the functional state of the recognition element (e.g., on or off state). In its presence, the polymerase activity is turned on with targets; in its absence, the polymerase activity can be turned off with targets. FIG. 3a shows a schematic of the polymerase, aptamer and inverter arrangement.

As used herein, the term "variable sequence region" refers to a region that determines the sequence specificity to the target sequences (i.e., defines the target sequences that can be recognized). The inverter sequence and part of the aptamer sequence is contained within this variable sequence region. This region can be changed to enable detection of new targets. When no inverter is used the "variable sequence region" refers to an overhang segment on the aptamer that is complementary to target nucleic acid.

The term "sample," as used herein, is used in its broadest sense. For example, a biological sample suspected of containing HPV genome sequences, including but not exclusively HPV 6, 16, 18, 31, 33, and 5, may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

It would be understood that oligonucleotides used in the present invention may be structurally and/or chemically modified to, for example, prolong their activity in samples potentially containing nucleases, during performance of methods of the invention, or to improve shelf-life in a kit. Thus the aptamer and/or inverter and/or signaling nanostructure or any oligonucleotide primers or probes used according to the invention may be chemically modified. In some embodiments, said structural and/or chemical modifications include the addition of tags, such as fluorescent tags, radioactive tags, biotin, a 5' tail, the addition of phosphorothioate (PS) bonds, 2'-O-Methyl modifications and/or phosphoramidite C3 Spacers during synthesis.

For example, the signaling oligonucleotide was modified for attachment chemistry with a 5' amino group. Other attachment modifications can be made on the 5' end such as thiol, acryldite, azide, etc.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

EXAMPLES

Standard molecular biology techniques known in the art and not specifically described were generally followed as described in Green and Sambrook, Molecular Cloning: A Laboratory Manual, Cold Spring Harbour Laboratory, New York (2012).

Example 1

Methods
Recognition Nanostructure Characterization

All sequences can be found in Tables 1-7 and were purchased from Integrated DNA Technologies (IDT). To prepare the recognition nanostructure, we mixed an equal molar ratio of DNA aptamer and inverter oligonucleotide in a buffer of 50 mM NaCl, 1.5 mM $MgCl_2$, and 50 mM Tris-HCl buffer (pH 8.5). The mixture was incubated at 95° C. for 5 minutes and slowly cooled at 0.1° C./s until the reaction reached 25° C., before the addition of Taq DNA polymerase (GoTaq®, Promega) to form the hybrid complex. To characterize the assembly and activity of the recognition nanostructure in the presence of DNA targets, varying concentrations of target oligonucleotides were added to this mixture. Real-time association and dissociation kinetics of the complex were measured by bio-layer interferometry (Pall Fortebio). Briefly, pre-assembled biotin-aptamer was immobilized onto streptavidin-functionalized interferometry sensor. After a brief washing step, Taq polymerase was added; this was followed by an incubation with target oligonucleotides. All binding data (changes in optical thickness of the biolayer) were measured as wavelength shifts, in a continuous manner. We further measured the polymerase activity through 5' exonuclease degradation of Taqman® probes (Applied Biosystems). Fluorescence readings were taken every two minutes, in the presence of the Taqman® probe, and normalized as described (see Data normalization below) to compare the resultant polymerase activity.

Signaling Nanostructure Characterization

Stability of the signaling nanostructure, as compared to that of a similarly-sized linear template, was determined in two different ways. First, we annealed both reactions (i.e., nanostructure and linear template) at room temperature, and analyzed the primed vs. unprimed fractions in each reaction through gel electrophoresis. Second, a melting curve analysis was performed by mixing the oligonucleotides with 10,000× diluted SYBR® Green I dye (Invitrogen), heating the reaction to 90° C., fast cooling to 45° C. at 1.6° C./s, and slow heating to 90° C. at 0.075° C./s while visualizing the intercalated fluorescence intensity (Applied Biosystems). We further determined the ability of the signaling nanostructure to improve polymerase activity through Taqman® analysis. The polymerase activity was determined at different nucleotide positions away from the starting primed sites, through 5' exonuclease degradation of differentially placed Taqman® probes (Applied Biosystems).

enVision Device Fabrication

A prototype enVision device comprising 4 assay cassettes and a common cartridge was fabricated from polydimethylsiloxane (PDMS, Dow Corning) and poly(methyl methacrylate) (PMMA) respectively. Each assay cassette was fabricated by plasma bonding two layers of PDMS pieces together (50 mTorr, 50 W, 1 min). The 200 µm-thick cast molds were prepared via conventional photolithography using SU-8 photoresist and silicon wafers. Reaction chambers and microchannels were replicated by pouring uncured PDMS (10:1 elastomer base to curing agent ratio) onto the cast molds. After polymer curing (75° C. for 30 min), the two PDMS pieces were assembled together. The common cartridge was fabricated by $CO_2$ laser ablation (Universal Laser Systems). Four polycarbonate membranes with pore size of 0.2 µm (Avanti Polar Lipids) were embedded between the two PMMA layers thermally bonded together (125° C. for 30 min). A NanoPort™ assembly (Upchurch Scientific.) was adhered to the outlet on the common cartridge to allow for fluidic connection.

Signaling Nanostructure Immobilization

Amine-modified oligonucleotides (IDT) were used for functionalization. To immobilize the oligonucleotides onto the microfluidic device, polystyrene beads were used to increase the surface area for anchoring the oligonucleotides. 3 µm carboxylic acid-modified polystyrene beads (Spherotech) were washed in PBS buffer before being resuspended in MES buffer (Thermo Fisher Scientific). The beads were activated with EDC/sulfo-NHS (Pierce Biotechnology) for 15 minutes at room temperature, and incubated with excess 5' amine-modified oligonucleotides in PBS buffer at room temperature for 2 hours. The beads were then washed through centrifugation and resuspended in 10 mM Tris-EDTA buffer.

Device Preparation

To prepare the device for operation, the bead-immobilized signaling nanostructures were lyophilized as well as the modified dNTP reaction mixture onto the common cartridge. All devices were flushed with ethanol and PBS buffer before lyophilization. Briefly, a 4 mM stock dNTP reaction mixture was prepared by mixing dATP, dGTP, dTTP, and 25% dCTP: 75% biotin-16-aminoallyl-2'-dCTP (Trilink biotechnologies). 50 µg of DNA-functionalized polystyrene beads (3 µm, prepared as above) were introduced in 20 µl of dNTP mixture onto the device polycarbonate membranes, and allowed to dry under vacuum for 30 minutes (Labconco FreeZone).

Operation of enVision Platform

Operation steps are illustrated in FIG. 7. Nucleic acid samples were added to the inlets of individual assay cassettes, each preloaded with assembled recognition nanostructures, in a buffer containing 50 mM NaCl, 1.5 mM $MgCl_2$, and 50 mM Tris-HCl at pH 8.5. The assay cassettes were then mounted onto the common signaling cartridge, prepared as described above. For the purpose of assay optimization, a syringe pump (Harvard Instruments) was used to exert a negative pressure at the common cartridge outlet to actuate parallel fluidic movement in all four assay cassettes. Each reaction mix would pass through a serpentine channel for effective mixing and polymerase activation (10 µl/min, 1 minute), before entering into a reaction chamber. The solution was then incubated for 20 minutes in the presence of DNA-functionalized polystyrene beads and dNTP reaction mixture. The beads were flushed in excess PBS buffer (10 µl/min, 3 minutes), before incubation with streptavidin-HRP (BD Biosciences, 3 minutes) and 3,3'-diaminobenzidine substrate (DAB, Thermo Fisher Scientific, 3 minutes).

As the crucial steps in the enVision workflow were largely incubation and washing, where precise flow rates become unnecessary, we could thus use a withdrawal septum (Thermo Fisher) to actuate fluid movement through negative pressure. All reactions were completed at room temperature, and included appropriate negative controls. Visual readouts of samples and controls were imaged directly using a mobile smartphone (Samsung). Color images were converted to greyscale, and the average (mean) black pixel intensity of each membrane area with trapped signaling DNA beads was used for numerical quantification of the signal.

Data Normalization $$\tilde{I}(\text{target}, t_i) = \frac{I(\text{target}, t_i) - \tilde{I}(\text{target}, t_o)}{I(\text{control}, t_i) - I(\text{control}, t_o)} - 1$$

where $\tilde{I}$ (target, $t_i$)=normalized signal intensity for target at a given time point ($t_i$);

I (target or control, $t_i$)=raw signal intensity for target or control at a given time point ($t_i$);

I (target or control, $t_o$)=raw signal intensity for target or control at time 0 ($t_o$)

We calculated the signal intensity difference (visual color or fluorescence) of a sample as the difference in intensity taken at a given time point ($t_i$) and its initial intensity ($t_o$). This value was then normalized to that of the control sample (no-target control) that was run concurrently. $\tilde{I}$(control, $t_i$) was scaled to 0 for data representation.

Sequence Design

HPV genome sequences were obtained from GenBank through the following reference numbers (HPV 6: AF092932.1, HPV 11: FR872717.1, HPV 16: K02718.1, HPV 18: AY262282.1, HPV 31: J04353.1, HPV 33: M12732.1, HPV 58: D90400.1, HPV 66: U31794.1). Multiple sequence alignment was performed using Clustal Omega software [Sievers, F. et al. *Mol Syst Biol* 7: 539 (2011)]. From the resulting sequence alignment, we defined highly conserved and divergent sequences to design the pan-recognition and subtype-specific recognition nanostructures, respectively. Briefly, we identified highly conserved regions (20 bp, <3 non-identical base pairs) which were flanked immediately upstream or downstream by less conserved regions (20 bp, <6 non-identical base pairs). We selected the most conserved motifs to form the recognition domain of our pan-HPV recognition nanostructures. To design subtype-specific recognition nanostructures, we located highly divergent regions (40 bp, <12 identical base pairs). A similar approach was used to define divergent regions in the L1, L2 and E1 genes of the HPV genome, and designed locus-specific recognition nanostructures for each HPV subtype to improve the detection coverage. All sequences designed can be found in the Tables.

Mismatch Characterization

To evaluate the mismatch sensitivity of the duplex and overhang region in the recognition nanostructure, we randomly mutated base pairs at every two-nucleotide interval in the complementary DNA targets and used the enVision platform to measure the resultant signal changes. To determine the pan-HPV detection capabilities of the recognition nanostructures, we used sequences of six HPV subtypes (HPV 6, 16, 18, 31, 33, and 58) as well as a fully complementary sequence (positive control) as the target sequences. We mapped the mismatched nucleotides to the duplex and overhang regions respectively and measured the resulted signal changes.

Asymmetric Amplification

In the case of minuscule amounts of samples, we prepared single-stranded DNA through a nested asymmetric PCR amplification. The amplification could be accomplished in <1 hour. For the exponential amplification, we used 0.8 µM of forward and reverse primers (IDT), and 5 units of GoTaq® DNA polymerase (Promega) in 1× GoTaq® buffer containing 2.5 mM dNTPs. This was followed by a linear asymmetric PCR amplification, where we used excess reverse primer only, in the presence of GoTaq® DNA polymerase (Promega) in 1× GoTaq® buffer containing 2.5 mM dNTPs. The following thermocycling conditions were used for the entire processing: 95° C. for 5 minutes, 35 cycles of 95° C. for 30 seconds and 52° C. for 60 seconds, and a final 4° C. holding step. The PCR solution was used directly for all subsequent measurements.

Isothermal Asymmetric Amplification

To achieve isothermal asymmetric amplification, nucleic acid sequence based amplification (NASBA) was adopted. The entire process could be completed in <1 hour. We used 4 µM of each of the forward and reverse primers (IDT), 80 units of T7 RNA polymerase, 1 unit of RNase H, 80 units of GoScript™ Reverse Transcriptase, and 1 unit of RNase Inhibitor (Promega) in 1× transcription optimized buffer containing 2.5 mM dNTPs, 5 mM NTPs, 6 mM $MgCl_2$, 5 mM DTT, and 15% DMSO. Upon sample addition, the mixture was maintained at 37° C. for 45 minutes, before being heated to 75° C. to halt the reaction.

SYBR® qPCR Comparison

The HPV subtype-specific sequences were used to perform this comparison. Subtype-specific detection of synthetic oligonucleotides was carried out on the enVision platform as described above. For qPCR experiments (Applied Biosystems), we designed specific PCR primer pairs to span the identical target sequences for each HPV subtype. Briefly, 100 fmol of synthetic template was mixed with 5 units of GoTaq® DNA polymerase (Promega) in 1× GoTaq® buffer containing 2.5 mM dNTPs and 0.8 µM forward and reverse primers, using the following thermal cycling protocol: 50° C. for 2 minutes, 95° C. for 10 minutes, 40 cycles of 95° C. for 15 seconds and 48° C. for 1 minute. All qPCR analyses were followed by a melting curve step ramping from 50° C. to 95° C. at a ramp rate of 0.075° C./s to determine any nonspecific amplification. A no-template control (water) was included for every primer assay to ensure that no primer dimers were formed in the qPCR reaction. The qPCR threshold cycle (Ct) signal was determined for each primer pair/template combination. The signal produced by each qPCR primer assay was normalized across all targets tested for the assay to determine the assay specificity.

Direct RNA Detection

We prepared RNA targets via T7 RNA Polymerase (New England Biolabs). Briefly, annealed DNA template with T7 promoter primer (Table 3) (1 pmol) was incubated with T7 RNA Polymerase in 1× buffer at 37° C. for 2 hours, before the addition of 2 units of RNase-Free DNase I (Promega) and incubation at 41° C. for 20 minutes. The produced RNA was precipitated in 0.3 M sodium acetate. This mixture was treated with 1 volume of isopropanol and incubated at 4° C. for 1 hour, before being centrifuged (12,000 g at 4° C. for 30 minutes). The pellet was washed twice in chilled ethanol (75%), centrifuged as before, and air-dried at room temperature. When dissolved in nuclease-free water, the final RNA concentration was determined through absorbance measurements (Nanodrop, Fisher Scientific). For direct RNA detection, we added the prepared RNA targets, in the presence of 1 unit of SUPERase RNase Inhibitor (SUPERase.ln™; Thermo Fisher), to the enVision system. All detection and data normalization were performed as described above.

Constructing enVision Logic Gates

Figure 15:
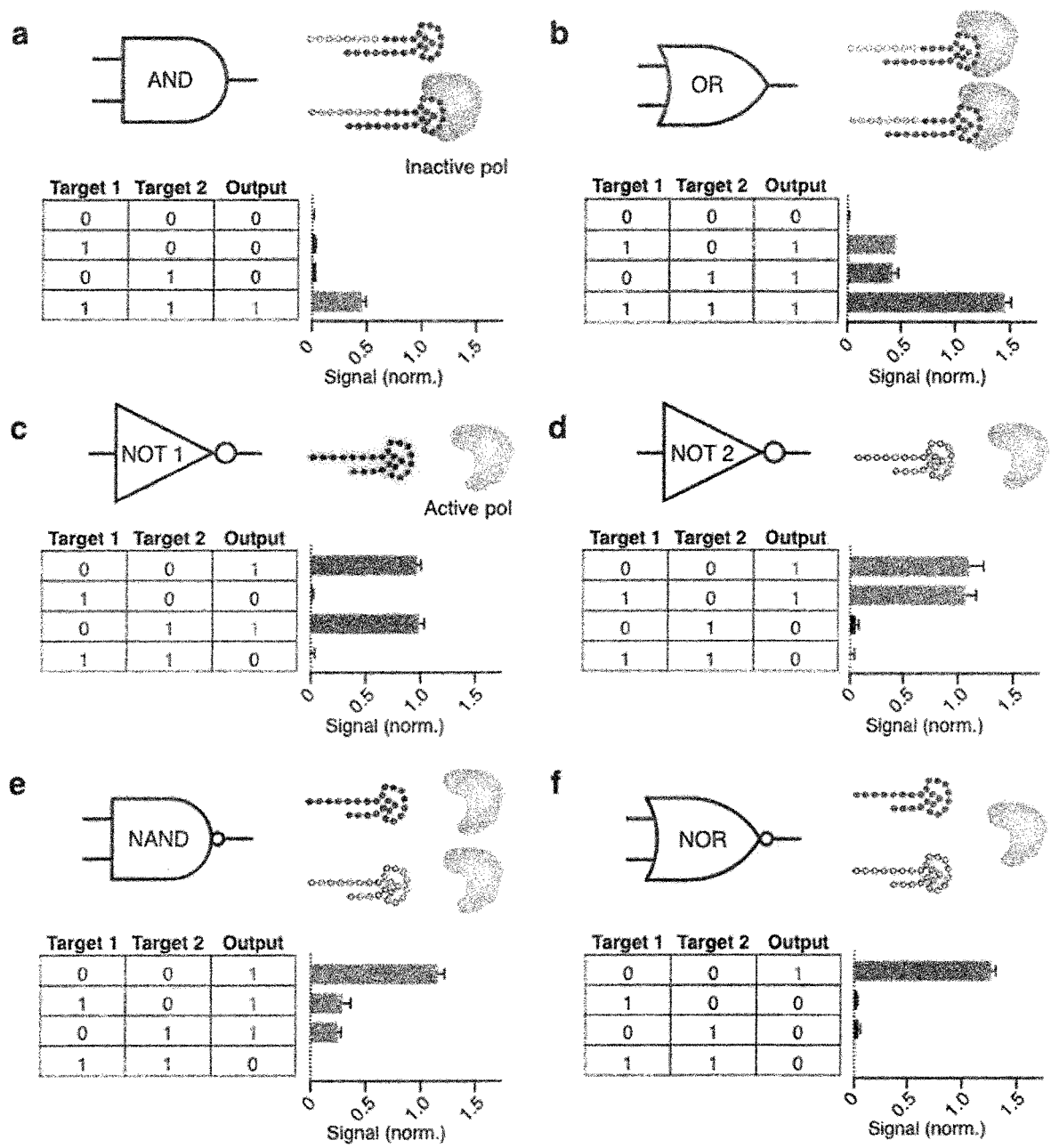
FIG. 15 shows enVision logic gates. By varying the combination of recognition nanostructures as well as the ratio of different components (i.e., aptamer, inverter and polymerase) in each nanostructure, we programmed the following logic computations: (a) AND gate, (b) OR gate, (c) NOT gate for HPV 16, (d) NOT gate for HPV 18, (e) NAND gate, and (f) NOR gate. For each gate designed, the components used to establish the configuration are illustrated (top right of each panel). Each gate was tested with different combinations of DNA targets, isolated from HPV 16 (Target 1) and HPV 18 (Target 2). All target combinations and their expected computational outputs are summarized in corresponding truth tables (bottom left of each panel). The observed enVision signals (bottom right of each panel) showed a good agreement with the expected outputs. All signals were normalized to appropriate controls (no-target controls) as previously described. Normalized signals above the detection threshold (i.e., 3×s.d. higher than background signal) were considered as true signals (grey bars); otherwise a false signal was called (black bars). All measurements were performed in triplicate, and the data are displayed as mean±s.d.

All logic gate configurations and components were summarized in FIG. 15 and Table 5, respectively. Briefly, we used pre-assembled recognition nanostructures to demonstrate the AND, OR, NOT, NAND and NOR functions. In constructing the different gates, we varied the combinations of recognition nanostructures used as well as the ratio of components in each hybrid nanostructure (i.e., DNA aptamer: DNA inverter: Taq polymerase) to program distinct computational functions. Specifically, to prepare the AND gate, two recognition nanostructures were used and each had its components mixed at the ratio (1:1:0.5); the OR gate—two structures (1:1:1); the NOT gate—one structure (1:0:1); the NAND gate—two structures (1:0:1); and NOR gate—two structures (1:0:0.5). All recognition nanostructures were pre-assembled as described previously. The universal signaling nanostructure was used commonly in all logic gates. We tested the gate configurations with different combinations of DNA targets, as described in the truth tables, and compared the enVision signals with the expected outputs. Signals were normalized as described above. Normalized signals above the detection threshold (i.e., >3× s.d. of the background signal) were considered as true signals; otherwise a false signal was called.

Cell Culture and DNA Extraction

All human cell lines were obtained from American Type Culture Collection; CaSki (ATCC CRL-1550), SiHa (ATCC HTB-35), HeLa (ATCC CCL-2), PZ-HPV-7 (ATCC CRL2221). CaSki cells were grown in RMPI-1640. SiHa, HeLa, and C33-a in Eagle's Minimal Essential Medium, supplemented with 10% FBS and penicillin-streptomycin (Corning). PZ-HPV-7 in Keratinocyte Serum Free Medium, supplemented with bovine pituitary extract and human recombinant epidermal growth factor (ATCC). All cell lines were tested and free of mycoplasma contamination (MycoAlert® Mycoplasma Detection Kit, Lonza). Genomic DNA was extracted from 80%-90% confluent cell culture using DNeasy Blood & Tissue Kit™ (Qiagen) following the manufacturer's recommended protocol.

Comparison with LAMP

On the same divergent regions of the HPV genome, identified in the section of 'sequence design', we used the automated online LAMP primer design server (PrimerExplorer.jp) with the default settings [Tomita, N., et al., Nat Protoc 3: 877-882 (2008)] to identify possible LAMP amplification primers. We compared the number of LAMP primer sets, as returned by the software, to the number of enVision recognition nanostructures that could be designed in the same region. For subsequent functionality test, we further compared the performance of the top-ranked LAMP primer sets with the enVision system. For each LAMP amplification, we used 0.2 µM of each primer in the primer set and 100 ng of purified genomic DNA extracted from cell lines of known HPV infections. This mixture was incubated with 8 units of Bst 2.0 DNA polymerase (New England Biolabs) in 1× isothermal amplification buffer II, 6 mM $MgSO_4$, 2.5 mM dNTPs, at 70° C. for 1 hour. The amplification product was purified via PCR cleanup spin columns (New England Biolabs) and quantified through gel electrophoresis.

Clinical Sample Processing

Endocervcial brush samples, fixed in BD SurePath™ liquid-based Pap test solution, were collected from 35 individuals. We used the QIAamp® DNA FFPE Tissue Kit (Qiagen) with a modified protocol to extract DNA from these clinical samples. Briefly, the samples were mixed with 2.5 ml sterile PBS buffer, 2.5 ml buffer ATL, and 80 µl Proteinase K to cover the brushes, and incubated at 56° C. Following this incubation, the liquid was collected and incubated at 90° C. for 1 hour. 3.5 ml buffer AL and 3.5 ml 100% ethanol was added to the sample. This mixture was passed through the extraction column, and washed sequentially with 500 µl of buffer AW1 and buffer AW2. The column was finally dried through centrifugation and the DNA sample was eluted in 50 µl of buffer ATE. The extracted genomic DNA was used directly in the assay as described in 'operation of enVision platform' or processed as described in 'asymmetric amplification', only in cases of residual leftover clinical samples. For all clinical samples, we determined the quality of the extracted DNA through Taqman® PCR analysis of GAPDH housekeeping gene (Applied Biosystems). All clinical measurements were performed in an anonymized and blinded fashion.

Gel Electrophoresis

DNA samples were diluted with appropriate amounts of 6× loading dye (Thermo Fisher) and run on an 8% polyacrylamide gel with TAE buffer (Thermo Scientific) at 100 V. The gel was stained with SYBR® Green I at 10,000× dilution in TAE buffer for 5 minutes before being visualized in a gel imager (Bio-Rad). Intensity and area (volume) of the resulting bands were calculated using ImageLab's in-built algorithms (Bio-Rad).

Statistical Analysis

All measurements were performed in triplicates, and the data displayed as mean±standard deviation. All significance tests were performed via a two-tailed Student's t test. For inter-sample comparisons, multiple pairs of samples were each tested, and the resulting P values were adjusted for multiple hypothesis testing using Bonferroni correction. Values that had an adjusted P<0.05 were determined as significant. Receiver operating characteristic (ROC) curves for the clinical study were generated from patient profiling data and constructed by plotting sensitivity versus (1−specificity), and the values of area under the curve (AUC) were computed using the trapezoidal rule. We used the clinical reports (i.e., Cobas HPV) as classifiers (true positives and true negatives). The optimal threshold for each marker was established from the point closest to the top-left part (perfect sensitivity or specificity) of the corresponding ROC curve. Detection sensitivity, specificity and accuracy were calculated using standard formulas. Statistical analysis was performed using the R-package (version 3.4.2).

Example 2 enVision Platform

The enVision platform consists of a series of enzyme-assisted DNA nanostructures to achieve three functional steps: DNA target recognition, target-independent signal enhancement, and visual detection (FIG. 1a). With orthogonal sequence design of the nanostructures, the target recognition is decoupled from the signal enhancement. In the recognition step, the recognition element is a unique hybrid nanostructure. It consists of a modified DNA aptamer [Dang, C. & Jayasena, S. D. *J Mol Biol* 264: 268-278 (1996); Park, K. S. et al. *Sci Adv* 2: el 600300 (2016)] bound to a Taq DNA polymerase. In the absence of target DNA, the aptamer binds strongly with the polymerase to inhibit polymerase activity. In the presence of complementary target DNA, upon target hybridization, the hybrid dissociates to activate polymerase activity. In the signaling step, the active polymerase elongates a universal, self-priming nanostructure, in a target-independent manner. Through the incorporation of modified oligonucleotides having (dNTPs) to immobilize horseradish peroxidase (HRP) into the signaling structures, visual signals can be enzymatically produced for detection by the naked eye and are readily quantified through smartphones. The insert (FIG. 1a, right) shows an example of the actual assay output as imaged by smartphones.

Figure 6:
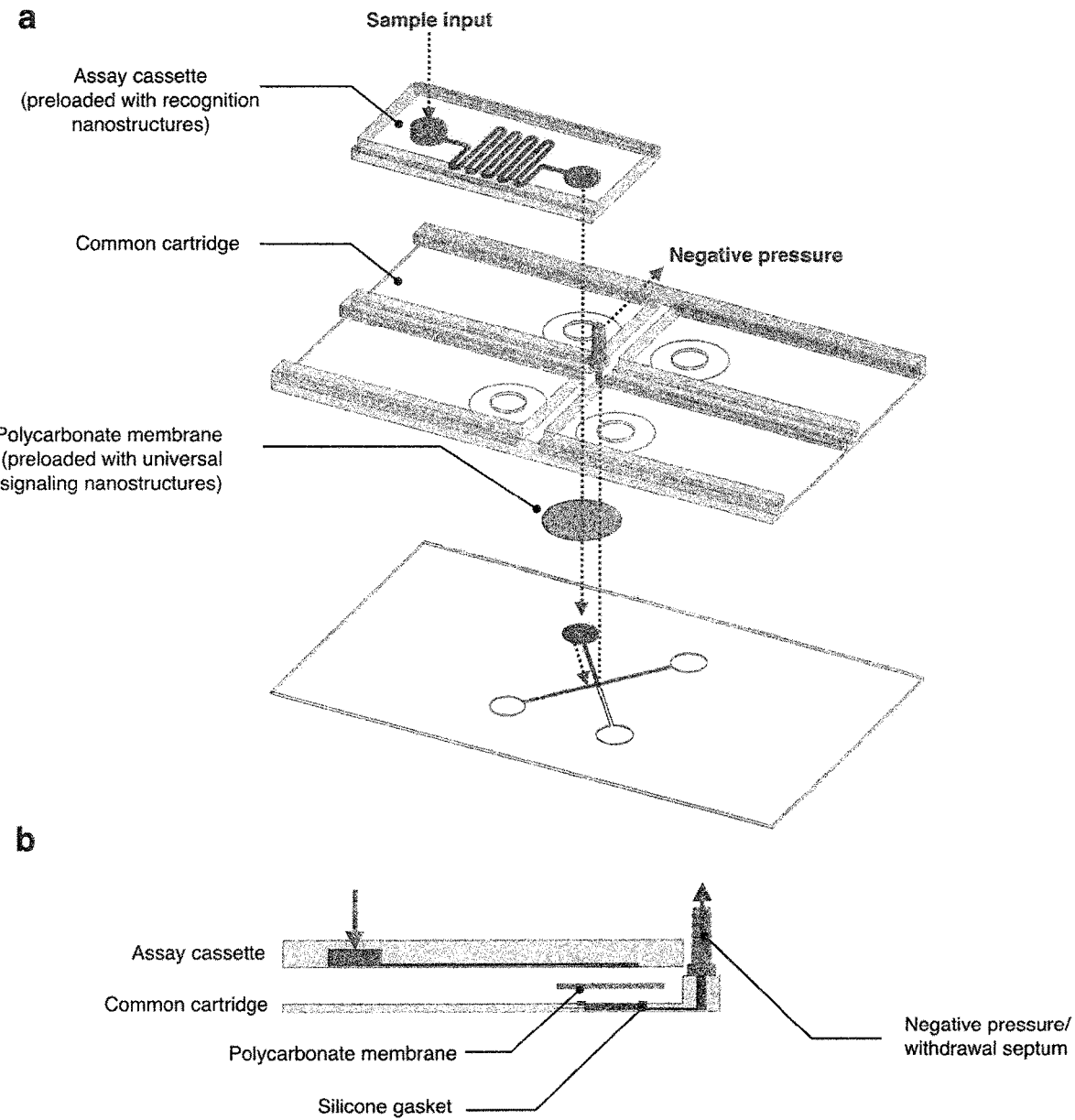
FIG. 6 shows schematics of the enVision microfluidic platform. (a) Exploded schematic and (b) sectional side view of the platform. The platform comprises unique assay cassettes and a common signaling cartridge. Each assay cassette is preloaded with unique recognition nanostructures and contains a serpentine microchannel to improve mixing. Polycarbonate membranes are embedded in the common cartridge to immobilize the signaling nanostructures. Fluidic flow from the sample inlet to the common outlet, actuated by withdrawal septum, is indicated by arrows.

To complement the detection programmability and modularity of the enVision assay a configurable microfluidic platform was implemented which could hold, for example, 4 assay cassettes (FIG. 1b). Specifically, two components were integrated: (i) independent assay cassettes, and (ii) a common signaling cartridge. Each assay cassette was preloaded with specific DNA recognition nanostructures, and could be plugged in on-demand to enable versatile assay integration. The common holder cartridge housed the universal signaling elements, which were immobilized on polycarbonate membranes, for target-independent signaling and visual detection. Fluid flow and sample mixing were performed through a parallel circuit of microchannels (FIG. 6) and actuated by negative pressure at a common outlet on the cartridge to streamline the assay procedure (FIG. 7). FIG. 1c shows a prototype device developed for clinical detection of pathogen DNA targets. This system compartmentalization improves the assay modularity (i.e., on-demand integration) and simplifies the implementation (i.e., uniform surface immobilization and single flow actuation) [Shao, H. et al. *Nat Commun* 6: 6999 (2015)] for clinical applications.

Example 3

Optimized Assay for Visual Quantification of Nucleic Acids

Figure 2:
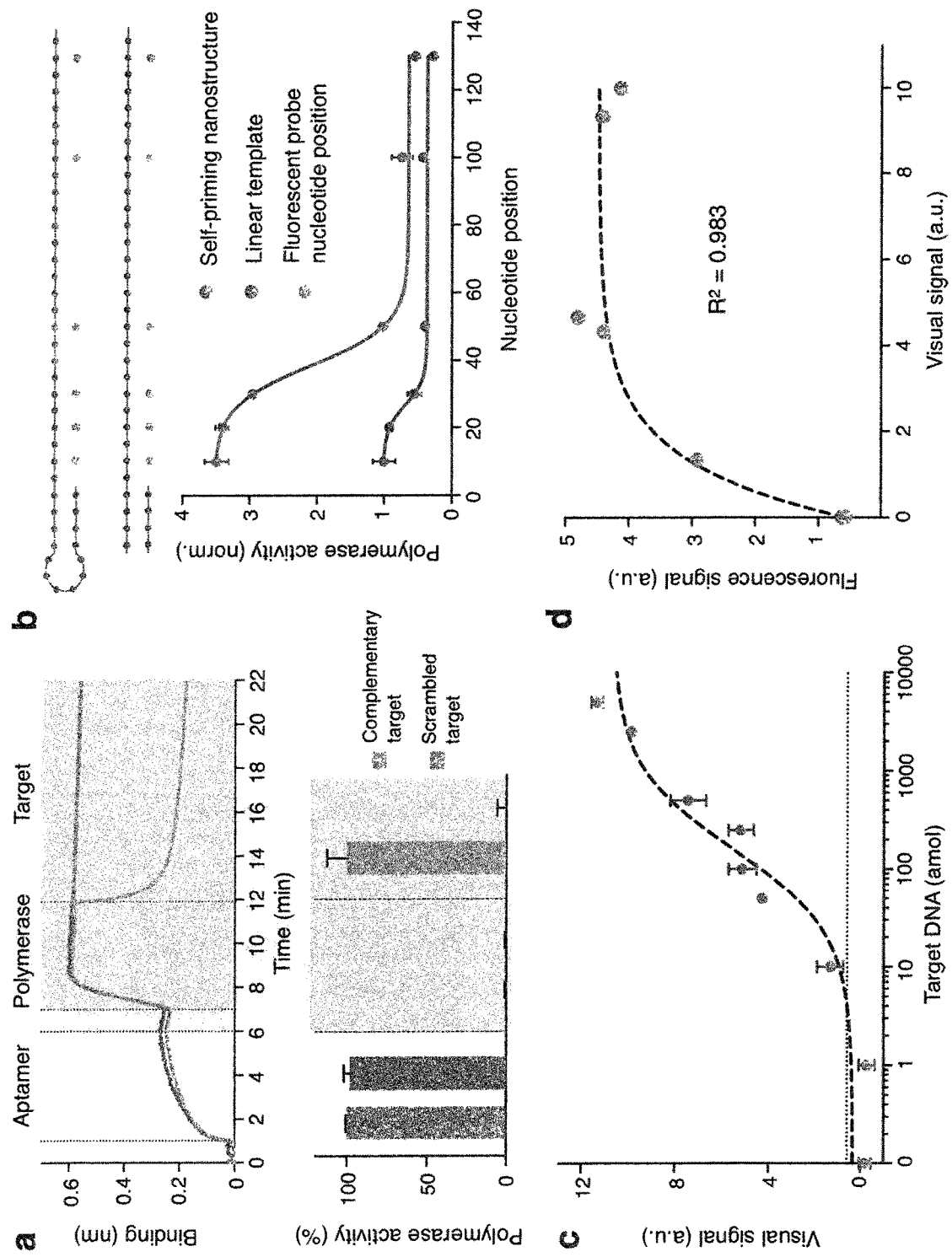
FIG. 2 shows nucleic acid quantification with enVision. (a) Recognition nanostructure assembly and activity. The recognition nanostructure was assembled and incubated with complementary or scrambled target DNA sequences, to determine the resultant polymerase association and activity. (Top) Real-time sensorgram of molecular binding. A series of operations was performed, namely aptamer immobilization, addition of polymerase, and incubation with target DNA sequences. Molecular binding was monitored in situ through bio-layer interferometry to determine polymerase association. (Bottom) The corresponding polymerase activity was determined at the end of each operation via a parallel experiment using a Taqman assay (fluorescence measurement of 5' exonuclease degradation of Taqman probes). Note the complete recovery of polymerase activity upon incubating with complementary target DNA. (b) Signaling nanostructure activity. In a comparative experiment, the self-priming signaling nanostructure and its similarly-sized linear template were treated with equal concentration of active DNA polymerase. The polymerase activity was determined at different nucleotide positions away from the starting primed sites, through 5' exonuclease degradation of differentially placed Taqman probes (positions indicated as grey dots with black centres). (c) Detection sensitivity of the enVision system. The detection limit (dotted line) was determined by titrating a known amount of target DNA and measuring their associated visual signals. All visual signals were acquired through a smartphone. (d) Correlation between enVision and fluorescence measurements on varying quantities of target DNA. The visual signal matched well with the fluorescence signal ($R^2$=0.9828) and demonstrated a wider dynamic range. All measurements were performed in triplicate, and the data are displayed as mean±s.d. a.u.=arbitrary unit.
Figure 8:
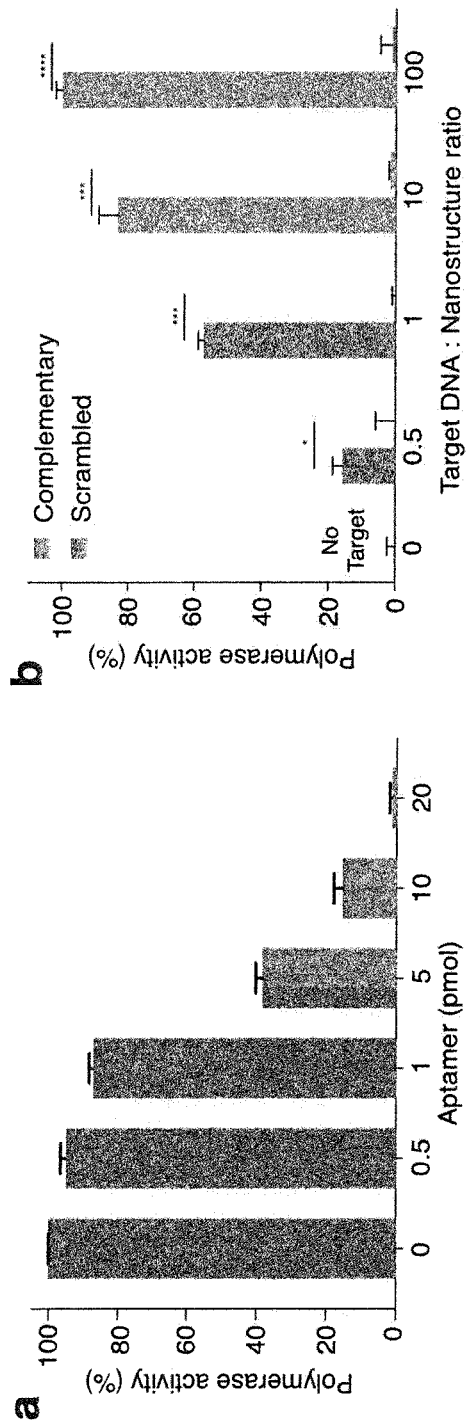
FIG. 8 shows activity of the recognition nanostructure. (a) A varying amount of inhibitory aptamer was added to a fixed amount of polymerase (5 units) to determine the optimal ratio to complex the recognition nanostructure while maximizing the inhibitory effect. (b) To the optimized nanostructure complex, we incubated different amounts of complementary DNA target as well as scrambled oligonucleotide sequence as a control. Note that only complementary target resulted in strong and proportional increase in polymerase activity (bars), while the scrambled oligonucleotide sequence produced negligible activity (at baseline) (*$P<0.05$, *$P<0.0005$, ** $P<0.00005$, Student's t test). All measurements were performed in triplicate, and the data are displayed as mean±s.d.

The performance of the DNA nanostructures as functional recognition and signaling elements, respectively, were evaluated. For the recognition nanostructure, the polymerase associated with the modified aptamer to form a hybrid complex (FIG. 2a, top). This optimized complex demonstrated negligible polymerase activity (FIG. 8a). In the presence of complementary target DNA, the hybrid structure dissociated and the polymerase activity recovered fully (FIG. 2a, bottom). We found that this recognition and activation showed a high sequence specificity, as only complementary targets resulted in strong polymerase activity, while scrambled oligonucleotide sequences produced negligible activity (FIG. 8b).

Figure 9:
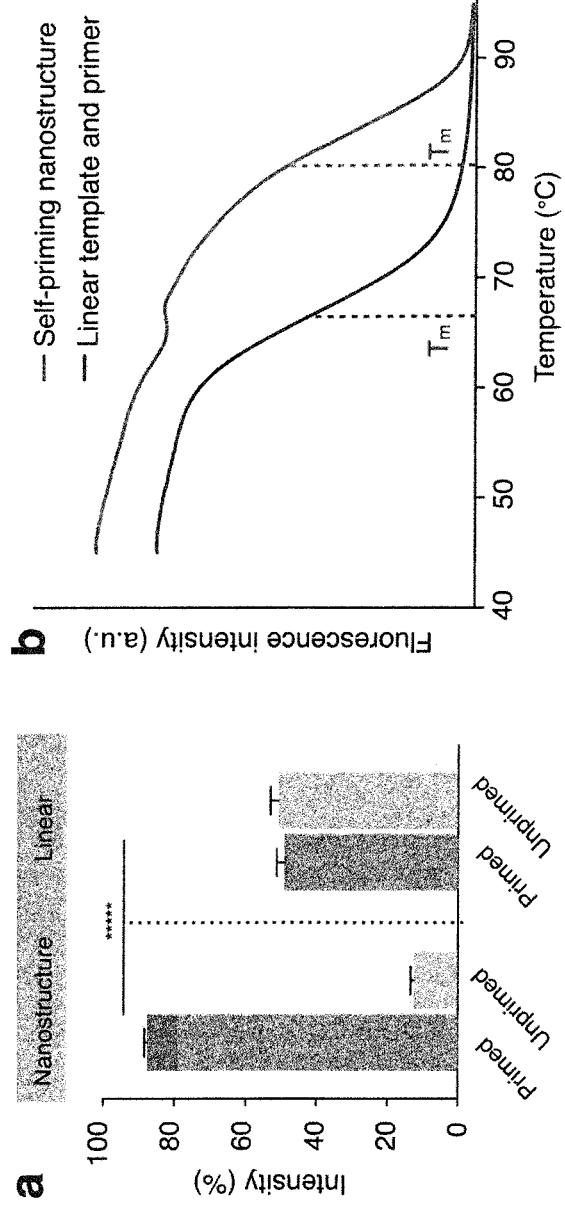
FIG. 9 shows annealing of the signaling nanostructure. (a) The hairpin signaling nanostructure and its equivalent-sized linear counterpart (with excess primers) were resolved through 8% native gel electrophoresis at room temperature. The band intensities of the primed and unprimed fractions in each sample were analyzed (***** $P<0.000005$, Student's t test). (b) Melting curve analysis of the self-priming signaling nanostructure and its linear counterpart. SYBR® green fluorescence intensities were recorded with increasing reaction temperature to assess the dissociation characteristics of double-stranded DNA. Dotted lines indicate the observed melting temperatures (Tm) of the respective nucleic acids. The nanostructure showed a higher Tm as compared to its linear counterpart (with excess primers). All measurements were performed in triplicate, and the data are displayed as mean±s.d in (a).

We further designed the universal recognition element as a self-priming nanostructure. Compared to its similarly-sized linear counterpart, the structure demonstrated enhanced polymerase occupancy and activity (FIG. 2b), possibly due to its superior priming efficiency at room temperature (FIG. 9). All sequences used to optimize the assembly and characterization of the nanostructures can be found in Table 1.

TABLE 1

Oligonucleotides used for activity and sensitivity characterization.

Nanostructure characterization oligonucleotides

Recognition nanostructure characterization

| | |
|---|---|
| Aptamer | AAGTATCTGTAATAAAGTCACAATGTACAGTATTG (SEQ ID NO: 1) |
| Inverter | TGACTTTATTACAGATACTTCTACAACCCCGGTACCATCT (SEQ ID NO: 2) |
| Complementary target | AGATGGTACCGGGGTTGTAGAAGTATCTGTAATAAAGTCA (SEQ ID NO: 3) |
| Scrambled target | AGTAGAACGCGATGGTACAGGCACTGCAGGGTCCATGTCA (SEQ ID NO: 4) |

TABLE 1-continued

Oligonucleotides used for activity and sensitivity characterization.

Signaling nanostructure characterization

| | |
|---|---|
| Self-priming template | AGCAGGCAGTTACGGGCTGGTGCGATGAGAGACGCGGAGTGTGGCGGCCGGATAGTAATGACTGCGA CCGGTGTACCAGTGGCGTGAGGCAGGTCGTGAGGCGGCGTACGTAGAGCGTTGAGCAGGATGCCAAC AGTCGATCAGGACGAGTGCTAACGCATTGTCGATAGCTCAGCTGTCTGAGCTATCGACAATGCGTT (SEQ ID NO: 5) |
| Linear template | AGCAGGCAGTTACGGGCTGGTGCGATGAGAGACGCGGAGTGTGGCGGCCGGATAGTAATGACTGCGA CCGGTGTACCAGTGGCGTGAGGCAGGTCGTGAGGCGGCGTACGTAGAGCGTTGAGCAGGATGCCAAC AGTCGATCAGGACGAGTGCTAACGCATTGTCGATAGCTCA (SEQ ID NO: 6) |
| Linear template primer | TGAGCTATCGACAATGCGTT (SEQ ID NO: 7) |
| 10 bp Taqman® Probe* | /56-FAM/CTGATCGAC/ZEN/TGTTGGCATCC/3IABkFQ/ (SEQ ID NO: 8) |
| 20 bp Taqman® Probe* | /56-FAM/TTGGCATCC/ZEN/TGCTCAACGCT/3IABkFQ/ (SEQ ID NO: 9) |
| 30 bp Taqman® Probe* | /56-FAM/TGCTCAACG/ZEN/CTCTACGTACG/3IABkFQ/ (SEQ ID NO: 10) |
| 50 bp Taqman® Probe* | /56-FAM/GCCGCCTCAC/ZEN/GACCTGCCTC/3IABkFQ/ (SEQ ID NO: 11) |
| 100 bp Taqman® Probe* | /56-FAM/TATCCGGCC/ZEN/GCCACACTCCG/3IABkFQ/ (SEQ ID NO: 12) |
| 130 bp Taqman® Probe* | /56-FAM/CGCACCAGC/ZEN/CCGTAACTGCC/3IABkFQ/ (SEQ ID NO: 13) |
| 5' amine universal signaling nanostructure | /5AmMC12/GCGGCGTACGTAGAGCGTTGAGCAGGATGCCAACAGTCGATCAGGACGAGTGCTAACG CATTGTCGATAGCTCAGCTGTCTGAGCTATCGACAATGCGTT (SEQ ID NO: 14) |

Mismatch characterization

| | |
|---|---|
| Complementary target overhang 2 mismatch | AGATGGTACCGCGGTTGTATAAGTATCTGTAATAAAGTCA (SEQ ID NO: 15) |
| Complementary target overhang 4 mismatch | AGATAGTGCCGCGGTTGTATAAGTATCTGTAATAAAGTCA (SEQ ID NO: 16) |
| Complementary target overhang 6 mismatch | AGATAGTGCAGCGGTTATATAAGTATCTGTAATAAAGTCA (SEQ ID NO: 17) |
| Complementary target overhang 8 mismatch | ACATAGTGCAGCGGCTATATAAGTATCTGTAATAAAGTCA (SEQ ID NO: 18) |
| Complementary target overhang 10 mismatch | ACGTAGTGCAGCAGCTATATAAGTATCTGTAATAAAGTCA (SEQ ID NO: 19) |
| Complementary target overhang 12 mismatch | ACGTAGTGTAGCAGCTATCTAAGTATCTGTAATAAAGTCA (SEQ ID NO: 20) |
| Complementary target duplex 2 mismatch | AGATGGTACCGGGGTTGTAGAATTATCTGTAATAGAGTCA (SEQ ID NO: 21) |
| Complementary target duplex 4 mismatch | AGATGGTACCGGGGTTGTAGAATTAGCTGTACTAGAGTCA (SEQ ID NO: 22) |
| Complementary target duplex 6 mismatch | AGATGGTACCGGGGTTGTAGTATTAGCTCTACTAGAGTCA (SEQ ID NO: 23) |
| Complementary target duplex 8 mismatch | AGATGGTACCGGGGTTGTAGTATTCGCTCTACTAGAGTAA (SEQ ID NO: 24) |
| Complementary target duplex 10 mismatch | AGATGGTACCGGGGTTGTAGTATTCGCTCTACAAGATTAA (SEQ ID NO: 25) |
| Complementary target duplex 12 mismatch | AGATGGTACCGGGGTTGTAGTATTCGCACTACAAGATTAC (SEQ ID NO: 26) |

Target amplification demonstration

Asymmetric Amplification

| | |
|---|---|
| HPV 16 forward primer | ATGGATTATATGATATTTATGC (SEQ ID NO: 27) |
| HPV 16 reverse primer | CTGATAAAGATGTAGAGG (SEQ ID NO: 28) |
| HPV 16 product | CTGATAAAGATGTAGAGGGTACAGATGGTACCGGGGTTGTAGAAGTATCTGTAATAAAGTCATCTGC ATAAATATCATATAATCCAT (SEQ ID NO: 29) |

NASBA

| | |
|---|---|
| HPV 16 NASBA forward primer | AATTCTAATACGACTCACTATAGGGAGAAGGGCAGCCTCACCTACTTCTATTA (SEQ ID NO: 30) |
| HPV 16 NASBA reverse primer | AAAGATGTAGAGGGTACAGA (SEQ ID NO: 31) |
| HPV 16 NASBA product | GCAGCCTCACCTACTTCTATTAATAATGGATTATATGATATTTATGCAGATGACTTTATTACAGATA CTTCTACAACCCCGGTACCATCTGTACCCTCTACATCTTT (SEQ ID NO: 32) |

*Taqman® probes are listed in the sequence listing without the FAM/ZEN markers.

Figure 10:
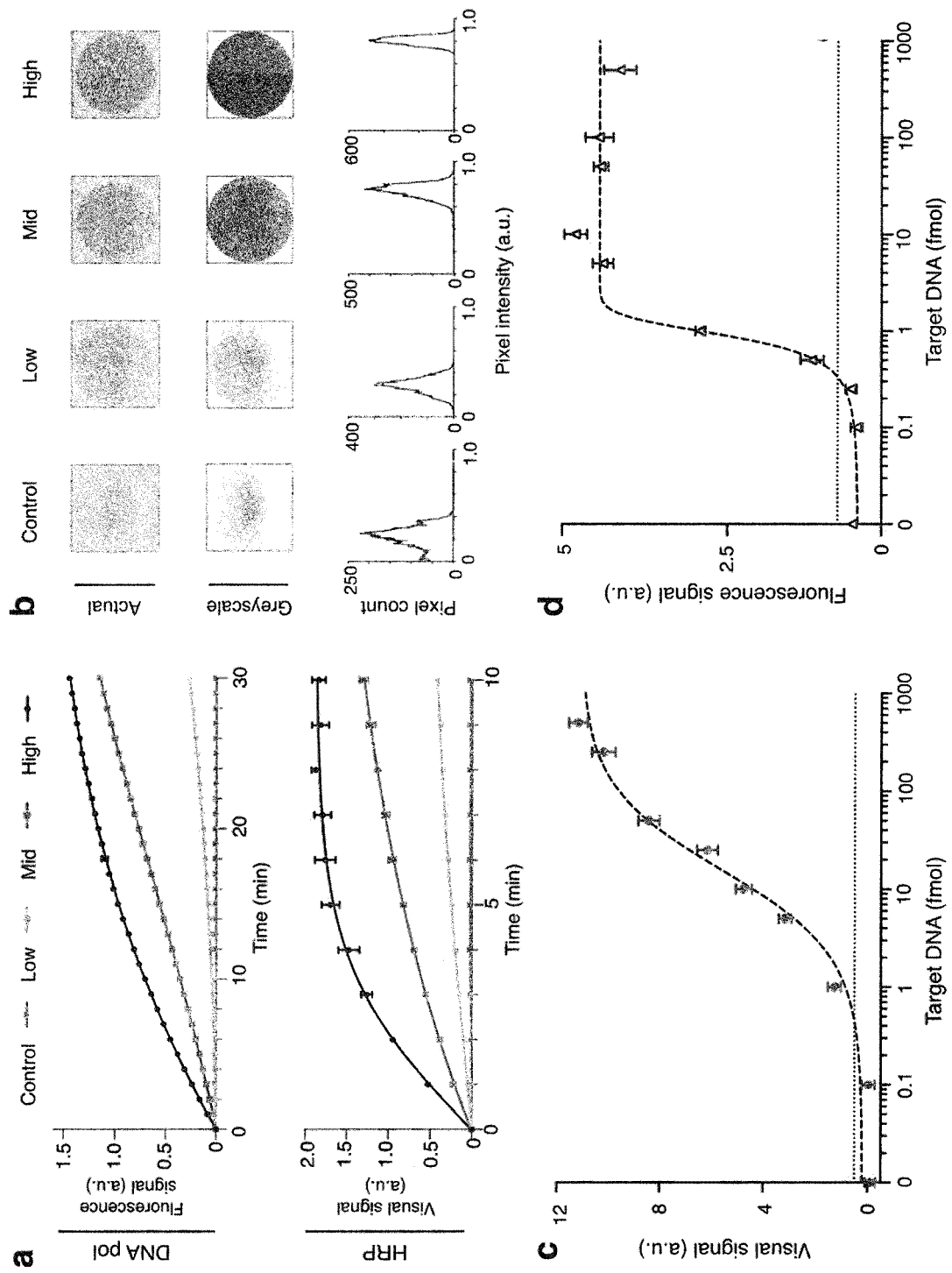
FIG. 10 shows visual and fluorescence readouts. (a) Optimization of enzyme reactions. We measured the real-time activities of DNA polymerase (DNA pol, top) and HRP (bottom), in the presence of control (water) and varying amounts of DNA targets. Polymerase activity was determined via a Taqman® assay (fluorescence measurement of 5' exonuclease degradation of Taqman® probes), while HRP activity was determined via smartphone intensity measurement. Polymerase activity corresponds to Steps 1-3 in the device operation and HRP activity corresponds to Step 4 (see FIG. 7). The optimized durations for these enzyme reactions were thus determined at ~20 min and 3 min, respectively. (b) Example images of enVision readouts (top), after image conversion to greyscale (middle) and the distribution of greyscale pixel intensities (bottom). The mean pixel intensity of each spot image was used for signal quantification and normalization. (c) Visual detection sensitivity of the enVision system. The detection limit (dotted line) was determined by directly titrating a known amount of target DNA (without asymmetric amplification) and measuring their associated visual signals through the enVision platform at room temperature. All visual signals were acquired through a smartphone. (d) Fluorescence detection sensitivity. The detection limit (dotted line) was determined by directly titrating a known amount of target DNA with the recognition nanostructure. The polymerase activity was measured via its 5' exonuclease degradation of fluorescent Taqman® probes. All fluorescence signals were acquired though a commercial qPCR fluorescence detector. All measurements were performed in triplicate, and the data are displayed as mean±s.d. a.u., arbitrary unit.

To enable visual detection, the activated polymerase was used to elongate the signaling nanostructure and incorporate horseradish peroxidase (HRP) through biotinylated nucleotides (biotin-16-AA-dCTP). In the presence of optical substrate, the HRP activity developed brown precipitates rapidly. In a titration analysis, the observed color intensity could be correlated to increasing amounts of target DNA. When imaged with a smartphone camera, the visual assay demonstrated a limit of detection (LOD) of 0.260 fmol of target DNA (FIG. 10c) and the assay could be completed in as little as 30 minutes at room temperature. The LOD could be further improved to 7.205 amol of target DNA (FIG. 2c) through integration with efficient asymmetric amplification (FIG. 11). Isothermal asymmetric amplification through nucleic acid sequence based amplification (NASBA) [Pardee, K. et al. Cell 165: 1255-1266 (2016)] could also be incorporated to improve practical applications (FIG. 12). All primers and targets used for amplification can be found in Table 1. Detection sensitivities were determined with point-of-care smartphone readouts; all processes (including asymmetric amplification and NASBA) were accomplished in <2 hours. To correlate the visual signal with standard fluorescence signal, we performed a similar experiment with FAM-modified nucleotides (FIG. 10d). The enVision visual assay correlated well to a logistic function that accounts for fluorescence signal saturation ($R^2$=0.983) (FIG. 2d). When compared to the fluorescence measurements, which saturated at high concentrations of DNA targets, the enVision platform showed a wider dynamic range to produce distinguishable and quantifiable visual signals at these target concentrations. We attribute this expansion in the visual dynamic range to the incorporation of dual enzymatic signaling (i.e., DNA polymerase and HRP cascades) in the enVision technology.

Example 4

Programmability of enVision

To design assays for visual detection of nucleic acids, we investigated the programmability of the recognition nanostructure. The hybrid structure consists of a conserved sequence region that folds to bind and inhibit DNA polymerase, and a variable region (i.e., duplex and overhang segments) that can be made complementary to target DNA (FIG. 3a). By inducing mismatches between the variable region of the recognition nanostructure and the target DNA, we identified that the duplex region showed a higher sensitivity to sequence mismatches, as compared to the overhang region (FIG. 3b). Thus the duplex region could confer strong sequence specificity, while the overhang region could accommodate more sequence variability, a feature useful for pan-detection.

This design principle was validated by developing two pan-HPV recognition nanostructures (FIG. 3c). The structures were designed by matching against the HPV consensus genome, and contained varying number of mismatches against DNA targets from six HPV subtypes (Table 2). By mapping all the mismatched regions, we found that Pan-HPV Nanostructure 1 which accommodated more mismatches in the overhang region demonstrated better pan-detection capability of the consensus genome. Pan-HPV Nanostructure 2 which contained more mismatches in the duplex region showed a reduced signal in general, indicating the importance of the duplex region in conferring assay specificity.

Next, we designed specific nanostructures for HPV subtyping. We identified a highly variable region of the HPV genome to design a new group of recognition nanostructures for specific differentiation of HPV subtypes (i.e. HPV 6, 11, 16, 18, 31, 33, 58, and 66) (FIG. 3d, left); sequence variability was designed to be contained within the sensitive duplex region. As compared to conventional qPCR analysis, which requires a pair of primers for target amplification and detection, the enVision recognition nanostructure could be easily adapted, as its specificity is determined by a single probe sequence (i.e., the variable region). We used this programmability to rapidly design new specific HPV subtyping nanostructures (Table 2) and integrated them with the enVision technology.

TABLE 2

Nanostructures for HPV pan-detection and specific subtyping.

Pan-HPV nanostructure 1

| | |
|---|---|
| Aptamer | TTTAAATAATCTGGATATTTCAATGTACAGTATTG (SEQ ID NO: 33) |
| Inverter | AAATATCCAGATTATTTAAAAATGGCTGCA (SEQ ID NO: 34) |
| Complementary positive target | CATAAGGATCTGCAGCCATTTTTAAATAATCTGGATATTT (SEQ ID NO: 35) |
| HPV 06 Target | CATATGGGTCTGCAGCCATTTGTAAATAATCTGGATATTT (SEQ ID NO: 36) |
| HPV 16 Target | CATATGGTTCTGACACCATTTTAATATAATCTGGATATTT (SEQ ID NO: 37) |
| HPV 18 Target | CATAAGGATCTGCAGACATTTGTAAATAATCAGGATATTT (SEQ ID NO: 38) |
| HPV 31 Target | CATATGGCTCAGCAACCATTTTAAGATAATCTGGATATTT (SEQ ID NO: 39) |
| HPV 33 Target | CATATGGCTCAGCAACCATTTTAAGATAATCTGGATATTT (SEQ ID NO: 40) |
| HPV 58 Target | CATAAGGTTCACTGGCCATTTTTAAATAATCTGGATATTT (SEQ ID NO: 41) |

Pan-HPV nanostructure 2

| | |
|---|---|
| Aptamer | AAATAATTGTGCCTCAGAGGCAATGTACAGTATTG (SEQ ID NO: 42) |
| Inverter | CCTCTGAGGCACAATTATTTAATAAACCATATTGGCTACA (SEQ ID NO: 43) |
| Complementary positive target | TGTAGCCAATATGGTTTATTAAATAATTGTGCCTCAGAGG (SEQ ID NO: 44) |
| HPV 06 Target | TGTAGCCAATATGGCTTATTAAACAATTGTGCCTCAGAGG (SEQ ID NO: 45) |
| HPV 16 Target | TGTAACCAATAAGGTTTATTGAATATTTGGGCATCAGAGG (SEQ ID NO: 46) |
| HPV 18 Target | TGTAACCAATATGGTTTATTAAACAACTGGGAGTCAGAGG (SEQ ID NO: 47) |

TABLE 2-continued

Nanostructures for HPV pan-detection and specific subtyping.

| | | |
|---|---|---|
| HPV 31 Target | TGCATCCAATATGGTTTATTAAAAATTTGTGCATCTGAAG | (SEQ ID NO: 48) |
| HPV 33 Target | TGTAGCCAATATGGCTTATTAAATAACTGAGATTCGGAAG | (SEQ ID NO: 49) |
| HPV 58 Target | TGTAGCCAATAAGGCTTATTAAATAATTGTGATTCTGAGG | (SEQ ID NO: 50) |

HPV subtyping

| | | |
|---|---|---|
| HPV 06 aptamer | TAATGTCAGGTTCAAAAGATCAATGTACAGTATTG | (SEQ ID NO: 51) |
| HPV 06 inverter | ATCTTTTGAACCTGACATTAACCCTACCCAACACCCTGTT | (SEQ ID NO: 52) |
| HPV 06 target | AACAGGGTGTTGGGTAGGGTTAATGTCAGGTTCAAAAGAT | (SEQ ID NO: 53) |
| HPV 11 aptamer | CAGGGATAGGGTCAAATGGTCAATGTACAGTATTG | (SEQ ID NO: 54) |
| HPV 11 inverter | ACCATTTGACCCTATCCCTGACCCTGTCCAACATTCTGTT | (SEQ ID NO: 55) |
| HPV 11 target | AACAGAATGTTGGACAGGGTCAGGGATAGGGTCAAATGGT | (SEQ ID NO: 56) |
| HPV 16 aptamer | AAGTATCTGTAATAAAGTCACAATGTACAGTATTG | (SEQ ID NO: 57) |
| HPV 16 inverter | TGACTTTATTACAGATACTTCTACAACCCCGGTACCATCT | (SEQ ID NO: 58) |
| HPV 16 target | AGATGGTACCGGGGTTGTAGAAGTATCTGTAATAAAGTCA | (SEQ ID NO: 59) |
| HPV 18 aptamer | GCACTGCAGGGTCCATGTCACAATGTACAGTATTG | (SEQ ID NO: 60) |
| HPV 18 inverter | TGACATGGACCCTGCAGTGCCTGTACCATCGCGTTCTACT | (SEQ ID NO: 61) |
| HPV 18 target | AGTAGAACGCGATGGTACAGGCACTGCAGGGTCCATGTCA | (SEQ ID NO: 62) |
| HPV 31 aptamer | TATCCACAGTAAAATCAGTGCAATGTACAGTATTG | (SEQ ID NO: 63) |
| HPV 31 inverter | CACTGATTTTACTGTGGATACACCTGCCACACATAATGTT | (SEQ ID NO: 64) |
| HPV 31 target | AACATTATGTGTGGCAGGTGTATCCACAGTAAAATCAGTG | (SEQ ID NO: 65) |
| HPV 33 aptamer | TGTGTACATTATCCACATCGCAATGTACAGTATTG | (SEQ ID NO: 66) |
| HPV 33 inverter | CGATGTGGATAATGTACACACCCCAATGCAACACTCATAC | (SEQ ID NO: 67) |
| HPV 33 target | GTATGAGTGTTGCATTGGGGTGTGTACATTATCCACATCG | (SEQ ID NO: 68) |
| HPV 58 aptamer | CATGTATAGTATCAGCATCGCAATGTACAGTATTG | (SEQ ID NO: 69) |
| HPV 58 inverter | CGATGCTGATACTATACATGATTTTCGAGATCCTCTGCAC | (SEQ ID NO: 70) |
| HPV 58 target | GTGCAGAGGACTCTGAAAATCATGTATAGTATCAGCATCG | (SEQ ID NO: 71) |
| HPV 66 aptamer | TGGGTGCCTCATCATCAATACAATGTACAGTATTG | (SEQ ID NO: 72) |
| HPV 66 inverter | TATTGATGATGAGGCACCCATTTCATTTCGTCAGTCTGGT | (SEQ ID NO: 73) |
| HPV 66 target | ACCAGACTGACGAAATGAAATGGGTGCCTCATCATCAATA | (SEQ ID NO: 74) |

Figure 13:
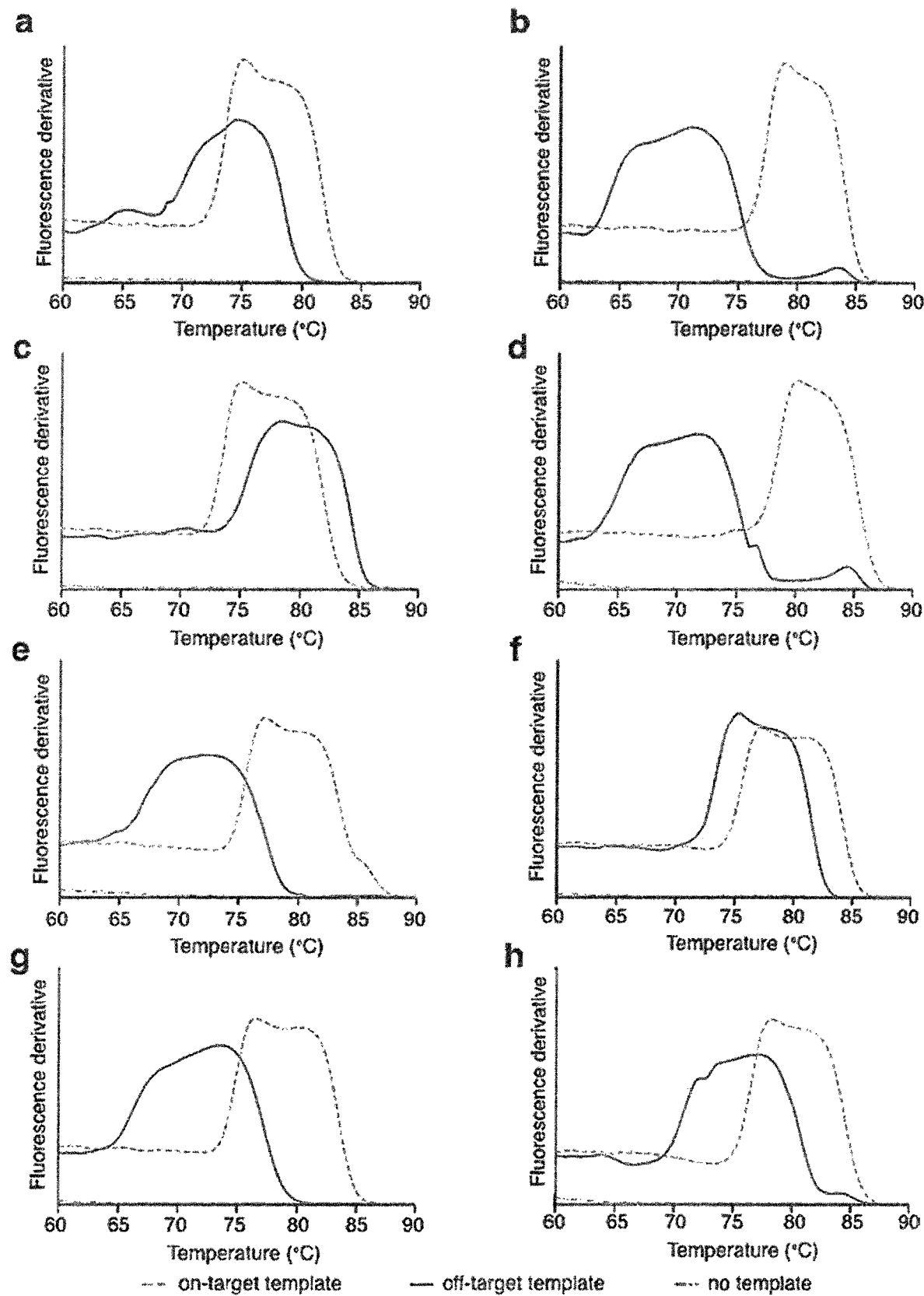
FIG. 13 shows melting curve analysis of SYBR® Green qPCR reactions. Melting curves for primer pairs of (a) HPV 6, (b) HPV 11, (c) HPV 16, (d) HPV 18, (e) HPV 31, (f) HPV 33, (g) HPV 58, and (h) HPV 66 sequences. Each primer set was tested against target template (dashed line), off-target template from other HPV subtypes (solid line), or no template control (water, dash-dot line). All measurements were performed in triplicate, and displayed as line plots of the mean fluorescence intensities.
Figure 14:
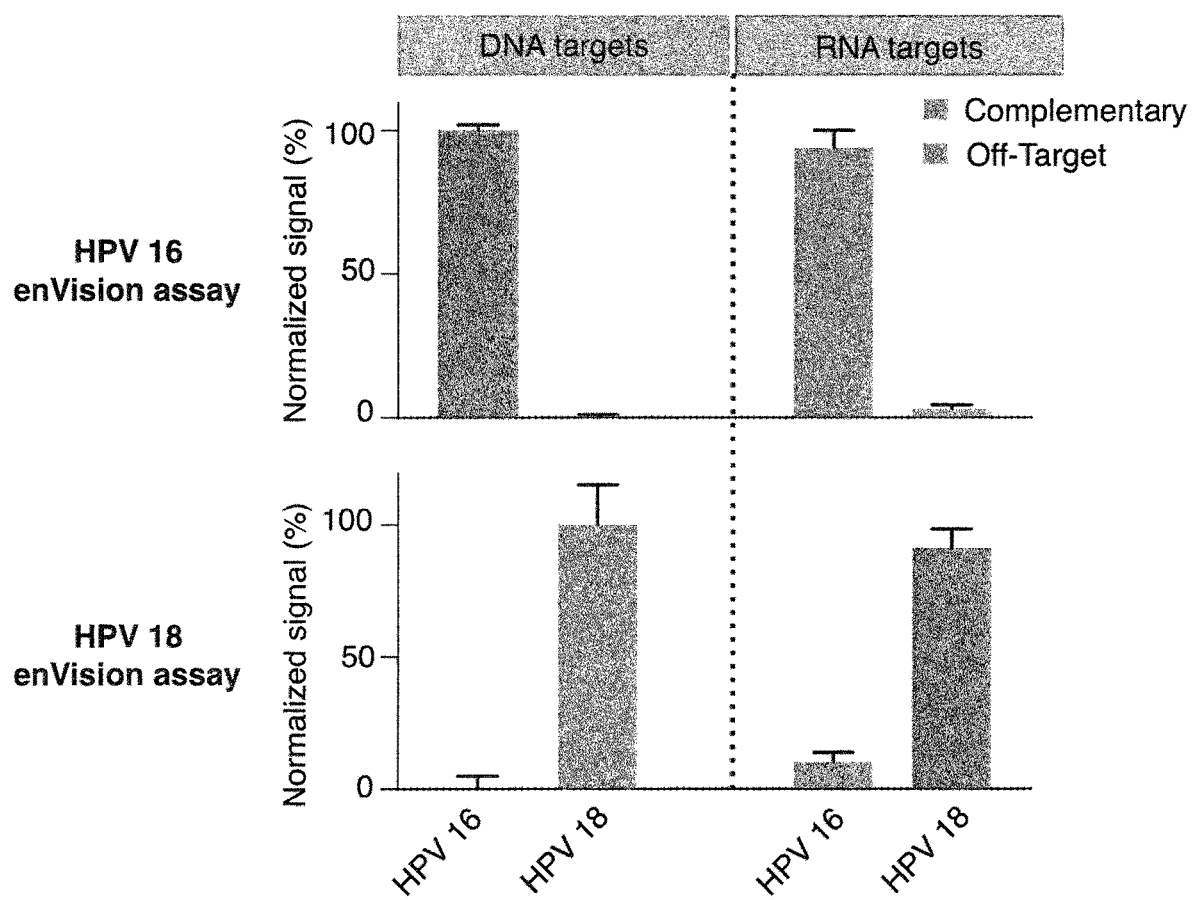
FIG. 14 shows direct RNA detection. We tested the developed enVision assays (i.e., HPV 16 and HPV 18 assays) for direct detection of DNA (left) and RNA (right) of different HPV subtypes. All RNA targets were used directly without any cDNA conversion. Targets were considered as either complementary or off-target. The enVision assays demonstrated specific and direct detection of RNA targets, with signals comparable to that of DNA targets whilst off-target signals were near baseline for both. All signals were normalized against each assay's positive DNA signal for relative comparison. All measurements were performed in triplicate, and the data are displayed as mean±s.d.

In a comparative analysis where we designed PCR primers to detect the same HPV DNA targets (Table 3), the enVision platform demonstrated better specificity (FIG. 3d, left), while the SYBR® Green-based qPCR yielded more false positives (FIG. 3d, right), likely due to non-specific amplification in the qPCR analysis (FIG. 13). Importantly, due to differences in the sensing mechanisms (i.e., enVision detects via hybridization-activated signal enhancement and qPCR detects via nucleic acid target amplification), we further demonstrated that the enVision technology could directly distinguish specific HPV RNA targets, without needing any reverse transcription—a prerequisite for qPCR detection of RNA targets to ensure enzyme compatibility (FIG. 14). All sequences used to transcribe the RNA targets can be found in Table 3.

TABLE 3

SYBR ® qPCR primers and RNA templates.

SYBR ® qPCR primers and RNA templates.

| | | |
|---|---|---|
| HPV 06 forward primer | GAAGATACATTTGATATTTATGC | (SEQ ID NO: 75) |
| HPV 06 reverse primer | ATTAGGTGTGGAAGTTAA | (SEQ ID NO: 76) |
| HPV 06 product | GAAGATACATTTGATATTTATGCTGAATCTTTTGAACCTGACATTAACCCTACCCAACAC CCTGTTACAAATATATCAGATACATATTTAA | (SEQ ID NO: 77) |
| HPV 11 forward primer | ACACGTTTGATATTTATGC | (SEQ ID NO: 78) |
| HPV 11 reverse primer | TATTAGGTGTGGAGGTA | (SEQ ID NO: 79) |
| HPV 11 product | ACACGTTTGATATTTATGCTGAACCATTTGACCCTATCCCTGACCCTGTCCAACATTCTG TTACACAGTCTTATCTTACCTCCACACCTAATA | (SEQ ID NO: 80) |
| HPV 16 forward primer | ATGGATTATATGATATTTATGC | (SEQ ID NO: 27) |
| HPV 16 reverse primer | CTGATAAAGATGTAGAGG | (SEQ ID NO: 28) |
| HPV 16 product | CTGATAAAGATGTAGAGGGTACAGATGGTACCGGGGTTGTAGAAGTATCTGTAATAAAGT CATCTGCATAAATATCATATAATCCAT | (SEQ ID NO: 29) |
| HPV 18 forward primer | ACTTGTTTGATATATATGCA | (SEQ ID NO: 81) |
| HPV 18 reverse primer | GCGAATATTTAAAAAATGC | (SEQ ID NO: 82) |
| HPV 18 product | ACTTGTTTGATATATGCAGATGACATGGACCCTGCAGTGCCTGTACCATCGCGTTCTACT ACCTCCTTTGCATTTTTTAAATATTCGC | (SEQ ID NO: 83) |

TABLE 3-continued

SYBR ® Green qPCR primers and RNA templates.

| | |
|---|---|
| HPV 31 forward primer | GGCTTATATGACATTTATGC (SEQ ID NO: 84) |
| HPV 31 reverse primer | ACTGTACAGCAGTAGAA (SEQ ID NO: 85) |
| HPV 31 product | GGCTTATATGACATTTATGACAGACACTGATTTTACTGTGGATACACCTGCCACACATAA TGTTTCCCCTTCTACTGCTGTACAGT (SEQ ID NO: 86) |
| HPV 33 forward primer | GTTTGTATGATGTTTATGC (SEQ ID NO: 87) |
| HPV 33 reverse primer | TTGCAAACGTACTGTAT (SEQ ID NO: 88) |
| HPV 33 product | GTTTGTATGATGTTTATGCTGACGATGTGGATAATGTACACACCCCAATGCAACACTCAT ACAGTACGTTTGCAA (SEQ ID NO: 89) |
| HPV 58 forward primer | TGGACTTTATGATATTTATGC (SEQ ID NO: 90) |
| HPV 58 reverse primer | GCAAAGGACGTATGT (SEQ ID NO: 91) |
| HPV 58 product | TGGACTTTATGATATTTATGCTGACGATGCTGATACTATACATGATTTTCAGAGTCCTCT GCACTCACATACGTCCTTTGC (SEQ ID NO: 92) |
| HPV 66 forward primer | GCCTATATGATATTTATGCA (SEQ ID NO: 93) |
| HPV 66 reverse primer | AGGTAATTGTGCAGAA (SEQ ID NO: 94) |
| HPV 66 product | GCCTATATGATATTTATGCAAATATTGATGATGAGGCACCCATTTCATTTCGTCAGTCTG GTGCTACACCTTCTGCACAATTACCT (SEQ ID NO: 95) |

RNA synthesis templates

| | |
|---|---|
| HPV 16 L2 template | TCTAATACGACTCACTATAGAGATGGTACCGGGGTTGTAGAAGTATCTGTAATAAAGTCA (SEQ ID NO: 96) |
| HPV 16 L2 template complement | TGACTTTATTACAGATACTTCTACAACCCCGGTACCATCTCTATAGTGAGTCGTATTAGA (SEQ ID NO: 97) |
| HPV 18 L2 template | TCTAATACGACTCACTATAGAGTAGAACGCGATGGTACAGGCACTGCAGGGTCCATGTCA (SEQ ID NO: 98) |
| HPV 18 L2 template complement | TGACATGGACCCTGCAGTGCCTGTACCATCGCGTTCTACTCTATAGTGAGTCGTATTAGA (SEQ ID NO: 99) |

Example 5

Multiplexed Assay for Enhanced Detection Coverage

To improve detection coverage, it was next determined whether multiplexed enVision assays could be performed simultaneously in a single chamber. While clinical HPV assays typically detect a single region of the viral genome (the L1 locus) for infection determination, partial viral genome integrations into the host cells are also possible and can lead to cancerous growth [Williams, V. M., et al., *Future Virol* 6: 45-57 (2011); McBride, A. A. & Warburton, A. *PLoS Pathog* 13: e1006211 (2017)]. Using non-conserved regions in the HPV viral genome, various enVision recognition nanostructures were designed to detect the E1, L1 and L2 loci to improve the detection coverage (FIG. 4a; Table 4).

TABLE 4

Nanostructures for multi-loci HPV detection.

HPV 16

| | |
|---|---|
| E1 aptamer | CAACCACCCCCACTTCCACCCAATGTACAGTATTG (SEQ ID NO: 100) |
| E1 inverter | GGTGGAAGTGGGGGTGGTTGCAGTCAGTACAGTAGTGGAA (SEQ ID NO: 101) |
| E1 target | TTCCACTACTGTACTGACTGCAACCACCCCCACTTCCACC (SEQ ID NO: 102) |
| L1 aptamer | GTTTCTGAAGTAGATATGGCCAATGTACAGTATTG (SEQ ID NO: 103) |
| L1 inverter | GCCATATCTACTTCAGAAACTACATATAAAAATACTAACT (SEQ ID NO: 104) |
| L1 target | AGTTAGTATTTTTATATGTAGTTTCTGAAGTAGATATGGC (SEQ ID NO: 105) |
| L2 aptamer | AAGTATCTGTAATAAAGTCACAATGTACAGTATTG (SEQ ID NO: 106) |
| L2 inverter | TGACTTTATTACAGATACTTCTACAACCCCGGTACCATCT (SEQ ID NO: 107) |
| L2 target | AGATGGTACCGGGGTTGTAGAAGTATCTGTAATAAAGTCA (SEQ ID NO: 108) |

HPV 18

| | |
|---|---|
| E1 aptamer | TGTGCCCCCGTTGTCTATAGCAATGTACAGTATTG (SEQ ID NO: 109) |
| E1 inverter | CTATAGACAACGGGGGCACAGAGGGCAACAACAGCAGTGT (SEQ ID NO: 110) |
| E1 target | ACACTGCTGTTGTTGCCCTCTGTGCCCCCGTTGTCTATAG (SEQ ID NO: 111) |
| L1 aptamer | AGGTACAGGAGACTGTGTAGCAATGTACAGTATTG (SEQ ID NO: 112) |
| L1 inverter | CTACACAGTCTCCTGTACCTGGGCAATATGATGCTACCAA (SEQ ID NO: 113) |
| L1 target | TTGGTAGCATCATATTGCCCAGGTACAGGAGACTGTGTAG (SEQ ID NO: 114) |
| L2 aptamer | GCACTGCAGGGTCCATGTCACAATGTACAGTATTG (SEQ ID NO: 115) |
| L2 inverter | TGACATGGACCCTGCAGTGCCTGTACCATCGCGTTCTACT (SEQ ID NO: 116) |
| L2 target | AGTAGAACGCGATGGTACAGGCACTGCAGGGTCCATGTCA (SEQ ID NO: 117) |

TABLE 4-continued

Nanostructures for multi-loci HPV detection.

Taqman ® PCR validation

| | |
|---|---|
| HPV 16 E1 forward primer | CAACGTGTTGCGATTGGTGT (SEQ ID NO: 118) |
| HPV 16 E1 reverse primer | ACCATTCCCCATGAACATGCTA (SEQ ID NO: 119) |
| HPV 16 E1 Taqman ® probe | /56-FAM/ACACCCAGT/ZEN/ATAGCTGACAG/3IABkFQ/ (SEQ ID NO: 120) |
| HPV 16 L1 forward primer | CACCTAATGGCTGACCACGA (SEQ ID NO: 121) |
| HPV 16 L1 reverse primer | ACTTGCAGTTGGACATCCCT (SEQ ID NO: 122) |
| HPV 16 L1 Taqman ® probe | /56-FAM/CACCTACAC/ZEN/AGGCCCAAACC/3IABkFQ/ (SEQ ID NO: 123) |
| HPV 16 L2 forward primer | TTGGAACAGGGTCGGGTACA (SEQ ID NO: 124) |
| HPV 16 L2 reverse primer | GAAGGGCCCACAGGATCTAC (SEQ ID NO: 125) |
| HPV 16 L2 Taqman ® probe | /56-FAM/TGGGAACAA/ZEN/GGCCTCCCACA/3IABkFQ (SEQ ID NO: 126) |

These modular recognition nanostructures could be readily configured into different logic gates (e.g., OR, AND, NOT, NAND and NOR), in a single reaction chamber, to perform programmable computations and enable visual readouts from different combinations of DNA targets (FIG. 15; Table 5). The modular recognition nanostructures can also be readily configured to detect a plurality of targets in the various logic gate configurations (FIG. 16; Table 2)

TABLE 5

Nanostructures for enVision logic gates.

HPV 16 nanostructure sequences

| | |
|---|---|
| HPV 16 aptamer | AAGTATCTGTAATAAAGTCACAATGTACAGTATTG (SEQ ID NO: 57) |
| HPV 16 inverter | TGACTTTATTACAGATACTTCTACAACCCCGGTACCATCT (SEQ ID NO: 58) |
| HPV 16 NOT aptamer | TGACTTTATTACAGATACTTCAATGTACAGTATTG (SEQ ID NO: 127) |
| HPV 16 target | AGATGGTACCGGGGTTGTAGAAGTATCTGTAATAAAGTCA (SEQ ID NO: 59) |

HPV 18 nanostructure sequences

| | |
|---|---|
| HPV 18 aptamer | GCACTGCAGGGTCCATGTCACAATGTACAGTATTG (SEQ ID NO: 60) |
| HPV 18 inverter | TGACATGGACCCTGCAGTGCCTGTACCATCGCGTTCTACT (SEQ ID NO: 61) |
| HPV 18 NOT aptamer | TGACATGGACCCTGCAGTGCCAATGTACAGTATTG (SEQ ID NO: 128) |
| HPV 18 target | AGTAGAACGCGATGGTACAGGCACTGCAGGGTCCATGTCA (SEQ ID NO: 62) |

Logic gate components (relative ratios)

AND Gate

| HPV 16 Aptamer | HPV 16 Inverter | HPV 18 Aptamer | HPV 18 Inverter | Taq Polymerase |
|---|---|---|---|---|
| 1 | 1 | 1 | 1 | 1 |

OR Gate

| HPV 16 Aptamer | HPV 16 Inverter | HPV 18 Aptamer | HPV 18 Inverter | Taq Polymerase |
|---|---|---|---|---|
| 1 | 1 | 1 | 1 | 2 |

HPV 16 NOT Gate

| HPV 16 NOT Apater | | | | Taq Polymerase |
|---|---|---|---|---|
| 1 | | | | 1 |

HPV 18 NOT Gate

| | | HPV 18 NOT Aptamer | | Taq Polymerase |
|---|---|---|---|---|
| | | 1 | | 2 |

NAND Gate

| HPV 16 NOT Aptamer | | HPV 18 NOT Aptamer | | Taq Polymerase |
|---|---|---|---|---|
| 1 | | 1 | | 2 |

TABLE 5-continued

Nanostructures for enVision logic gates.

NOR Gate

| HPV 16 NOT Aptamer | HPV 18 NOT Aptamer | Taq Polymerase |
|---|---|---|
| 1 | 1 | 1 |

Figure 4:
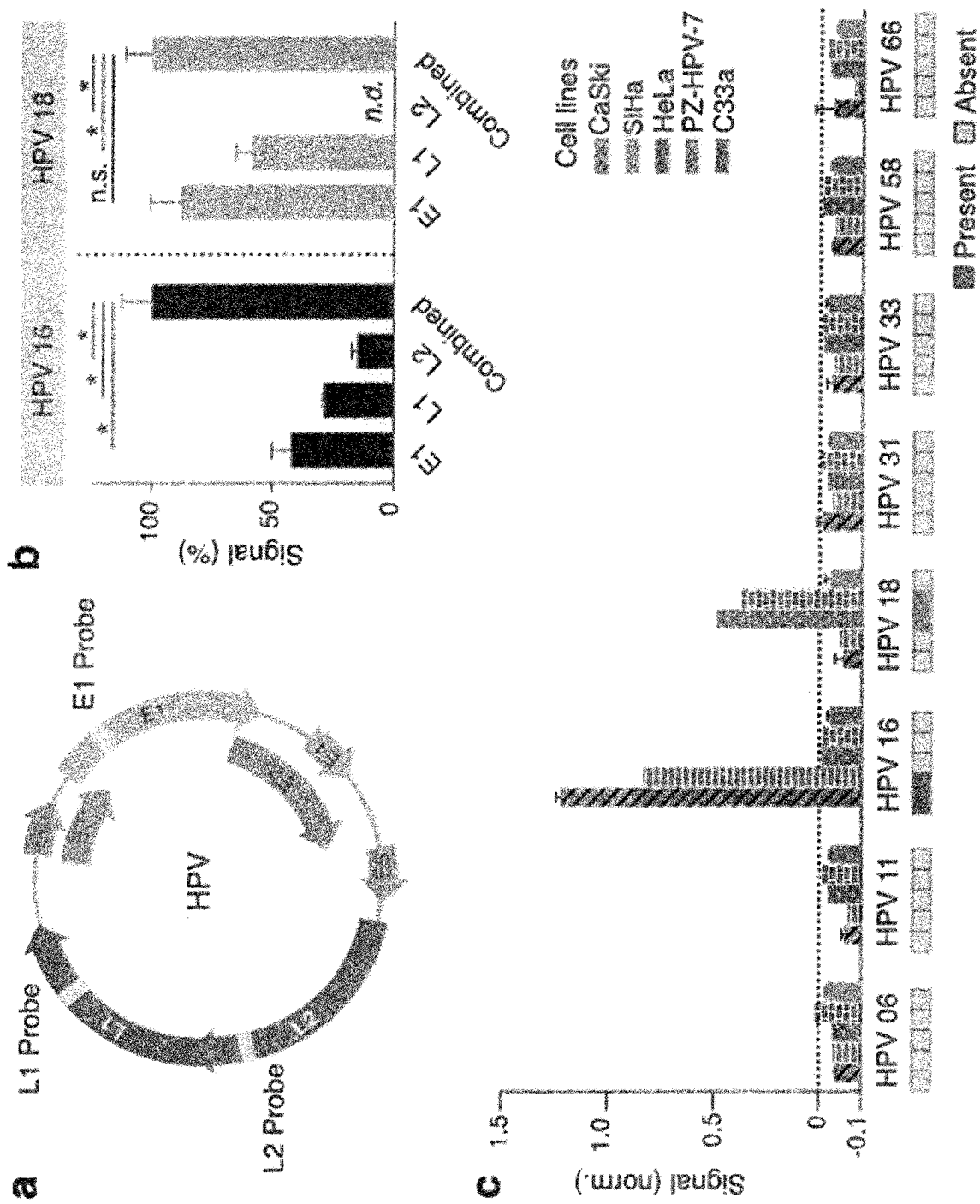
FIG. 4 shows multiplexed enVision for multi-loci coverage. (a) New probe loci in HPV genome map. The HPV genome is made up of seven early expressed (E) genes and two capsid protein (L) genes. New nanostructure recognition probes were designed for each HPV subtype to identify the E1, L1 and L2 loci, respectively. (b) Multiplexed enVision assays for high-coverage, multi-loci detection. Genomic DNA obtained from CaSki cells (left, HPV 16-positive) and HeLa cells (right, HPV 18-positive) were incubated directly with individual recognition probes (E1, L1 and L2, respectively) or a pool of three probes (combined) to determine the cellular HPV infection status. The combined probes showed significantly higher signals as compared to any of the individualized assays (*$P<0.0005$, n.s. not significant, Student's t test; n.d. not detected). All signals were normalized as a percentage to their respective combined signals. (c) HPV subtyping in cell lines. Genomic DNA from cell lines were profiled directly using the multiplexed enVision assays for different HPV subtypes. The measurements correlated well with the known HPV infections of the cell lines, as reported by previous literatures (dark grey: present, light grey: absent). All measurements were performed in triplicate, and the data are displayed as mean±s.d.
Figure 17:
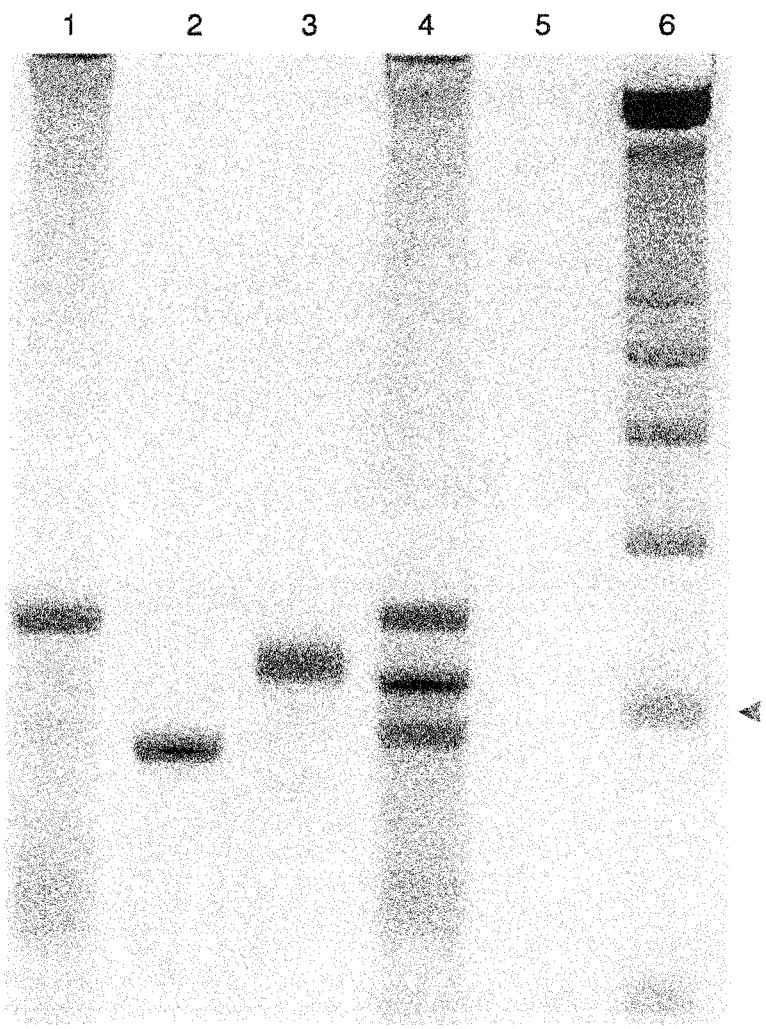
FIG. 17 shows multiplexed amplification of genomic DNA. Full gel electropherogram of amplification products from CaSki genomic DNA. Genomic DNA was amplified in the presence of different HPV 16 locus primers: (1) E1, (2) L1, (3) L2, (4) combined primers of E1, L1 and L2, as well as (5) no primers. Lane 7 was loaded with 15 bp DNA ladder. Arrow indicates the position of the 50 bp band.
Figure 18:
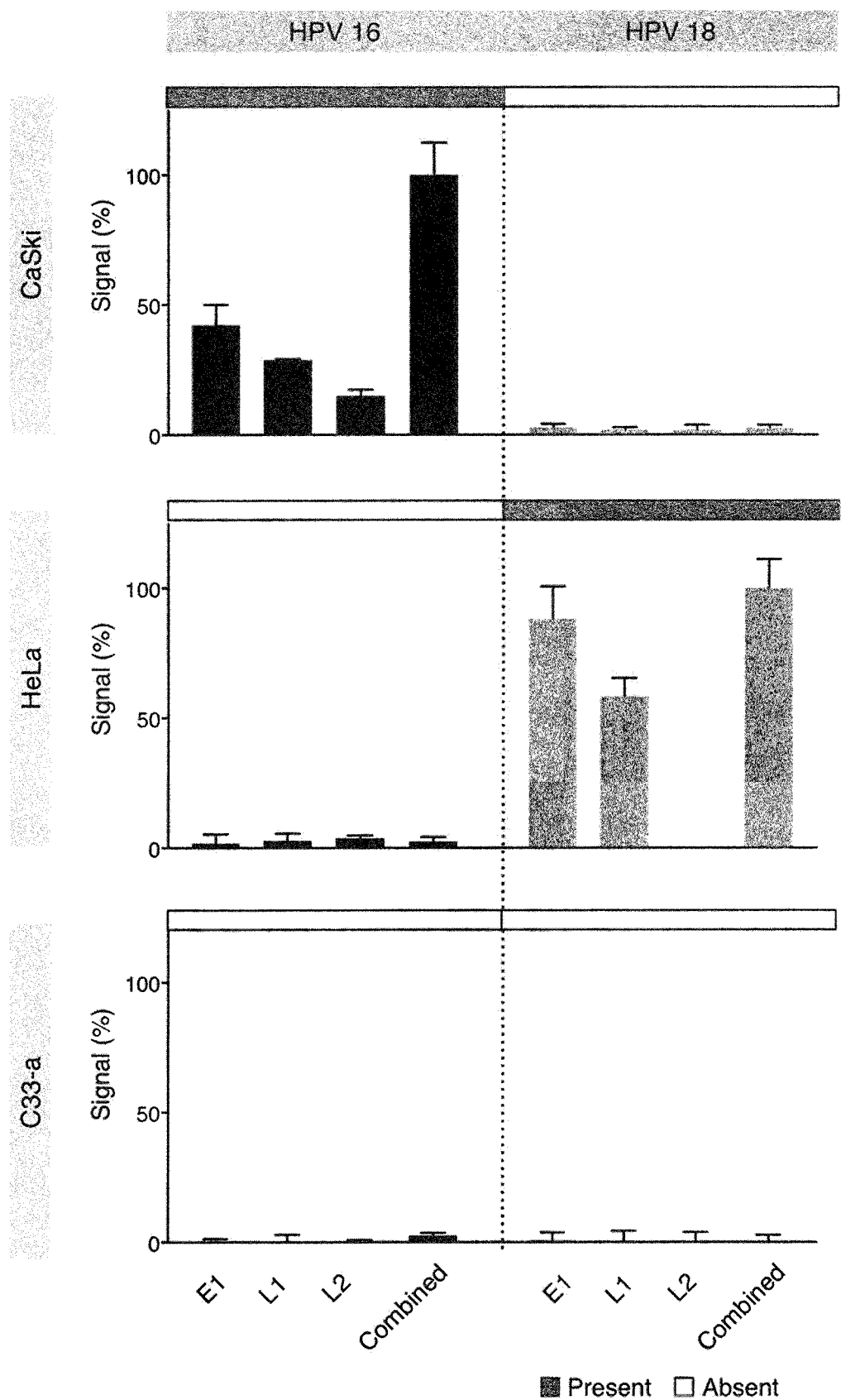
FIG. 18 shows multiplexed enVision detection of genomic DNA. Equal amounts of cellular genomic DNA (top: CaSki, middle: HeLa, bottom: C33-a) were incubated directly with specific recognition nanostructures against different HPV subtypes (left: HPV 16, right: HPV 18). Samples were treated with individual recognition nanostructures (i.e., E1, L1 and L2) or a pool of three structures simultaneously (combined). All signals were normalized as a percentage of the maximal signal observed for each HPV subtype. The multiplexed measurements correlated well with the known HPV infections of the cell lines, as reported by previous literatures (horizontal grey bar: present, horizontal white bar: absent). Note that the single locus measurement could miss positive infection (e.g., HeLa, HPV 18 locus L2). All measurements were performed in triplicate, and the data are displayed as mean±s.d.

To enhance detection coverage, for each HPV subtype (e.g., HPV 16 and HPV 18), we mixed its three types of locus-specific nanostructures (i.e., E1, L1 and L2 loci) to create the OR logic gate configuration in a single reaction. We tested this high-coverage, multi-loci HPV detection directly with genomic DNA of cervical cancer cell lines, which were independently validated with PCR analysis (FIG. 17). Our data showed that the multiplexed enVision assay could further enhance the detection signal, as compared to individualized detection with the E1, L1 and L2 recognition probes, respectively (FIG. 4b). Importantly, while true-positives showed significant signal enhancement, negative samples demonstrated minimal background signal change with this multiplexed approach (FIG. 18).

Using the multiplexed enVision assays, we next performed HPV profiling in human cervical cancer cell lines (FIG. 4c). All experiments were performed at room temperature, directly from cellular genomic DNA, without any pre-amplification. The multiplexed enVision analysis not only improved the signal enhancement, but also expanded the detection coverage to accurately identify the cells' infection status and subtypes, as compared to any single locus detection (FIG. 18). Our resultant measurements correlated well with published literature studies [Adey, A. et al. Nature 500: 207-211 (2013); Meissner, J. D. J Gen Virol 80: 1725-1733 (1999); Yee, C., et al., Am J Pathol 119: 361-366 (1985)]: CaSki and SiHa cells showed significant signals for HPV 16 only, while HeLa and PZ-HPV-7 showed positive signals for HPV 18 only.

We further benchmarked the enVision performance against another isothermal detection technique, namely LAMP, for HPV profiling of human cancer cell lines. On the same divergent regions of the HPV genome (FIG. 4a), we applied published criteria [Tomita, N., et al., Nat Protoc 3: 877-882 (2008); Song, J. et al. Anal Chem 88: 7289-7294 (2016)] to design LAMP primer sets against E1, L1 and L2 loci, respectively, for each HPV subtype (see Methods for details). All LAMP sequence information can be found in Table 6.

TABLE 6

Top-ranked LAMP primers for different HPV loci.

HPV 16 E1 LAMP primer set ΔG: -2.32 kcal/mol

| HPV 16 E1 LAMP Forward Internal Primer | TGGCGCCCTTCTACCTGTGAAACAG CGGGTATGGCAATA (SEQ ID NO: 129) | HPV 16 E1 LAMP Back Internal Primer | CACCATGTAGTCAGTATAGTGGTG TTTCACTAACACCCTCTCC (SEQ ID NO: 130) |
|---|---|---|---|
| HPV 16 E1 LAMP Forward Primer 3 | AGAGCTGCAAAAAGGAGA (SEQ ID NO: 131) | HPV 16 E1 LAMP Back Primer 3 | GTGTTTGGCATATAGTGTGTC (SEQ ID NO: 132) |

HPV 16 L1 LAMP primer set ΔG: -2.33 kcal/mol

| HPV 16 L1 LAMP Forward Internal Primer | TGGCAGCACATAATGACATATTTGT GGTAACCAACTATTTGTTACTGT (SEQ ID NO: 133) | HPV 16 L1 LAMP Back Internal Primer | AACTTTAAGGAGTACCTACGACAT GAGTTAAGGTTATTTTGCACAGT (SEQ ID NO: 134) |
|---|---|---|---|
| HPV 16 L1 LAMP Forward Primer 3 | CCACAATAATGGCATTTGTTG (SEQ ID NO: 135) | HPV 16 L1 LAMP Back Primer 3 | ATGTATGTATGTCATAACGTCTG (SEQ ID NO: 136) |

HPV 16 L2 LAMP primer set ΔG: -2.27 kcal/mol

| HPV 16 L2 LAMP Forward Internal Primer | CCGGGGTTGTAGAAGTATCTGTAAT CTCACCTACTTCTATTAATAATGGA (SEQ ID NO: 137) | HPV 16 L2 LAMP Back Internal Primer | TACCATCTGTACCCTCTACATCTT TGGAATATTGTATGCACCACCA (SEQ ID NO: 138) |
|---|---|---|---|
| HPV 16 L2 LAMP Forward Primer 3 | CATATACTACCACTTCACATGC (SEQ ID NO: 139) | HPV 16 L2 LAMP Back Primer 3 | AATGGGTATATCAGGACCTG (SEQ ID NO: 140) |

HPV 18 E1 LAMP primer set ΔG: -2.03 kcal/mol

| HPV 18 E1 LAMP Forward Internal Primer | TGAATCTGTGTTGCTTCCACTTCGC GGCTGTTTACAATATCAGA (SEQ ID NO: 141) | HPV 18 E1 LAMP Back Internal Primer | AACATGGCGGCAATGTATGTAGTG TCTACACTGCTGTTGTTG (SEQ ID NO: 142) |
|---|---|---|---|
| HPV 18 E1 LAMP Forward Primer 3 | TAGTGGGCAGAAAAAGGC (SEQ ID NO: 143) | HPV 18 E1 LAMP Back Primer 3 | ATTGCTATTGTCACTTGTACC (SEQ ID NO: 144) |

HPV 18 L1 LAMP primer set ΔG: -2.33 kcal/mol

| HPV 18 L1 LAMP Forward Internal Primer | AATCATATTCCTCAACATGTCTGCT CTCCTGTACCTGGGCAAT (SEQ ID NO: 145) | HPV 18 L1 LAMP Back Internal Primer | ACTTTAACTGCAGATGTTATGTCC TACCAAAGTTCCAATCCTCTA (SEQ ID NO: 146) |
|---|---|---|---|

TABLE 6-continued

Top-ranked LAMP primers for different HPV loci.

| HPV 18 L1 LAMP Forward Primer 3 | CAATATGTGCTTCTACACAGT (SEQ ID NO: 147) | HPV 18 L1 LAMP Back Primer 3 | |
|---|---|---|---|
| HPV 18 L2 LAMP primer set ΔG: -2.11 kcal/mol | | | |
| HPV 18 L2 LAMP Forward Internal Primer | AAGGAGGTAGTAGAACGCGATGCTT GTTTGATATATATGCAGATGAC (SEQ ID NO: 149) | HPV 18 L2 LAMP Back Internal Primer | TGCATTTTTTAAATATTCGCCCAC TGGAGGTTAAAGGGACCGT (SEQ ID NO: 150) |
| HPV 18 L2 LAMP Forward Primer 3 | CTTTAGTATCTGCCACGGA (SEQ ID NO: 151) | HPV 18 L2 LAMP Back Primer 3 | TACAGGCACATCCCAAGA (SEQ ID NO: 152) |

Top-Ranked LAMP Primers were Determined from their AG, the Change in Free Energy During Lamp Reaction.

Figure 19:
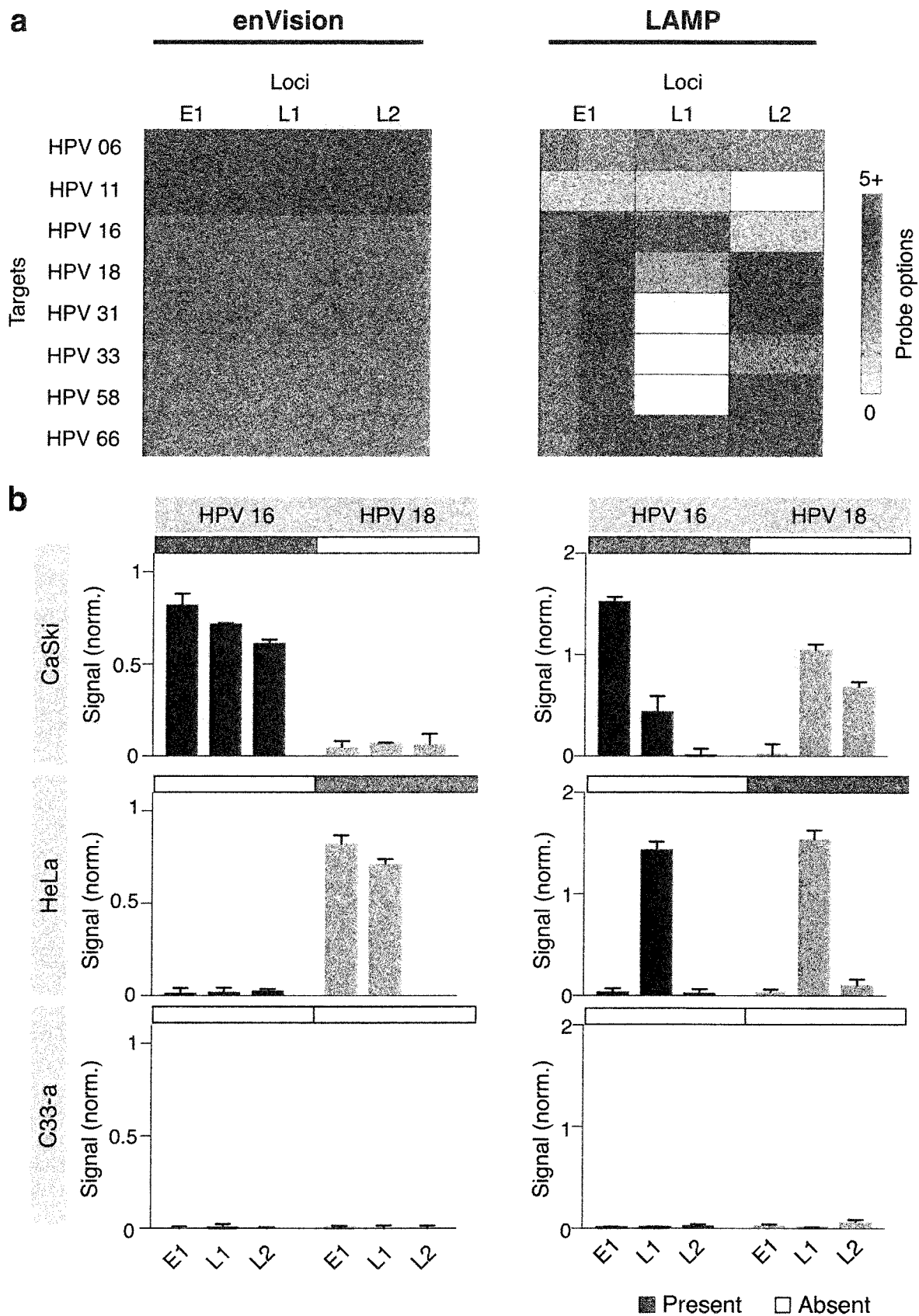
FIG. 19 shows comparison of enVision and LAMP design and performance. (a) Comparison of probe options found in the highly variable regions of the E1, L1 and L2 loci in different HPV subtypes. Probe options were identified for the enVision system (left) as well as LAMP (right). The enVision platform not only generated more probe choices but also provided comprehensive coverage for all regions tested. (b) Comparison of enVision performance (left) with that of top-ranked LAMP primer sets (right) for HPV subtyping in cellular genomic DNA. EnVision had 83.3% sensitivity (5/6) and 100% specificity (12/12) while LAMP had 50.0% sensitivity (3/6) and 75.0% specificity (9/12). Multi-loci measurements were made across different cell lines of known infections. All signals were normalized to appropriate controls (no-target controls) as previously described. Note that only the enVision technology showed accurate HPV subtyping, as compared to known cellular infection status (horizontal grey bar: present, horizontal white bar: absent). LAMP demonstrated significant false positives (e.g., CaSki cells, HPV 18; HeLa cells, HPV 16). All measurements were performed in triplicate, and the data are displayed as mean±s.d.

In comparison to LAMP's limited primer options, the enVision technology not only generated significantly more probe choices but also provided comprehensive coverage across all subtypes and loci tested (FIG. 19a). We further compared the performance of the enVision technology against top-ranked LAMP primer sets, using genomic DNA isolated from cell lines of known infections (FIG. 19b). Only the enVision technology showed accurate HPV subtyping while LAMP demonstrated significant false positives (e.g., CaSki cells, HPV 18; HeLa cells, HPV 16).

Example 6

HPV Profiling of Clinical Samples

To test the clinical utility of the enVision platform in detecting and subtyping HPV infections, we conducted a feasibility study aimed at addressing two questions: (1) how accurate is the enVision platform in detecting HPV infections, and (2) can improved assay coverage identify previously undetectable infections.

Figure 5:
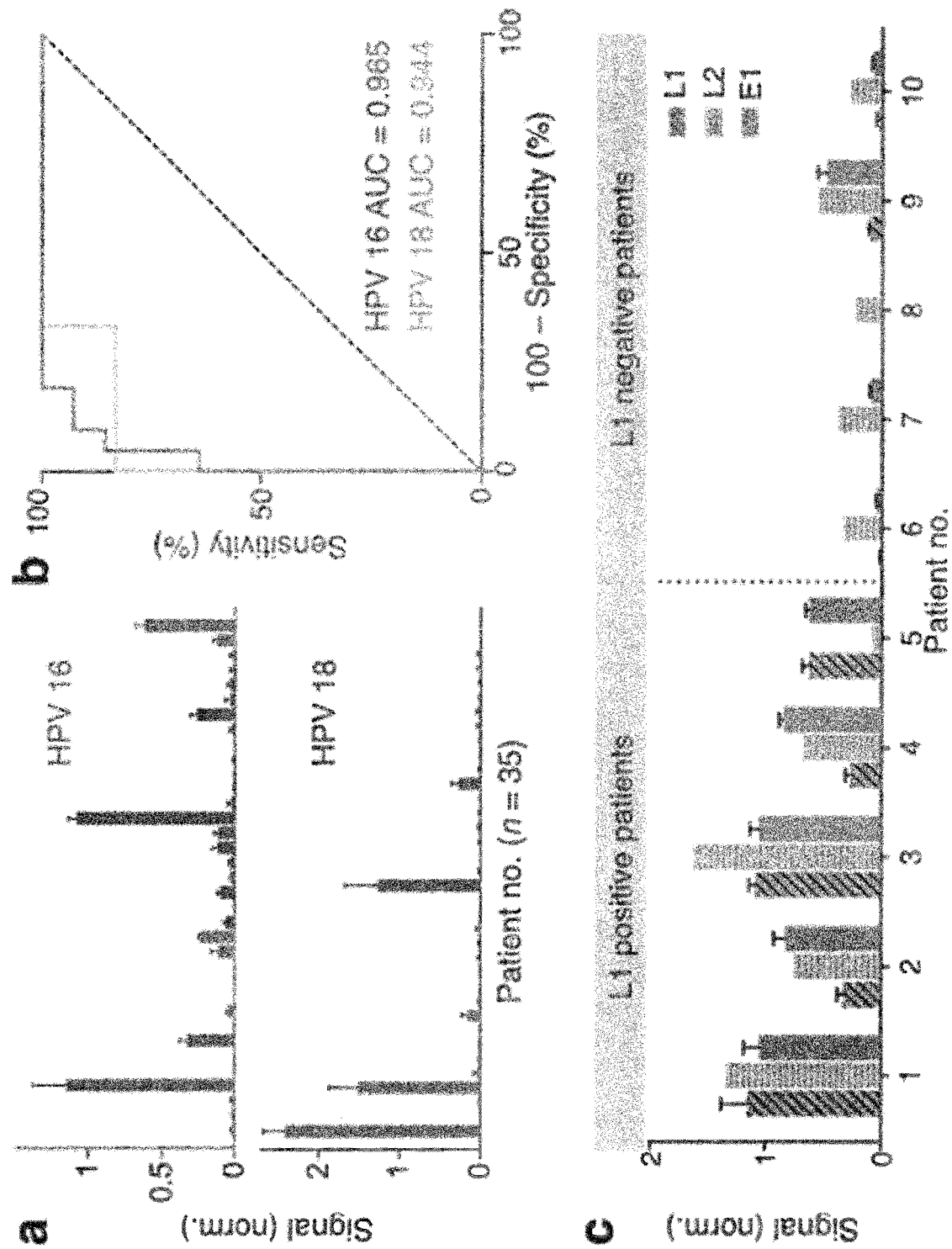
FIG. 5 shows molecular profiling of patient samples. (a) HPV 16 and HPV 18 signals were measured from clinical endocervical brush samples (n=35). The L1-specific signals are shown for comparison with the clinical gold standard. See FIG. 19 for multi-loci measurements on all clinical specimens. (b) Receiver operator characteristic (ROC) curves of the HPV 16 and HPV 18 L1 locus assays were used to determine the detection accuracies. HPV 16 assay showed 92.9% sensitivity (13/14) and 90.5% specificity (19/21) and HPV 18 assay showed 83.3% sensitivity (5/6) and 100% specificity (29/29) at the Youden's index cutoff. (c) Locus-specific HPV 16 enVision assays (L1, L2 and E1 locus assays) were performed in all patients. Representative examples from L1-positive (left) and L1-negative (right) patients are shown. Note that in the subset of L1-negative patients, the inclusion of L2 and E1 locus assays could improve the detection coverage to identify previously undetectable infections. This was further validated through independent Taqman® fluorescence analysis, which showed a high concordance with the enVision results in all tested clinical specimens (see FIG. 20). All measurements were performed in triplicate, and the data are displayed as mean±s.d. AUC, area under the curve.

Using clinical endocervical brush samples, we performed the enVision assays to determine the HPV infection status. We acquired patient samples (n=35) and used the enVision platform to measure HPV 16 and HPV 18 L1 loci in patient genome (FIG. 5a), so as to compare directly against conventional gold standard (i.e., Cobas HPV which tests only for the L1 locus through qPCR analysis [Gardner, S. N., et al., *J Clin Microbiol* 41: 2417-2427 (2003)]). The enVision platform achieved a high detection accuracy with the clinical reports (HPV 16, AUC=0.965; HPV 18, AUC=0.944) (FIG. 5b).

Figure 20:
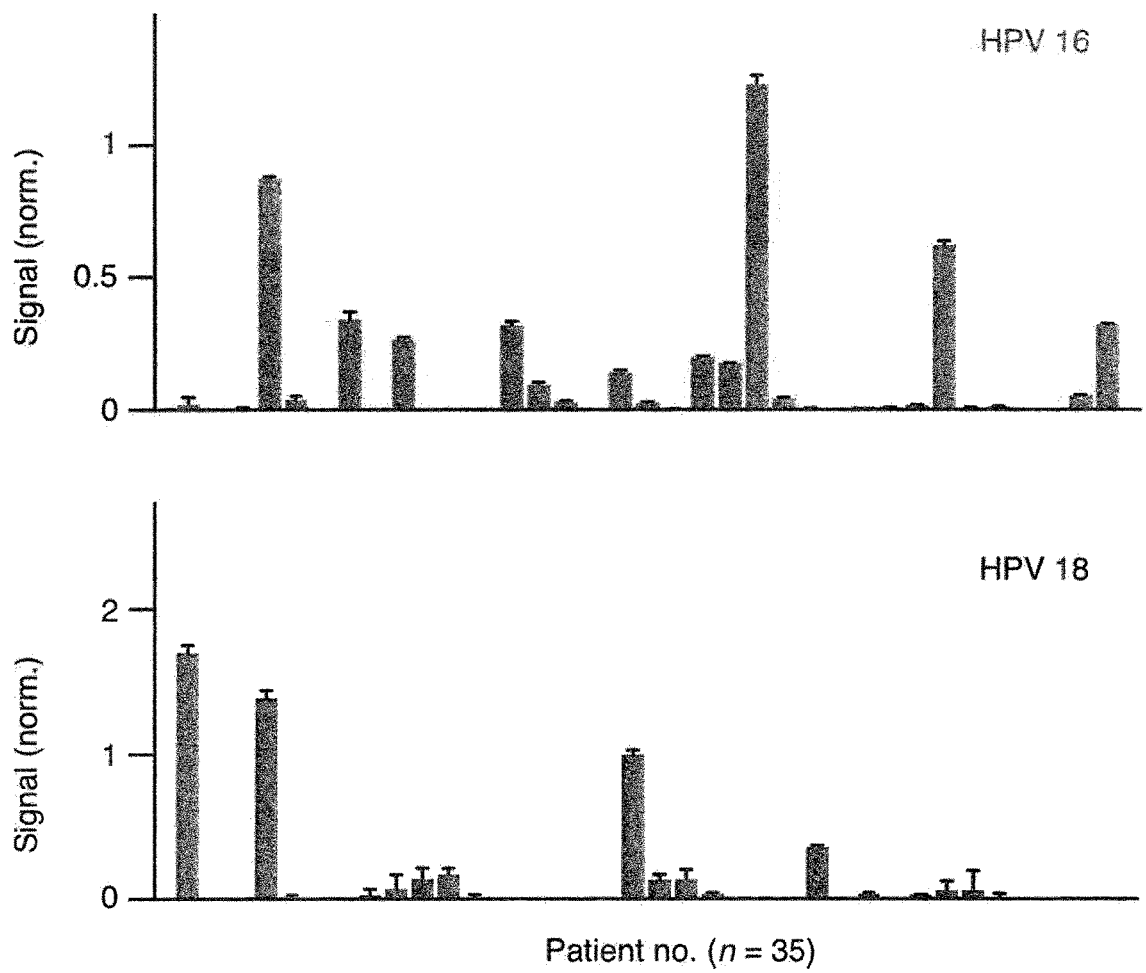
FIG. 20 shows multiplexed enVision detection in clinical samples. High-coverage multi-loci enVision assays (simultaneous detection of E1, L1 and L2) were performed in clinical endocervical brush samples (n=35 patients) for molecular subtyping of HPV 16 (top panel) and HPV 18 (bottom panel). All measurements were performed in triplicate, and the data are displayed as mean±s.d.
Figure 21:
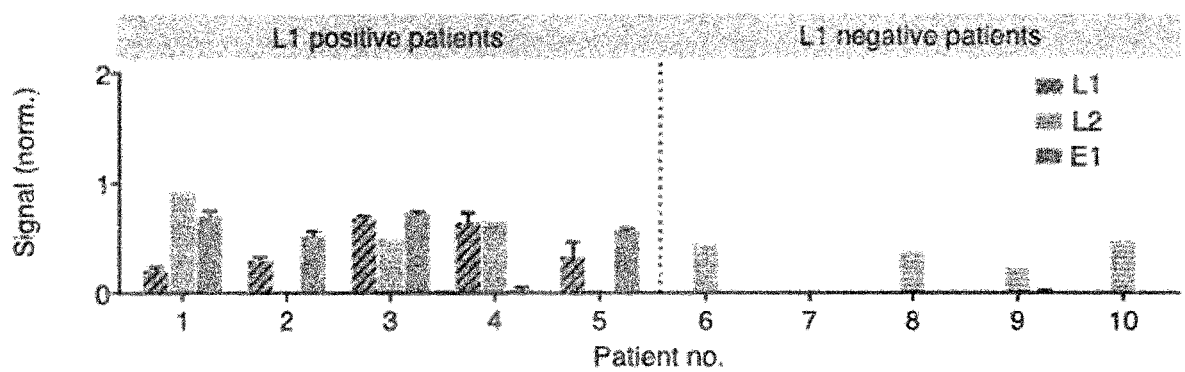
FIG. 21 shows clinical validation with Taqman® fluorescence assays. Taqman® assays were designed to detect the HPV 16 E1, L1 and L2 loci, respectively. All clinical validation assays were performed with qPCR analysis. Relative quantitation was performed for each sample by normalizing with respective GAPDH expression. Note that the data correlated well to the signals detected with the enVision platform to identify previously undetectable infections (see FIG. 5c). All measurements were performed in triplicate, and the data are displayed as mean±s.d.
Figure 22:
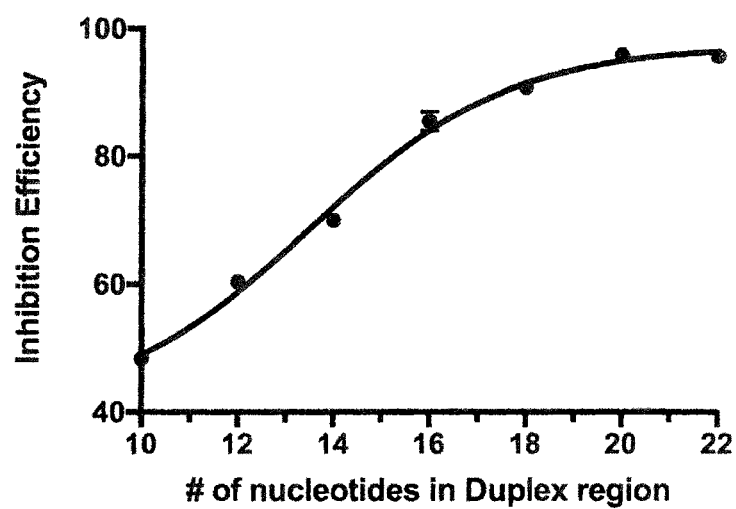
FIG. 22 shows the efficiency of DNA polymerase inhibition by the aptamer with varying numbers of nucleotides in the duplex segment. The efficiency begins to plateau at about 20 nucleotides in the duplex segment. All measurements were performed in triplicate, and the data are displayed as mean±s.d.

We also used the high-coverage multi-loci enVision assays to measure, in addition to the L1 locus, L2 and E1 locus integrations in these clinical samples (FIG. 20). In the HPV 16 L1-positive clinical samples, we continued to observe enhanced visual signals for the other detection loci. Interestingly, in a subset of the L1-negative samples, the high-coverage enVision system detected specific L2 and/or E1 locus integrations (FIG. 5c). We further validated this finding by designing an independent Taqman® fluorescence analysis (Table 4), which showed high concordance with the enVision results in all tested clinical specimens (FIG. 21). Results indicate that the multiplexed enVision platform could improve the detection coverage to identify previously undetectable infections.

Any listing or discussion of an apparently prior-published document in this specification should not necessarily be taken as an acknowledgement that such document is part of the state of the art or is common general knowledge.

Discussion

By integrating a series of enzyme-assisted DNA nanostructures, the enVision platform enables sensitive and versatile detection of diverse pathogen nucleic acids by the naked eye. In comparison to nucleic acid amplification techniques, enVision detects via direct target hybridization and independent visual signal enhancement. The technology is thus well-suited for clinical applications: (1) the cascading signal enhancement produces a rapid and sensitive color readout for the naked eye upon target hybridization (without needing for target amplification). The entire assay can thus be performed at room temperature and readily quantified with smartphones; (2) the DNA nanostructures effectively decouple recognition and signaling functionalities to enable highly programmable detection and logic computation; and (3) the microfluidic integration complements the assay modularity and speeds up the reactions. In comparison to clinical gold standard and other isothermal detection technologies, the enVision platform not only demonstrated superior sensitivity and specificity, but also afforded versatile capabilities (e.g., direct RNA detection, logic computation and assay modularity) with minimal equipment requirement (Table 7).

TABLE 7

Comparison of detection technologies.

| | enVision | PCR (SYBR ®, Taqman ®, e.g., Cobas HPV) | Isothermal amplification (LAMP) | Hybridization |
|---|---|---|---|---|
| Detection limit | High femtomole (without target preamplification), attomole (with target preamplification) | High attomole[a] | High Attomole[b] | Low Nanomole[c] |

TABLE 7-continued

Comparison of detection technologies.

|  | enVision | PCR (SYBR ®, Taqman ®, e.g., Cobas HPV) | Isothermal amplification (LAMP) | Hybridization |
|---|---|---|---|---|
| Sensitivity (95% CI) | High 94.7%-100% | Moderate to high 63.1%-100% | Low 43.5%-76.9% | High 85.2%-98.1%[d] |
| Specificity (95% CI) | High 93.6%-100% | Moderate to high 83.0%-98.1% | Moderate 52.3%-93.5% | Moderate to high 89.9%-91.4%[d] |
| Target options | DNA and RNA | DNA | DNA | DNA and RNA |
| Sequence design stringency | Low single 20-40 base sequence | Moderate pair of 18-25 base sequences | High sets of four or six 25-35 base sequences | Low single 20-40 base sequence |
| Versatility | High | Moderate | Low | Moderate |
| Robustness | High | Moderate to high | Low | Moderate |
| Time taken | as little as 30 min | ~2 h | ~1 h | >2 h, multiple washes |
| Temperature requirement | Isothermal | Thermal cycling | Isothermal | Isothermal |
| Equipment requirement | Minimal (smartphone) | High (thermocycler and fluorometer) | Moderate (fluorometer) | Moderate (fluorometer or colorimeter) |
| Ease of use | Minimal training | Trained personnel | Trained personnel | Trained personnel |
| Cost/reaction | <$1 | $1-3 | <$1 | $1-2 |

CI, confidence interval.
[a]Rao, A. et al. *J Clin Microbiol* 51: 1478-1484 (2013);
[b]Lucchi, N. W. et al. *Sci Rep* 6: 36808 (2016);
[c]Lee, J. S., et al., *Biomed Res Int* 2013, 8 (2013);
[d]Kang, L. N. et al. *J Clin Microbiol* 52: 1954-1961 (2014).

The scientific and clinical applications of the developed technology are potentially broad. The recognition nanostructure can be easily adapted, at a very low cost, to detect different target sequences with similar efficiencies (i.e., only a single probe sequence composed of regular nucleotides needs to be adapted, instead of requiring for new sets of conventional primers or dedicated chemically-modified reporters). The signaling nanostructure is universal and can be used for all target sequences. Such modularity not only eases new assay development, but also enables programmable configuration to perform molecular computations. We thus anticipate that the technology will be particularly useful for investigating rapid viral mutations that escape immune detection (i.e., RNA viruses)[Schotte, L. et al., *Antimicrob Agents Chemother* 59: 4695-4706 (2015)] as well as multiple virus-host genome integrations [Cheung, J. L., et al., *J Infect Dis* 194: 1706-1712 (2006)]. Clinically, the enVision technology's visual detection and low equipment requirement make the technology well-suited for point-of-care detection workflow in community clinics and resource-limited settings.

We further anticipate that several technical modifications could be made to enhance the current technology. First, the present fluidics (i.e., four assay cassettes) could be readily revised to accommodate more and smaller chambers. As the current nucleic acid processing is performed off-chip, additional sample preparation modules could also be integrated to enable nucleic acid extraction and treatment, thereby enhancing the platform's clinical utility [Adey, A. et al. *Nature* 500: 207-211 (2013)]. Such a new design would enable practical, array-type visual detection of multiple pathogen nucleic acids. Second, in this current detection platform, smartphones were used and a corrected lighting system to image and analyze the visual readouts. Since smartphones are becoming ubiquitous and possess more analytical capabilities [Laksanasopin, T. et al. *Sci Transl Med* 7: 273re1 (2015); Nemiroski, A. et al. *Proc Natl Acad Sci USA* 111: 11984-11989 (2014); Paterson, A. S. et al. *Lab Chip* 17: 1051-1059 (2017)], we foresee that further image correction and analysis algorithms could be implemented directly in smartphones to automatically correct for lighting differences and quantify color intensities for real-world applications.

REFERENCES

1. Adey, A. et al. The haplotype-resolved genome and epigenome of the aneuploid HeLa cancer cell line. *Nature* 500, 207-211 (2013).
2. Bodily, J. & Laimins, L. A. Persistence of human papillomavirus infection: keys to malignant progression. *Trends Microbiol* 19, 33-39 (2011).
3. Bouvard, V. et al. A review of human carcinogens—Part B: biological agents. *Lancet Oncol* 10, 321-322 (2009).
4. Cheung, J. L., Lo, K. W., Cheung, T. H., Tang, J. W. & Chan, P. K. Viral load, E2 gene disruption status, and lineage of human papillomavirus type 16 infection in cervical neoplasia. *J Infect Dis* 194, 1706-1712 (2006).
5. Crosbie, E. J., Einstein, M. H., Franceschi, S. & Kitchener, H. C. Human papillomavirus and cervical cancer. *Lancet* 382, 889-899 (2013).
6. Cui, M. et al. Clinical performance of Roche Cobas 4800 HPV Test. *J Clin Microbiol* 52, 2210-2211 (2014).
7. Dang, C. & Jayasena, S. D. Oligonucleotide inhibitors of Taq DNA polymerase facilitate detection of low copy number targets by PCR. *J Mol Biol* 264, 268-278 (1996).
8. Gardner, S. N., Kuczmarski, T. A., Vitalis, E. A. & Slezak, T. R. Limitations of TaqMan PCR for detecting divergent viral pathogens illustrated by hepatitis A, B, C, and E viruses and human immunodeficiency virus. *J Clin Microbiol* 41, 2417-2427 (2003).

9. Juskowiak, B. Nucleic acid-based fluorescent probes and their analytical potential. *Anal Bioanal Chem* 399, 3157-3176 (2011).
10. Kang, L. N. et al. Optimal positive cutoff points for care HPV testing of clinician- and self-collected specimens in primary cervical cancer screening: an analysis from rural China. *J Clin Microbiol* 52, 1954-1961 (2014).
11. Laksanasopin, T. et al. A smartphone dongle for diagnosis of infectious diseases at the point of care. *Sci Transl Med* 7, 273re1 (2015).
12. Lee, H. et al. Molecularly self-assembled nucleic acid nanoparticles for targeted in vivo siRNA delivery. *Nat Nanotechnol* 7, 389-393 (2012).
13. Lee, J. S., Song, J. J., Deaton, R. & Kim, J.-W. Assessing the Detection Capacity of Microarrays as Bio/Nanosensing Platforms. *Biomed Res Int* 2013, 8 (2013).
14. Li, J., Green, A. A., Yan, H. & Fan, C. Engineering nucleic acid structures for programmable molecular circuitry and intracellular biocomputation. *Nat Chem* 9, 1056-1067 (2017).
15. Lucchi, N. W. et al. Evaluation of the Illumigene Malaria LAMP: A Robust Molecular Diagnostic Tool for Malaria Parasites. *Sci Rep* 6, 36808 (2016).
16. McBride, A. A. & Warburton, A. The role of integration in oncogenic progression of HPV-associated cancers. *PLoS Pathog* 13, e1006211 (2017).
17. Meissner, J. D. Nucleotide sequences and further characterization of human papillomavirus DNA present in the CaSki, SiHa and HeLa cervical carcinoma cell lines. *J Gen Virol* 80, 1725-1733 (1999).
18. Nemiroski, A. et al. Universal mobile electrochemical detector designed for use in resource-limited applications. *Proc Natl Acad Sci USA* 111, 11984-11989 (2014).
19. Niemz, A., Ferguson, T. M. & Boyle, D. S. Point-of-care nucleic acid testing for infectious diseases. *Trends Biotechnol* 29, 240-250 (2011).
20. Nong, R. Y., Gu, J., Darmanis, S., Kamali-Moghaddam, M. & Landegren, U. DNA-assisted protein detection technologies. *Expert Rev Proteomics* 9, 21-32 (2012).
21. Pardee, K. et al. Rapid, Low-Cost Detection of Zika Virus Using Programmable Biomolecular Components. *Cell* 165, 1255-1266 (2016).
22. Park, K. S. et al. Rapid identification of health care-associated infections with an integrated fluorescence anisotropy system. *Sci Adv* 2, e1600300 (2016).
23. Paterson, A. S. et al. A low-cost smartphone-based platform for highly sensitive point-of-care testing with persistent luminescent phosphors. *Lab Chip* 17, 1051-1059 (2017).
24. Rao, A. et al. Development and Characterization of the cobas Human Papillomavirus Test. *J Clin Microbiol* 51, 1478-1484 (2013).
25. Schiffman, M. et al. Carcinogenic human papillomavirus infection. *Nat Rev Dis Primers* 2, 16086 (2016).
26. Schotte, L. et al. Characterization of Poliovirus Neutralization Escape Mutants of Single-Domain Antibody Fragments (VHHs). *Antimicrob Agents Chemother* 59, 4695-4706 (2015).
27. Shao, H. et al. Chip-based analysis of exosomal mRNA mediating drug resistance in glioblastoma. *Nat Commun* 6, 6999 (2015).
28. Sievers, F. et al. Fast, scalable generation of high-quality protein multiple sequence alignments using Clustal Omega. *Mol Syst Biol* 7, 539 (2011).
29. Song, J. et al. Instrument-Free Point-of-Care Molecular Detection of Zika Virus. *Anal Chem* 88, 7289-7294 (2016).
30. Tomita, N., Mori, Y., Kanda, H. & Notomi, T. Loop-mediated isothermal amplification (LAMP) of gene sequences and simple visual detection of products. *Nat Protoc* 3, 877-882 (2008).
31. Wang, L., Meng, Z., Martina, F., Shao, H. & Shao, F. Fabrication of circular assemblies with DNA tetrahedrons: from static structures to a dynamic rotary motor. *Nucleic Acids Res* 45, 12090-12099 (2017).
32. Williams, V. M., Filippova, M., Soto, U. & Duerksen-Hughes, P. J. HPV-DNA integration and carcinogenesis: putative roles for inflammation and oxidative stress. *Future Virol* 6, 45-57 (2011).
33. Yee, C., Krishnan-Hewlett, I., Baker, C. C., Schlegel, R. & Howley, P. M. Presence and expression of human papillomavirus sequences in human cervical carcinoma cell lines. *Am J Pathol* 119, 361-366 (1985).
34. Zhao, Y., Chen, F., Li, Q., Wang, L. & Fan, C. Isothermal Amplification of Nucleic Acids. *Chem Rev* 115, 12491-12545 (2015).
35. Zumla, A. et al. Rapid point of care diagnostic tests for viral and bacterial respiratory tract infections—needs, advances, and future prospects. *Lancet Infect Dis* 14, 1123-1135 (2014).

The invention claimed is:

1. A method of detecting target nucleic acids in a sample, comprising the steps of:
   (a) providing a sample comprising nucleic acid;
   (b) providing a composition comprising at least one DNA polymerase enzyme and at least one recognition nanostructure, wherein the recognition nanostructure comprises a DNA polymerase enzyme-specific DNA aptamer having a conserved sequence region and a variable sequence region, wherein the variable sequence region comprises an overhang segment which is at least 10 nucleotides complementary to a target nucleic acid in the sample; or
   (c) providing a composition comprising at least one DNA polymerase enzyme and at least one recognition nanostructure, wherein the recognition nanostructure comprises a DNA polymerase enzyme-specific DNA aptamer and an inverter oligonucleotide, wherein the aptamer has a conserved sequence region and a variable sequence region, wherein the variable sequence region comprises an overhang segment which is at least 10 nucleotides complementary to, and forms a duplex with, a portion of the inverter oligonucleotide, wherein the inverter oligonucleotide is at least one nucleotide longer than the aptamer-inverter duplex and has more than 10 nucleotides complementary to a target nucleic acid in the sample;
   (d) contacting the sample comprising nucleic acid with the composition of (b) or (c), wherein target nucleic acid binding to:
      (i) the variable sequence region of the aptamer in (b) promotes the formation of a stable aptamer-DNA polymerase enzyme complex, thereby inhibiting DNA polymerase enzyme activity; or
      (ii) the inverter oligonucleotide in (c) destabilizes the recognition nanostructure, thereby releasing the DNA polymerase enzyme from inhibition by the DNA aptamer;
   (e) providing a signaling nanostructure that is reactive to active DNA polymerase enzyme from step (d), wherein the signaling nanostructure comprises a self-priming portion responsive to the DNA polymerase enzyme;
   (f) contacting the signaling nanostructure with active DNA polymerase enzyme from step (d) in the presence of labelled oligonucleotides (dNTPs) and signal development reagents, wherein the activated DNA polymerase enzyme adds labelled oligonucleotides to the signaling nanostructure and the signal development reagents bind to the labelled oligonucleotides incorporated into the self-primed portion;
   (g) detecting signal development, wherein the intensity of signal indicates;
      (i) absence of target nucleic acid in the sample when using composition (b); or
      (ii) the presence of target nucleic acid in the sample when using composition (c).

2. The method according to claim 1, wherein the DNA aptamer conserved sequence region comprises the nucleic acid sequence set forth in 5'-CAATGTACAGTATTG-3' (SEQ ID NO: 153).

3. The method according to claim 1, wherein the inverter oligonucleotide is at least one nucleotide longer than the aptamer duplex region.

4. The method according to claim 3, wherein the inverter oligonucleotide is about 35 to 45, preferably about 40, nucleotides in length.

5. The method according to claim 1, wherein about half of the length of the inverter oligonucleotide forms the aptamer-inverter duplex and about half forms an overhang segment.

6. The method according to claim 1, further comprising providing one or more additional recognition nanostructures complementary to one or more target nucleic acids different from the target nucleic acid of a first recognition nanostructure in the sample, for multiplex detection.

7. The method according to claim 6, wherein each of the recognition nanostructures comprises a combination of DNA aptamer:inverter oligonucleotide:DNA polymerase enzyme in a ratio to form a logic gate selected from a group comprising AND, OR, NOT, NAND and NOR.

8. The method according to claim 7, wherein the combination of DNA aptamer:inverter oligonucleotide:DNA polymerase enzyme ratio of each recognition nanostructure are selected from the group (i) to (v) comprising:
  (i) two nanostructures each having 1:1:0.5 DNA aptamer: inverter oligonucleotide:DNA polymerase enzyme ratio to form a AND logic gate;
  (ii) two nanostructures each having 1:1:1 DNA aptamer: inverter oligonucleotide:DNA polymerase enzyme ratio to form a OR logic gate;
  (iii) one nanostructure having 1:0:1 to form a NOT logic gate;
  (iv) two nanostructures each having 1:0:1 DNA aptamer: inverter oligonucleotide:DNA polymerase enzyme ratio to form a NAND gate; and
  v) two nanostructures each having 1:0:0.5 DNA aptamer: inverter oligonucleotide:DNA polymerase enzyme ratio to form a NOR gate.

9. The method according to claim 1, wherein the self-priming portion of the signaling nanostructure comprises the nucleic acid sequence set forth in SEQ ID NO: 5.

10. The method according to claim 1, wherein the dNTP label is biotin.

11. The method according to claim 1, wherein the signal development reagents comprise a fusion protein comprising avidin or a derivative thereof and an enzyme, selected from a group comprising but not limited to HRP, beta-lactamase, amylase, beta-galactosidase, and respective substrates selected from a group comprising but not limited to DAB, TMB, ABTS, nitrocefin, luminol, starch and iodine, wherein signals can be measured and quantified as but not limited to colour, fluorescence, luminescence or electrochemical changes.

12. The method according to claim 1, wherein the target is at least one nucleic acid associated with a non-human or human disease, genetic variants, forensic, strain identification, environmental and/or food contamination.

13. The method according to claim 1, wherein the target is at least one pathogen nucleic acid.

14. The method according to claim 1, wherein step (a) is preceded by amplification of the target nucleic acid in the sample.

15. The method according to claim 14, wherein the amplification of the target nucleic acid in the sample is by nested asymmetric PCR or isothermal amplification methods.

16. The method according to claim 1, wherein practice of the detection and signaling steps are spatially separated.

17. The method according to claim 1, wherein the detection and signaling nanostructures are attached to a substrate.

18. The method according to claim 17, wherein the signaling nanostructures are attached to beads.

19. The method according to claim 17 or 18, wherein the detection and signaling nanostructures are attached to a microfluidic device or lateral flow device.

20. The method according to claim 1, wherein the steps d) to g), preferably steps a) to g), are performed at a temperature in the range from 16° C. to 40° C., preferably at ambient temperature.

21. The method according to claim 1, wherein the target nucleic acid is a HPV nucleic acid.

22. The method according to claim 21, wherein the aptamer and inverter oligonucleotides are selected from those listed in Table 2, Table 4 or Table 5.

23. A device comprising:
  (i) the composition of (b) or (c) of claim 1 comprising at least one DNA polymerase enzyme and at least one recognition nanostructure at a $1^{st}$ location;
  (ii) signaling nanostructures comprising a self-priming portion responsive to active DNA polymerase enzyme attached at a $2^{nd}$ location; and
  (iii) an intermediate stage for mixing of said detection nanostructures with sample nucleic acid to release active enzyme to said $2^{nd}$ location.

24. The device of claim 23, selected from a group comprising a microfluidic device and a lateral flow device.

25. The device of claim 23, wherein the device is a microfluidic device comprising:
  (i) a common signaling cartridge configured to receive one or more assay cassettes, wherein the cartridge comprises a base with membranes embedded to immobilize signaling nanostructures, and a common outlet which makes fluid connection with said $2^{nd}$ location in each of the one or more assay cassettes;
  (ii) one or more assay cassettes each comprising, at a $1^{st}$ location, an inlet and at least one DNA polymerase enzyme and at least one recognition nanostructure; an intermediate stage microchannel in fluid connection between the $1^{st}$ and $2^{nd}$ locations, for mixing of said detection nanostructures with sample nucleic acid to release active enzyme to said $2^{nd}$ location;
  wherein, when the device is assembled and in use, there is fluidic flow from the sample inlet to the common outlet, actuated by a withdrawal septum.

26. A nucleic acid detection kit comprising;
  (a) a composition comprising at least one DNA polymerase enzyme and at least one recognition nanostructure, wherein the recognition nanostructure comprises a DNA polymerase enzyme-specific DNA aptamer having a conserved sequence region and a variable sequence region, wherein the variable sequence region comprises an overhang segment which is at least 10 nucleotides complementary to a target nucleic acid; and/or
  (b) a composition comprising at least one DNA polymerase enzyme and at least one recognition nanostructure, wherein the recognition nanostructure comprises a DNA polymerase enzyme-specific DNA aptamer and an inverter oligonucleotide, wherein the aptamer has a conserved sequence region and a variable sequence region, wherein the variable sequence region comprises an overhang segment which is at least 10 nucleotides complementary to, and forms a duplex with, a portion of the inverter oligonucleotide, wherein the inverter oligonucleotide is at least one nucleotide longer than the aptamer-inverter duplex and has more than 10 nucleotides complementary to a target nucleic acid; and (c) a signaling nanostructure that is reactive to active DNA polymerase enzyme, wherein the signaling nanostructure comprises a self-priming portion responsive to the DNA polymerase enzyme;

and optionally (d) labelled nucleotides (dNTPs) and signal development reagents, wherein active DNA polymerase enzyme adds labelled nucleotides to the signaling nanostructure and the signal development reagents bind to the labelled nucleotides incorporated into the self-primed portion.

27. The nucleic acid detection kit of claim 26, configured into a device according to claim 24.

28. The nucleic acid detection kit of claim 26, wherein at least one of the aptamer and/or inverter oligonucleotides is structurally and/or chemically modified from its natural nucleic acid.

29. The nucleic acid detection kit of claim 28, wherein said structural and/or chemical modification is selected from the group comprising the addition of tags, such as fluorescent tags, radioactive tags, biotin, a 5' tail, the addition of phosphorothioate (PS) bonds, 2'-O-Methyl modifications and/or phosphoramidite C3 Spacers during synthesis.

* * * * *

SEQUENCE LISTING

<160> NUMBER OF SEQ ID NOS: 153

<210> SEQ ID NO 1
<211> LENGTH: 35
<212> TYPE: DNA
<213> ORGANISM: Artificial Sequence
<220> FEATURE:
<223> OTHER INFORMATION: Recognition nanostructure characterization
      aptamer sequence

<400> SEQUENCE: 1
aagtatctgt aataaagtca caatgtacag tattg                          35

<210> SEQ ID NO 2
<211> LENGTH: 40
<212> TYPE: DNA
<213> ORGANISM: Artificial Sequence
<220> FEATURE:
<223> OTHER INFORMATION: Recognition nanostructure characterization inverter sequence

<400> SEQUENCE: 2
tgactttatt acagatactt ctacaacccc ggtaccatct                                  40

<210> SEQ ID NO 3
<211> LENGTH: 40
<212> TYPE: DNA
<213> ORGANISM: Artificial Sequence
<220> FEATURE:
<223> OTHER INFORMATION: Recognition nanostructure characterization
      complementary target

<400> SEQUENCE: 3
agatggtacc ggggttgtag aagtatctgt aataaagtca                                  40

<210> SEQ ID NO 4
<211> LENGTH: 40
<212> TYPE: DNA
<213> ORGANISM: Artificial Sequence
<220> FEATURE:
<223> OTHER INFORMATION: Recognition nanostructure characterization
      scrambled target

<400> SEQUENCE: 4
agtagaacgc gatggtacag gcactgcagg gtccatgtca                                  40

<210> SEQ ID NO 5
<211> LENGTH: 200
<212> TYPE: DNA
<213> ORGANISM: Artificial Sequence
<220> FEATURE:
<223> OTHER INFORMATION: Signalling nanostructure characterization self-
      priming template

<400> SEQUENCE: 5
agcaggcagt tacgggctgg tgcgatgaga gacgcggagt gtggcggccg gatagtaatg           60
actgcgaccg gtgtaccagt ggcgtgaggc aggtcgtgag gcggcgtacg tagagcgttg          120
agcaggatgc caacagtcga tcaggacgag tgctaacgca ttgtcgatag ctcagctgtc          180
tgagctatcg acaatgcgtt                                                      200

<210> SEQ ID NO 6
<211> LENGTH: 174
<212> TYPE: DNA
<213> ORGANISM: Artificial Sequence
<220> FEATURE:
<223> OTHER INFORMATION: Signalling nanostructure characterization
      linear template

<400> SEQUENCE: 6
agcaggcagt tacgggctgg tgcgatgaga gacgcggagt gtggcggccg gatagtaatg           60
actgcgaccg gtgtaccagt ggcgtgaggc aggtcgtgag gcggcgtacg tagagcgttg          120
agcaggatgc caacagtcga tcaggacgag tgctaacgca ttgtcgatag ctca                174

<210> SEQ ID NO 7
<211> LENGTH: 20
<212> TYPE: DNA
<213> ORGANISM: Artificial Sequence
<220> FEATURE:
<223> OTHER INFORMATION: Signalling nanostructure characterization
      linear template primer

<400> SEQUENCE: 7

```
tgagctatcg acaatgcgtt                                          20

<210> SEQ ID NO 8
<211> LENGTH: 20
<212> TYPE: DNA
<213> ORGANISM: Artificial Sequence
<220> FEATURE:
<223> OTHER INFORMATION: 10bp Taqman probe

<400> SEQUENCE: 8
ctgatcgact gttggcatcc                                          20

<210> SEQ ID NO 9
<211> LENGTH: 20
<212> TYPE: DNA
<213> ORGANISM: Artificial Sequence
<220> FEATURE:
<223> OTHER INFORMATION: 20bp Taqman probe

<400> SEQUENCE: 9
ttggcatcct gctcaacgct                                          20

<210> SEQ ID NO 10
<211> LENGTH: 20
<212> TYPE: DNA
<213> ORGANISM: Artificial Sequence
<220> FEATURE:
<223> OTHER INFORMATION: 30bp Taqman probe

<400> SEQUENCE: 10
tgctcaacgc tctacgtacg                                          20

<210> SEQ ID NO 11
<211> LENGTH: 20
<212> TYPE: DNA
<213> ORGANISM: Artificial Sequence
<220> FEATURE:
<223> OTHER INFORMATION: 50bp Taqman probe

<400> SEQUENCE: 11
gccgcctcac gacctgcctc                                          20

<210> SEQ ID NO 12
<211> LENGTH: 20
<212> TYPE: DNA
<213> ORGANISM: Artificial Sequence
<220> FEATURE:
<223> OTHER INFORMATION: 100bp Taqman probe

<400> SEQUENCE: 12
tatccggccg ccacactccg                                          20

<210> SEQ ID NO 13
<211> LENGTH: 20
<212> TYPE: DNA
<213> ORGANISM: Artificial Sequence
<220> FEATURE:
<223> OTHER INFORMATION: 130bp Taqman probe

<400> SEQUENCE: 13
cgcaccagcc cgtaactgcc                                          20

<210> SEQ ID NO 14
<211> LENGTH: 100
<212> TYPE: DNA
<213> ORGANISM: Artificial Sequence
```

<220> FEATURE:
<223> OTHER INFORMATION: 5' amine universal signalling nanostructure

<400> SEQUENCE: 14
gcggcgtacg tagagcgttg agcaggatgc caacagtcga tcaggacgag tgctaacgca      60
ttgtcgatag ctcagctgtc tgagctatcg acaatgcgtt                          100

<210> SEQ ID NO 15
<211> LENGTH: 40
<212> TYPE: DNA
<213> ORGANISM: Artificial Sequence
<220> FEATURE:
<223> OTHER INFORMATION: Complementary target overhang 2 mismatch

<400> SEQUENCE: 15
agatggtacc gcggttgtat aagtatctgt aataaagtca                           40

<210> SEQ ID NO 16
<211> LENGTH: 40
<212> TYPE: DNA
<213> ORGANISM: Artificial Sequence
<220> FEATURE:
<223> OTHER INFORMATION: Complementary target overhang 4 mismatch

<400> SEQUENCE: 16
agatagtgcc gcggttgtat aagtatctgt aataaagtca                           40

<210> SEQ ID NO 17
<211> LENGTH: 40
<212> TYPE: DNA
<213> ORGANISM: Artificial Sequence
<220> FEATURE:
<223> OTHER INFORMATION: Complementary target overhang 6 mismatch

<400> SEQUENCE: 17
agatagtgca gcggttatat aagtatctgt aataaagtca                           40

<210> SEQ ID NO 18
<211> LENGTH: 40
<212> TYPE: DNA
<213> ORGANISM: Artificial Sequence
<220> FEATURE:
<223> OTHER INFORMATION: Complementary target overhang 8 mismatch

<400> SEQUENCE: 18
acatagtgca gcggctatat aagtatctgt aataaagtca                           40

<210> SEQ ID NO 19
<211> LENGTH: 40
<212> TYPE: DNA
<213> ORGANISM: Artificial Sequence
<220> FEATURE:
<223> OTHER INFORMATION: Complementary target overhang 10 mismatch

<400> SEQUENCE: 19
acgtagtgca gcagctatat aagtatctgt aataaagtca                           40

<210> SEQ ID NO 20
<211> LENGTH: 40
<212> TYPE: DNA
<213> ORGANISM: Artificial Sequence
<220> FEATURE:
<223> OTHER INFORMATION: Complementary target overhang 12 mismatch

<400> SEQUENCE: 20
acgtagtgta gcagctatct aagtatctgt aataaagtca                            40

<210> SEQ ID NO 21
<211> LENGTH: 40
<212> TYPE: DNA
<213> ORGANISM: Artificial Sequence
<220> FEATURE:
<223> OTHER INFORMATION: Complementary target duplex 2 mismatch

<400> SEQUENCE: 21
agatggtacc ggggttgtag aattatctgt aatagagtca                            40

<210> SEQ ID NO 22
<211> LENGTH: 40
<212> TYPE: DNA
<213> ORGANISM: Artificial Sequence
<220> FEATURE:
<223> OTHER INFORMATION: Complementary target duplex 4 mismatch

<400> SEQUENCE: 22
agatggtacc ggggttgtag aattagctgt actagagtca                            40

<210> SEQ ID NO 23
<211> LENGTH: 40
<212> TYPE: DNA
<213> ORGANISM: Artificial Sequence
<220> FEATURE:
<223> OTHER INFORMATION: Complementary target duplex 6 mismatch

<400> SEQUENCE: 23
agatggtacc ggggttgtag tattagctct actagagtca                            40

<210> SEQ ID NO 24
<211> LENGTH: 40
<212> TYPE: DNA
<213> ORGANISM: Artificial Sequence
<220> FEATURE:
<223> OTHER INFORMATION: Complementary target duplex 8 mismatch

<400> SEQUENCE: 24
agatggtacc ggggttgtag tattcgctct actagagtaa                            40

<210> SEQ ID NO 25
<211> LENGTH: 40
<212> TYPE: DNA
<213> ORGANISM: Artificial Sequence
<220> FEATURE:
<223> OTHER INFORMATION: Complementary target duplex 10 mismatch

<400> SEQUENCE: 25
agatggtacc ggggttgtag tattcgctct acaagattaa                            40

<210> SEQ ID NO 26
<211> LENGTH: 40
<212> TYPE: DNA
<213> ORGANISM: Artificial Sequence
<220> FEATURE:
<223> OTHER INFORMATION: Complementary target duplex 12 mismatch

<400> SEQUENCE: 26
agatggtacc ggggttgtag tattcgcact acaagattac                            40

<210> SEQ ID NO 27
<211> LENGTH: 22
<212> TYPE: DNA
<213> ORGANISM: Artificial Sequence

```
<220> FEATURE:
<223> OTHER INFORMATION: HPV 16 forward primer

<400> SEQUENCE: 27
atggattata tgatatttat gc                                             22

<210> SEQ ID NO 28
<211> LENGTH: 18
<212> TYPE: DNA
<213> ORGANISM: Artificial Sequence
<220> FEATURE:
<223> OTHER INFORMATION: HPV 16 reverse primer

<400> SEQUENCE: 28
ctgataaaga tgtagagg                                                  18

<210> SEQ ID NO 29
<211> LENGTH: 87
<212> TYPE: DNA
<213> ORGANISM: Artificial Sequence
<220> FEATURE:
<223> OTHER INFORMATION: HPV 16 product

<400> SEQUENCE: 29
ctgataaaga tgtagagggt acagatggta ccggggttgt agaagtatct gtaataaagt    60
catctgcata aatatcatat aatccat                                        87

<210> SEQ ID NO 30
<211> LENGTH: 53
<212> TYPE: DNA
<213> ORGANISM: Artificial Sequence
<220> FEATURE:
<223> OTHER INFORMATION: HPV 16 NASBA forward primer

<400> SEQUENCE: 30
aattctaata cgactcacta tagggagaag ggcagcctca cctacttcta tta           53

<210> SEQ ID NO 31
<211> LENGTH: 20
<212> TYPE: DNA
<213> ORGANISM: Artificial Sequence
<220> FEATURE:
<223> OTHER INFORMATION: HPV 16 NASBA reverse primer

<400> SEQUENCE: 31
aaagatgtag agggtacaga                                                20

<210> SEQ ID NO 32
<211> LENGTH: 107
<212> TYPE: DNA
<213> ORGANISM: Artificial Sequence
<220> FEATURE:
<223> OTHER INFORMATION: HPV 16 NASBA product

<400> SEQUENCE: 32
gcagcctcac ctacttctat taataatgga ttatatgata tttatgcaga tgactttatt    60
acagatactt ctacaacccc ggtaccatct gtaccctcta catctttt                107

<210> SEQ ID NO 33
<211> LENGTH: 35
<212> TYPE: DNA
<213> ORGANISM: Artificial Sequence
<220> FEATURE:
<223> OTHER INFORMATION: Pan-HPV nanostructure 1 aptamer
```

<400> SEQUENCE: 33
tttaaataat ctggatattt caatgtacag tattg                                    35

<210> SEQ ID NO 34
<211> LENGTH: 30
<212> TYPE: DNA
<213> ORGANISM: Artificial Sequence
<220> FEATURE:
<223> OTHER INFORMATION: Pan-HPV nanostructure 1 inverter

<400> SEQUENCE: 34
aaatatccag attatttaaa aatggctgca                                          30

<210> SEQ ID NO 35
<211> LENGTH: 40
<212> TYPE: DNA
<213> ORGANISM: Artificial Sequence
<220> FEATURE:
<223> OTHER INFORMATION: Pan-HPV nanostructure 1 complementary positive
      target

<400> SEQUENCE: 35
cataaggatc tgcagccatt tttaaataat ctggatattt                               40

<210> SEQ ID NO 36
<211> LENGTH: 40
<212> TYPE: DNA
<213> ORGANISM: Artificial Sequence
<220> FEATURE:
<223> OTHER INFORMATION: Pan-HPV nanostructure 1 HPV 06 Target

<400> SEQUENCE: 36
catatgggtc tgcagccatt tgtaaataat ctggatattt                               40

<210> SEQ ID NO 37
<211> LENGTH: 40
<212> TYPE: DNA
<213> ORGANISM: Artificial Sequence
<220> FEATURE:
<223> OTHER INFORMATION: Pan-HPV nanostructure 1 HPV 16 Target

<400> SEQUENCE: 37
catatggttc tgacaccatt ttaatataat ctggatattt                               40

<210> SEQ ID NO 38
<211> LENGTH: 40
<212> TYPE: DNA
<213> ORGANISM: Artificial Sequence
<220> FEATURE:
<223> OTHER INFORMATION: Pan-HPV nanostructure 1 HPV 18 Target

<400> SEQUENCE: 38
cataaggatc tgcagacatt tgtaaataat caggatattt                               40

<210> SEQ ID NO 39
<211> LENGTH: 40
<212> TYPE: DNA
<213> ORGANISM: Artificial Sequence
<220> FEATURE:
<223> OTHER INFORMATION: Pan-HPV nanostructure 1 HPV 31 Target

<400> SEQUENCE: 39
catatggctc agcaaccatt ttaagataat ctggatattt                               40

<210> SEQ ID NO 40

<211> LENGTH: 40
<212> TYPE: DNA
<213> ORGANISM: Artificial Sequence
<220> FEATURE:
<223> OTHER INFORMATION: Pan-HPV nanostructure 1 HPV 33 Target

<400> SEQUENCE: 40
catatggctc agcaaccatt ttaagataat ctggatattt 40

<210> SEQ ID NO 41
<211> LENGTH: 40
<212> TYPE: DNA
<213> ORGANISM: Artificial Sequence
<220> FEATURE:
<223> OTHER INFORMATION: Pan-HPV nanostructure 1 HPV 58 Target

<400> SEQUENCE: 41
cataaggttc actggccatt tttaaataat ctggatattt 40

<210> SEQ ID NO 42
<211> LENGTH: 35
<212> TYPE: DNA
<213> ORGANISM: Artificial Sequence
<220> FEATURE:
<223> OTHER INFORMATION: Pan-HPV nanostructure 2 aptamer

<400> SEQUENCE: 42
aaataattgt gcctcagagg caatgtacag tattg 35

<210> SEQ ID NO 43
<211> LENGTH: 40
<212> TYPE: DNA
<213> ORGANISM: Artificial Sequence
<220> FEATURE:
<223> OTHER INFORMATION: Pan-HPV nanostructure 2 inverter

<400> SEQUENCE: 43
cctctgaggc acaattattt aataaaccat attggctaca 40

<210> SEQ ID NO 44
<211> LENGTH: 40
<212> TYPE: DNA
<213> ORGANISM: Artificial Sequence
<220> FEATURE:
<223> OTHER INFORMATION: Pan-HPV nanostructure 2 complementary positive
target

<400> SEQUENCE: 44
tgtagccaat atggtttatt aaataattgt gcctcagagg 40

<210> SEQ ID NO 45
<211> LENGTH: 40
<212> TYPE: DNA
<213> ORGANISM: Artificial Sequence
<220> FEATURE:
<223> OTHER INFORMATION: Pan-HPV nanostructure 2 HPV 06 Target

<400> SEQUENCE: 45
tgtagccaat atggcttatt aaacaattgt gcctcagagg 40

<210> SEQ ID NO 46
<211> LENGTH: 40
<212> TYPE: DNA
<213> ORGANISM: Artificial Sequence
<220> FEATURE:
<223> OTHER INFORMATION: Pan-HPV nanostructure 2 HPV 16 Target

<400> SEQUENCE: 46
tgtaaccaat aaggtttatt gaatatttgg gcatcagagg         40

<210> SEQ ID NO 47
<211> LENGTH: 40
<212> TYPE: DNA
<213> ORGANISM: Artificial Sequence
<220> FEATURE:
<223> OTHER INFORMATION: Pan-HPV nanostructure 2 HPV 18 Target

<400> SEQUENCE: 47
tgtaaccaat atggtttatt aaacaactgg gagtcagagg         40

<210> SEQ ID NO 48
<211> LENGTH: 40
<212> TYPE: DNA
<213> ORGANISM: Artificial Sequence
<220> FEATURE:
<223> OTHER INFORMATION: Pan-HPV nanostructure 2 HPV 31 Target

<400> SEQUENCE: 48
tgcatccaat atggtttatt aaaaatttgt gcatctgaag         40

<210> SEQ ID NO 49
<211> LENGTH: 40
<212> TYPE: DNA
<213> ORGANISM: Artificial Sequence
<220> FEATURE:
<223> OTHER INFORMATION: Pan-HPV nanostructure 2 HPV 33 Target

<400> SEQUENCE: 49
tgtagccaat atggcttatt aaataactga gattcggaag         40

<210> SEQ ID NO 50
<211> LENGTH: 40
<212> TYPE: DNA
<213> ORGANISM: Artificial Sequence
<220> FEATURE:
<223> OTHER INFORMATION: Pan-HPV nanostructure 2 HPV 58 Target

<400> SEQUENCE: 50
tgtagccaat aaggcttatt aaataattgt gattctgagg         40

<210> SEQ ID NO 51
<211> LENGTH: 35
<212> TYPE: DNA
<213> ORGANISM: Artificial Sequence
<220> FEATURE:
<223> OTHER INFORMATION: HPV 06 aptamer

<400> SEQUENCE: 51
taatgtcagg ttcaaaagat caatgtacag tattg         35

<210> SEQ ID NO 52
<211> LENGTH: 40
<212> TYPE: DNA
<213> ORGANISM: Artificial Sequence
<220> FEATURE:
<223> OTHER INFORMATION: HPV 06 inverter

<400> SEQUENCE: 52
atcttttgaa cctgacatta accctaccca acaccctgtt         40

<210> SEQ ID NO 53
<211> LENGTH: 40

```
<212> TYPE: DNA
<213> ORGANISM: Artificial Sequence
<220> FEATURE:
<223> OTHER INFORMATION: HPV 06 target

<400> SEQUENCE: 53
aacagggtgt tgggtagggt taatgtcagg ttcaaaagat         40

<210> SEQ ID NO 54
<211> LENGTH: 35
<212> TYPE: DNA
<213> ORGANISM: Artificial Sequence
<220> FEATURE:
<223> OTHER INFORMATION: HPV 11 aptamer

<400> SEQUENCE: 54
cagggatagg gtcaaatggt caatgtacag tattg              35

<210> SEQ ID NO 55
<211> LENGTH: 40
<212> TYPE: DNA
<213> ORGANISM: Artificial Sequence
<220> FEATURE:
<223> OTHER INFORMATION: HPV 11 inverter

<400> SEQUENCE: 55
accatttgac cctatccctg accctgtcca acattctgtt         40

<210> SEQ ID NO 56
<211> LENGTH: 40
<212> TYPE: DNA
<213> ORGANISM: Artificial Sequence
<220> FEATURE:
<223> OTHER INFORMATION: HPV 11 target

<400> SEQUENCE: 56
aacagaatgt tggacagggt cagggatagg gtcaaatggt         40

<210> SEQ ID NO 57
<211> LENGTH: 35
<212> TYPE: DNA
<213> ORGANISM: Artificial Sequence
<220> FEATURE:
<223> OTHER INFORMATION: HPV 16 aptamer

<400> SEQUENCE: 57
aagtatctgt aataaagtca caatgtacag tattg              35

<210> SEQ ID NO 58
<211> LENGTH: 40
<212> TYPE: DNA
<213> ORGANISM: Artificial Sequence
<220> FEATURE:
<223> OTHER INFORMATION: HPV 16 inverter

<400> SEQUENCE: 58
tgactttatt acagatactt ctacaacccc ggtaccatct         40

<210> SEQ ID NO 59
<211> LENGTH: 40
<212> TYPE: DNA
<213> ORGANISM: Artificial Sequence
<220> FEATURE:
<223> OTHER INFORMATION: HPV 16 target

<400> SEQUENCE: 59
```

```
agatggtacc ggggttgtag aagtatctgt aataaagtca                             40

<210> SEQ ID NO 60
<211> LENGTH: 35
<212> TYPE: DNA
<213> ORGANISM: Artificial Sequence
<220> FEATURE:
<223> OTHER INFORMATION: HPV 18 aptamer

<400> SEQUENCE: 60
gcactgcagg gtccatgtca caatgtacag tattg                                  35

<210> SEQ ID NO 61
<211> LENGTH: 40
<212> TYPE: DNA
<213> ORGANISM: Artificial Sequence
<220> FEATURE:
<223> OTHER INFORMATION: HPV 18 inverter

<400> SEQUENCE: 61
tgacatggac cctgcagtgc ctgtaccatc gcgttctact                             40

<210> SEQ ID NO 62
<211> LENGTH: 40
<212> TYPE: DNA
<213> ORGANISM: Artificial Sequence
<220> FEATURE:
<223> OTHER INFORMATION: HPV 18 target

<400> SEQUENCE: 62
agtagaacgc gatggtacag gcactgcagg gtccatgtca                             40

<210> SEQ ID NO 63
<211> LENGTH: 35
<212> TYPE: DNA
<213> ORGANISM: Artificial Sequence
<220> FEATURE:
<223> OTHER INFORMATION: HPV 31 aptamer

<400> SEQUENCE: 63
tatccacagt aaaatcagtg caatgtacag tattg                                  35

<210> SEQ ID NO 64
<211> LENGTH: 40
<212> TYPE: DNA
<213> ORGANISM: Artificial Sequence
<220> FEATURE:
<223> OTHER INFORMATION: HPV 31 inverter

<400> SEQUENCE: 64
cactgatttt actgtggata cacctgccac acataatgtt                             40

<210> SEQ ID NO 65
<211> LENGTH: 40
<212> TYPE: DNA
<213> ORGANISM: Artificial Sequence
<220> FEATURE:
<223> OTHER INFORMATION: HPV 31 target

<400> SEQUENCE: 65
aacattatgt gtggcaggtg tatccacagt aaaatcagtg                             40

<210> SEQ ID NO 66
<211> LENGTH: 35
<212> TYPE: DNA
<213> ORGANISM: Artificial Sequence
```

```
<220> FEATURE:
<223> OTHER INFORMATION: HPV 33 aptamer

<400> SEQUENCE: 66
tgtgtacatt atccacatcg caatgtacag tattg                              35

<210> SEQ ID NO 67
<211> LENGTH: 40
<212> TYPE: DNA
<213> ORGANISM: Artificial Sequence
<220> FEATURE:
<223> OTHER INFORMATION: HPV 33 inverter

<400> SEQUENCE: 67
cgatgtggat aatgtacaca ccccaatgca acactcatac                         40

<210> SEQ ID NO 68
<211> LENGTH: 40
<212> TYPE: DNA
<213> ORGANISM: Artificial Sequence
<220> FEATURE:
<223> OTHER INFORMATION: HPV 33 target

<400> SEQUENCE: 68
gtatgagtgt tgcattgggg tgtgtacatt atccacatcg                         40

<210> SEQ ID NO 69
<211> LENGTH: 35
<212> TYPE: DNA
<213> ORGANISM: Artificial Sequence
<220> FEATURE:
<223> OTHER INFORMATION: HPV 58 aptamer

<400> SEQUENCE: 69
catgtatagt atcagcatcg caatgtacag tattg                              35

<210> SEQ ID NO 70
<211> LENGTH: 40
<212> TYPE: DNA
<213> ORGANISM: Artificial Sequence
<220> FEATURE:
<223> OTHER INFORMATION: HPV 58 inverter

<400> SEQUENCE: 70
cgatgctgat actatacatg attttcagag tcctctgcac                         40

<210> SEQ ID NO 71
<211> LENGTH: 40
<212> TYPE: DNA
<213> ORGANISM: Artificial Sequence
<220> FEATURE:
<223> OTHER INFORMATION: HPV 58 target

<400> SEQUENCE: 71
gtgcagagga ctctgaaaat catgtatagt atcagcatcg                         40

<210> SEQ ID NO 72
<211> LENGTH: 35
<212> TYPE: DNA
<213> ORGANISM: Artificial Sequence
<220> FEATURE:
<223> OTHER INFORMATION: HPV 66 aptamer

<400> SEQUENCE: 72
tgggtgcctc atcatcaata caatgtacag tattg                              35
```

<210> SEQ ID NO 73
<211> LENGTH: 40
<212> TYPE: DNA
<213> ORGANISM: Artificial Sequence
<220> FEATURE:
<223> OTHER INFORMATION: HPV 66 inverter

<400> SEQUENCE: 73
tattgatgat gaggcaccca tttcatttcg tcagtctggt       40

<210> SEQ ID NO 74
<211> LENGTH: 40
<212> TYPE: DNA
<213> ORGANISM: Artificial Sequence
<220> FEATURE:
<223> OTHER INFORMATION: HPV 66 target

<400> SEQUENCE: 74
accagactga cgaaatgaaa tgggtgcctc atcatcaata       40

<210> SEQ ID NO 75
<211> LENGTH: 23
<212> TYPE: DNA
<213> ORGANISM: Artificial Sequence
<220> FEATURE:
<223> OTHER INFORMATION: HPV 06 forward primer

<400> SEQUENCE: 75
gaagatacat ttgatattta tgc       23

<210> SEQ ID NO 76
<211> LENGTH: 18
<212> TYPE: DNA
<213> ORGANISM: Artificial Sequence
<220> FEATURE:
<223> OTHER INFORMATION: HPV 06 reverse primer

<400> SEQUENCE: 76
attaggtgtg gaagttaa       18

<210> SEQ ID NO 77
<211> LENGTH: 91
<212> TYPE: DNA
<213> ORGANISM: Artificial Sequence
<220> FEATURE:
<223> OTHER INFORMATION: HPV 06 product

<400> SEQUENCE: 77
gaagatacat ttgatattta tgctgaatct tttgaacctg acattaaccc tacccaacac       60
cctgttacaa atatatcaga tacatattta a       91

<210> SEQ ID NO 78
<211> LENGTH: 19
<212> TYPE: DNA
<213> ORGANISM: Artificial Sequence
<220> FEATURE:
<223> OTHER INFORMATION: HPV 11 forward primer

<400> SEQUENCE: 78
acacgtttga tatttatgc       19

<210> SEQ ID NO 79
<211> LENGTH: 17
<212> TYPE: DNA
<213> ORGANISM: Artificial Sequence

```
<220> FEATURE:
<223> OTHER INFORMATION: HPV 11 reverse primer

<400> SEQUENCE: 79
tattaggtgt ggaggta                                                  17

<210> SEQ ID NO 80
<211> LENGTH: 93
<212> TYPE: DNA
<213> ORGANISM: Artificial Sequence
<220> FEATURE:
<223> OTHER INFORMATION: HPV 11 product

<400> SEQUENCE: 80
acacgtttga tatttatgct gaaccatttg accctatccc tgaccctgtc caacattctg   60
ttacacagtc ttatcttacc tccacaccta ata                                93

<210> SEQ ID NO 81
<211> LENGTH: 20
<212> TYPE: DNA
<213> ORGANISM: Artificial Sequence
<220> FEATURE:
<223> OTHER INFORMATION: HPV 18 forward primer

<400> SEQUENCE: 81
acttgtttga tatatatgca                                               20

<210> SEQ ID NO 82
<211> LENGTH: 19
<212> TYPE: DNA
<213> ORGANISM: Artificial Sequence
<220> FEATURE:
<223> OTHER INFORMATION: HPV 18 reverse primer

<400> SEQUENCE: 82
gcgaatattt aaaaaatgc                                                19

<210> SEQ ID NO 83
<211> LENGTH: 90
<212> TYPE: DNA
<213> ORGANISM: Artificial Sequence
<220> FEATURE:
<223> OTHER INFORMATION: HPV 18 product

<400> SEQUENCE: 83
acttgtttga tatatatgca gatgacatgg accctgcagt gcctgtacca tcgcgttcta   60
ctacctcctt tgcatttttt aaatattcgc                                    90

<210> SEQ ID NO 84
<211> LENGTH: 20
<212> TYPE: DNA
<213> ORGANISM: Artificial Sequence
<220> FEATURE:
<223> OTHER INFORMATION: HPV 31 forward primer

<400> SEQUENCE: 84
ggcttatatg acatttatgc                                               20

<210> SEQ ID NO 85
<211> LENGTH: 17
<212> TYPE: DNA
<213> ORGANISM: Artificial Sequence
<220> FEATURE:
<223> OTHER INFORMATION: HPV 31 reverse primer
```

<400> SEQUENCE: 85
actgtacagc agtagaa                                                    17

<210> SEQ ID NO 86
<211> LENGTH: 85
<212> TYPE: DNA
<213> ORGANISM: Artificial Sequence
<220> FEATURE:
<223> OTHER INFORMATION: HPV 31 product

<400> SEQUENCE: 86
ggcttatatg acatttatgc agacactgat tttactgtgg atacacctgc cacacataat      60
gtttcccctt ctactgctgt acagt                                           85

<210> SEQ ID NO 87
<211> LENGTH: 19
<212> TYPE: DNA
<213> ORGANISM: Artificial Sequence
<220> FEATURE:
<223> OTHER INFORMATION: HPV 33 forward primer

<400> SEQUENCE: 87
gtttgtatga tgtttatgc                                                  19

<210> SEQ ID NO 88
<211> LENGTH: 17
<212> TYPE: DNA
<213> ORGANISM: Artificial Sequence
<220> FEATURE:
<223> OTHER INFORMATION: HPV 33 reverse primer

<400> SEQUENCE: 88
ttgcaaacgt actgtat                                                    17

<210> SEQ ID NO 89
<211> LENGTH: 75
<212> TYPE: DNA
<213> ORGANISM: Artificial Sequence
<220> FEATURE:
<223> OTHER INFORMATION: HPV 33 product

<400> SEQUENCE: 89
gtttgtatga tgtttatgct gacgatgtgg ataatgtaca cccccaatg caacactcat       60 acagtacgtt tgcaa                                                      75

<210> SEQ ID NO 90
<211> LENGTH: 21
<212> TYPE: DNA
<213> ORGANISM: Artificial Sequence
<220> FEATURE:
<223> OTHER INFORMATION: HPV 58 forward primer

<400> SEQUENCE: 90
tggactttat gatatttatg c                                               21

<210> SEQ ID NO 91
<211> LENGTH: 15
<212> TYPE: DNA
<213> ORGANISM: Artificial Sequence
<220> FEATURE:
<223> OTHER INFORMATION: HPV 58 reverse primer

<400> SEQUENCE: 91
gcaaaggacg tatgt                                                      15

```
<210> SEQ ID NO 92
<211> LENGTH: 81
<212> TYPE: DNA
<213> ORGANISM: Artificial Sequence
<220> FEATURE:
<223> OTHER INFORMATION: HPV 58 product

<400> SEQUENCE: 92
tggactttat gatatttatg ctgacgatgc tgatactata catgattttc agagtcctct      60
gcactcacat acgtcctttg c                                                81

<210> SEQ ID NO 93
<211> LENGTH: 20
<212> TYPE: DNA
<213> ORGANISM: Artificial Sequence
<220> FEATURE:
<223> OTHER INFORMATION: HPV 66 forward primer

<400> SEQUENCE: 93
gcctatatga tatttatgca                                                  20

<210> SEQ ID NO 94
<211> LENGTH: 16
<212> TYPE: DNA
<213> ORGANISM: Artificial Sequence
<220> FEATURE:
<223> OTHER INFORMATION: HPV 66 reverse primer

<400> SEQUENCE: 94
aggtaattgt gcagaa                                                      16

<210> SEQ ID NO 95
<211> LENGTH: 86
<212> TYPE: DNA
<213> ORGANISM: Artificial Sequence
<220> FEATURE:
<223> OTHER INFORMATION: HPV 66 product

<400> SEQUENCE: 95
gcctatatga tatttatgca aatattgatg atgaggcacc catttcattt cgtcagtctg      60
gtgctacacc ttctgcacaa ttacct                                           86

<210> SEQ ID NO 96
<211> LENGTH: 60
<212> TYPE: DNA
<213> ORGANISM: Artificial Sequence
<220> FEATURE:
<223> OTHER INFORMATION: HPV 16 L2 template

<400> SEQUENCE: 96
tctaatacga ctcactatag agatggtacc ggggttgtag aagtatctgt aataaagtca      60

<210> SEQ ID NO 97
<211> LENGTH: 60
<212> TYPE: DNA
<213> ORGANISM: Artificial Sequence
<220> FEATURE:
<223> OTHER INFORMATION: HPV 16 L2 template complement

<400> SEQUENCE: 97
tgactttatt acagatactt ctacaacccc ggtaccatct ctatagtgag tcgtattaga      60

<210> SEQ ID NO 98
```

```
<211> LENGTH: 60
<212> TYPE: DNA
<213> ORGANISM: Artificial Sequence
<220> FEATURE:
<223> OTHER INFORMATION: HPV 18 L2 template

<400> SEQUENCE: 98
tctaatacga ctcactatag agtagaacgc gatggtacag gcactgcagg gtccatgtca      60

<210> SEQ ID NO 99
<211> LENGTH: 60
<212> TYPE: DNA
<213> ORGANISM: Artificial Sequence
<220> FEATURE:
<223> OTHER INFORMATION: HPV 18 L2 template complement

<400> SEQUENCE: 99
tgacatggac cctgcagtgc ctgtaccatc gcgttctact ctatagtgag tcgtattaga      60

<210> SEQ ID NO 100
<211> LENGTH: 35
<212> TYPE: DNA
<213> ORGANISM: Artificial Sequence
<220> FEATURE:
<223> OTHER INFORMATION: HPV 16 E1 aptamer

<400> SEQUENCE: 100
caaccacccc cacttccacc caatgtacag tattg                                 35

<210> SEQ ID NO 101
<211> LENGTH: 40
<212> TYPE: DNA
<213> ORGANISM: Artificial Sequence
<220> FEATURE:
<223> OTHER INFORMATION: HPV 16 E1 inverter

<400> SEQUENCE: 101
ggtggaagtg ggggtggttg cagtcagtac agtagtggaa                            40

<210> SEQ ID NO 102
<211> LENGTH: 40
<212> TYPE: DNA
<213> ORGANISM: Artificial Sequence
<220> FEATURE:
<223> OTHER INFORMATION: HPV 16 E1 target

<400> SEQUENCE: 102
ttccactact gtactgactg caaccacccc cacttccacc                            40

<210> SEQ ID NO 103
<211> LENGTH: 35
<212> TYPE: DNA
<213> ORGANISM: Artificial Sequence
<220> FEATURE:
<223> OTHER INFORMATION: L1 aptamer

<400> SEQUENCE: 103
gtttctgaag tagatatggc caatgtacag tattg                                 35

<210> SEQ ID NO 104
<211> LENGTH: 40
<212> TYPE: DNA
<213> ORGANISM: Artificial Sequence
<220> FEATURE:
<223> OTHER INFORMATION: HPV 16 L1 inverter

<400> SEQUENCE: 104
```
gccatatcta cttcagaaac tacatataaa aatactaact                          40

<210> SEQ ID NO 105
<211> LENGTH: 40
<212> TYPE: DNA
<213> ORGANISM: Artificial Sequence
<220> FEATURE:
<223> OTHER INFORMATION: HPV 16 L1 target

<400> SEQUENCE: 105
agttagtatt tttatatgta gtttctgaag tagatatggc                          40

<210> SEQ ID NO 106
<211> LENGTH: 35
<212> TYPE: DNA
<213> ORGANISM: Artificial Sequence
<220> FEATURE:
<223> OTHER INFORMATION: HPV 16 L2 aptamer

<400> SEQUENCE: 106
aagtatctgt aataaagtca caatgtacag tattg                               35

<210> SEQ ID NO 107
<211> LENGTH: 40
<212> TYPE: DNA
<213> ORGANISM: Artificial Sequence
<220> FEATURE:
<223> OTHER INFORMATION: L2 inverter

<400> SEQUENCE: 107
tgactttatt acagatactt ctacaacccc ggtaccatct                          40

<210> SEQ ID NO 108
<211> LENGTH: 40
<212> TYPE: DNA
<213> ORGANISM: Artificial Sequence
<220> FEATURE:
<223> OTHER INFORMATION: HPV 16 L2 target

<400> SEQUENCE: 108
agatggtacc ggggttgtag aagtatctgt aataaagtca                          40

<210> SEQ ID NO 109
<211> LENGTH: 35
<212> TYPE: DNA
<213> ORGANISM: Artificial Sequence
<220> FEATURE:
<223> OTHER INFORMATION: HPV 18 E1 aptamer

<400> SEQUENCE: 109 tgtgccccg ttgtctatag caatgtacag tattg                                35

<210> SEQ ID NO 110
<211> LENGTH: 40
<212> TYPE: DNA
<213> ORGANISM: Artificial Sequence
<220> FEATURE:
<223> OTHER INFORMATION: HPV 18 E1 inverter

<400> SEQUENCE: 110
ctatagacaa cggggcaca gagggcaaca acagcagtgt                           40

<210> SEQ ID NO 111
<211> LENGTH: 40
<212> TYPE: DNA

```
<213> ORGANISM: Artificial Sequence
<220> FEATURE:
<223> OTHER INFORMATION: HPV 18 E1 target

<400> SEQUENCE: 111
acactgctgt tgttgccctc tgtgcccccg ttgtctatag                              40

<210> SEQ ID NO 112
<211> LENGTH: 35
<212> TYPE: DNA
<213> ORGANISM: Artificial Sequence
<220> FEATURE:
<223> OTHER INFORMATION: HPV 18 L1 aptamer

<400> SEQUENCE: 112
aggtacagga gactgtgtag caatgtacag tattg                                  35

<210> SEQ ID NO 113
<211> LENGTH: 40
<212> TYPE: DNA
<213> ORGANISM: Artificial Sequence
<220> FEATURE:
<223> OTHER INFORMATION: HPV 18 L1 inverter

<400> SEQUENCE: 113
ctacacagtc tcctgtacct gggcaatatg atgctaccaa                              40

<210> SEQ ID NO 114
<211> LENGTH: 40
<212> TYPE: DNA
<213> ORGANISM: Artificial Sequence
<220> FEATURE:
<223> OTHER INFORMATION: HPV 18 L1 target

<400> SEQUENCE: 114
ttggtagcat catattgccc aggtacagga gactgtgtag                              40

<210> SEQ ID NO 115
<211> LENGTH: 35
<212> TYPE: DNA
<213> ORGANISM: Artificial Sequence
<220> FEATURE:
<223> OTHER INFORMATION: HPV 18 L2 aptamer

<400> SEQUENCE: 115
gcactgcagg gtccatgtca caatgtacag tattg                                  35

<210> SEQ ID NO 116
<211> LENGTH: 40
<212> TYPE: DNA
<213> ORGANISM: Artificial Sequence
<220> FEATURE:
<223> OTHER INFORMATION: HPV 18 L2 inverter

<400> SEQUENCE: 116
tgacatggac cctgcagtgc ctgtaccatc gcgttctact                              40

<210> SEQ ID NO 117
<211> LENGTH: 40
<212> TYPE: DNA
<213> ORGANISM: Artificial Sequence
<220> FEATURE:
<223> OTHER INFORMATION: HPV 18 L2 target

<400> SEQUENCE: 117
agtagaacgc gatggtacag gcactgcagg gtccatgtca                              40
```

<210> SEQ ID NO 118
<211> LENGTH: 20
<212> TYPE: DNA
<213> ORGANISM: Artificial Sequence
<220> FEATURE:
<223> OTHER INFORMATION: HPV 16 E1 forward primer

<400> SEQUENCE: 118
caacgtgttg cgattggtgt                                         20

<210> SEQ ID NO 119
<211> LENGTH: 22
<212> TYPE: DNA
<213> ORGANISM: Artificial Sequence
<220> FEATURE:
<223> OTHER INFORMATION: HPV 16 E1 reverse primer

<400> SEQUENCE: 119
accattcccc atgaacatgc ta                                      22

<210> SEQ ID NO 120
<211> LENGTH: 20
<212> TYPE: DNA
<213> ORGANISM: Artificial Sequence
<220> FEATURE:
<223> OTHER INFORMATION: HPV 16 E1 Taqman probe

<400> SEQUENCE: 120
acacccagta tagctgacag                                         20

<210> SEQ ID NO 121
<211> LENGTH: 20
<212> TYPE: DNA
<213> ORGANISM: Artificial Sequence
<220> FEATURE:
<223> OTHER INFORMATION: HPV L1 forward primer

<400> SEQUENCE: 121
cacctaatgg ctgaccacga                                         20

<210> SEQ ID NO 122
<211> LENGTH: 20
<212> TYPE: DNA
<213> ORGANISM: Artificial Sequence
<220> FEATURE:
<223> OTHER INFORMATION: HPV 16 L1 reverse primer

<400> SEQUENCE: 122
acttgcagtt ggacatccct                                         20

<210> SEQ ID NO 123
<211> LENGTH: 20
<212> TYPE: DNA
<213> ORGANISM: Artificial Sequence
<220> FEATURE:
<223> OTHER INFORMATION: HPV 16 L1 Taqman probe

<400> SEQUENCE: 123
cacctacaca ggcccaaacc                                         20

<210> SEQ ID NO 124
<211> LENGTH: 20
<212> TYPE: DNA
<213> ORGANISM: Artificial Sequence
<220> FEATURE:

<223> OTHER INFORMATION: HPV 16 L2 forward primer

<400> SEQUENCE: 124
ttggaacagg gtcgggtaca                                              20

<210> SEQ ID NO 125
<211> LENGTH: 20
<212> TYPE: DNA
<213> ORGANISM: Artificial Sequence
<220> FEATURE:
<223> OTHER INFORMATION: HPV 16 L2 reverse primer

<400> SEQUENCE: 125
gaagggccca caggatctac                                              20

<210> SEQ ID NO 126
<211> LENGTH: 20
<212> TYPE: DNA
<213> ORGANISM: Artificial Sequence
<220> FEATURE:
<223> OTHER INFORMATION: HPV 16 L2 Taqman probe

<400> SEQUENCE: 126
tgggaacaag gcctcccaca                                              20

<210> SEQ ID NO 127
<211> LENGTH: 35
<212> TYPE: DNA
<213> ORGANISM: Artificial Sequence
<220> FEATURE:
<223> OTHER INFORMATION: HPV 16 NOT aptamer

<400> SEQUENCE: 127
tgactttatt acagatactt caatgtacag tattg                             35

<210> SEQ ID NO 128
<211> LENGTH: 35
<212> TYPE: DNA
<213> ORGANISM: Artificial Sequence
<220> FEATURE:
<223> OTHER INFORMATION: HPV 18 NOT aptamer

<400> SEQUENCE: 128
tgacatggac cctgcagtgc caatgtacag tattg                             35

<210> SEQ ID NO 129
<211> LENGTH: 38
<212> TYPE: DNA
<213> ORGANISM: Artificial Sequence
<220> FEATURE:
<223> OTHER INFORMATION: HPV 16 E1 LAMP Forward Internal Primer

<400> SEQUENCE: 129
tggcgccctt ctacctgtaa acagcgggta tggcaata                          38

<210> SEQ ID NO 130
<211> LENGTH: 43
<212> TYPE: DNA
<213> ORGANISM: Artificial Sequence
<220> FEATURE:
<223> OTHER INFORMATION: HPV 16 E1 LAMP Back Internal Primer

<400> SEQUENCE: 130
caccatgtag tcagtatagt ggtgtttcac taacaccctc tcc                    43

```
<210> SEQ ID NO 131
<211> LENGTH: 18
<212> TYPE: DNA
<213> ORGANISM: Artificial Sequence
<220> FEATURE:
<223> OTHER INFORMATION: HPV 16 E1 LAMP Forward Primer 3

<400> SEQUENCE: 131
agagctgcaa aaaggaga                                                18

<210> SEQ ID NO 132
<211> LENGTH: 21
<212> TYPE: DNA
<213> ORGANISM: Artificial Sequence
<220> FEATURE:
<223> OTHER INFORMATION: HPV 16 E1 LAMP Back Primer 3

<400> SEQUENCE: 132
gtgtttggca tatagtgtgt c                                            21

<210> SEQ ID NO 133
<211> LENGTH: 48
<212> TYPE: DNA
<213> ORGANISM: Artificial Sequence
<220> FEATURE:
<223> OTHER INFORMATION: HPV 16 L1 LAMP Forward Internal Primer

<400> SEQUENCE: 133
tggcagcaca taatgacata tttgtggtaa ccaactattt gttactgt               48

<210> SEQ ID NO 134
<211> LENGTH: 47
<212> TYPE: DNA
<213> ORGANISM: Artificial Sequence
<220> FEATURE:
<223> OTHER INFORMATION: HPV 16 L1 LAMP Back Internal Primer

<400> SEQUENCE: 134
aactttaagg agtacctacg acatgagtta aggttatttt gcacagt                47

<210> SEQ ID NO 135
<211> LENGTH: 21
<212> TYPE: DNA
<213> ORGANISM: Artificial Sequence
<220> FEATURE:
<223> OTHER INFORMATION: HPV 16 L1 LAMP Forward Primer 3

<400> SEQUENCE: 135
ccacaataat ggcatttgtt g                                            21

<210> SEQ ID NO 136
<211> LENGTH: 23
<212> TYPE: DNA
<213> ORGANISM: Artificial Sequence
<220> FEATURE:
<223> OTHER INFORMATION: HPV 16 L1 LAMP Back Primer 3

<400> SEQUENCE: 136
atgtatgtat gtcataacgt ctg                                          23

<210> SEQ ID NO 137
<211> LENGTH: 50
<212> TYPE: DNA
<213> ORGANISM: Artificial Sequence
<220> FEATURE:
<223> OTHER INFORMATION: HPV 16 L2 LAMP Forward Internal Primer
```

<400> SEQUENCE: 137
ccggggttgt agaagtatct gtaatctcac ctacttctat taataatgga                    50

<210> SEQ ID NO 138
<211> LENGTH: 46
<212> TYPE: DNA
<213> ORGANISM: Artificial Sequence
<220> FEATURE:
<223> OTHER INFORMATION: HPV 16 L2 LAMP Back Internal Primer

<400> SEQUENCE: 138
taccatctgt accctctaca tctttggaat attgtatgca ccacca                        46

<210> SEQ ID NO 139
<211> LENGTH: 22
<212> TYPE: DNA
<213> ORGANISM: Artificial Sequence
<220> FEATURE:
<223> OTHER INFORMATION: HPV 16 L2 LAMP Forward Primer 3

<400> SEQUENCE: 139
catatactac cacttcacat gc                                                  22

<210> SEQ ID NO 140
<211> LENGTH: 20
<212> TYPE: DNA
<213> ORGANISM: Artificial Sequence
<220> FEATURE:
<223> OTHER INFORMATION: HPV 16 L2 LAMP Back Primer 3

<400> SEQUENCE: 140
aatgggtata tcaggacctg                                                     20

<210> SEQ ID NO 141
<211> LENGTH: 44
<212> TYPE: DNA
<213> ORGANISM: Artificial Sequence
<220> FEATURE:
<223> OTHER INFORMATION: HPV 18 E1 LAMP Forward Internal Primer

<400> SEQUENCE: 141
tgaatctgtg ttgcttccac ttcgcggctg tttacaatat caga                          44

<210> SEQ ID NO 142
<211> LENGTH: 42
<212> TYPE: DNA
<213> ORGANISM: Artificial Sequence
<220> FEATURE:
<223> OTHER INFORMATION: HPV 18 E1 LAMP Back Internal Primer

<400> SEQUENCE: 142
aacatggcgg caatgtatgt agtgtctaca ctgctgttgt tg                            42

<210> SEQ ID NO 143
<211> LENGTH: 18
<212> TYPE: DNA
<213> ORGANISM: Artificial Sequence
<220> FEATURE:
<223> OTHER INFORMATION: HPV 18 E1 LAMP Forward Primer 3

<400> SEQUENCE: 143
tagtgggcag aaaaaggc                                                       18

<210> SEQ ID NO 144
<211> LENGTH: 21

```
<212> TYPE: DNA
<213> ORGANISM: Artificial Sequence
<220> FEATURE:
<223> OTHER INFORMATION: HPV 18 E1 LAMP Back Primer 3

<400> SEQUENCE: 144
attgctattg tcacttgtac c                                              21

<210> SEQ ID NO 145
<211> LENGTH: 43
<212> TYPE: DNA
<213> ORGANISM: Artificial Sequence
<220> FEATURE:
<223> OTHER INFORMATION: HPV 18 L1 LAMP Forward Internal Primer

<400> SEQUENCE: 145
aatcatattc ctcaacatgt ctgctctcct gtacctgggc aat                      43

<210> SEQ ID NO 146
<211> LENGTH: 45
<212> TYPE: DNA
<213> ORGANISM: Artificial Sequence
<220> FEATURE:
<223> OTHER INFORMATION: HPV 18 L1 LAMP Back Internal Primer

<400> SEQUENCE: 146
actttaactg cagatgttat gtcctaccaa agttccaatc ctcta                    45

<210> SEQ ID NO 147
<211> LENGTH: 21
<212> TYPE: DNA
<213> ORGANISM: Artificial Sequence
<220> FEATURE:
<223> OTHER INFORMATION: HPV 18 L1 LAMP Forward Primer 3

<400> SEQUENCE: 147
caatatgtgc ttctacacag t                                              21

<210> SEQ ID NO 148
<211> LENGTH: 20
<212> TYPE: DNA
<213> ORGANISM: Artificial Sequence
<220> FEATURE:
<223> OTHER INFORMATION: HPV 18 L1 LAMP Back Primer 3

<400> SEQUENCE: 148
tccaccaaac tagtagttgg                                                20

<210> SEQ ID NO 149
<211> LENGTH: 47
<212> TYPE: DNA
<213> ORGANISM: Artificial Sequence
<220> FEATURE:
<223> OTHER INFORMATION: HPV 18 L2 LAMP Forward Internal Primer

<400> SEQUENCE: 149
aaggaggtag tagaacgcga tgcttgtttg atatatatgc agatgac                  47

<210> SEQ ID NO 150
<211> LENGTH: 43
<212> TYPE: DNA
<213> ORGANISM: Artificial Sequence
<220> FEATURE:
<223> OTHER INFORMATION: HPV 18 L2 LAMP Back Internal Primer

<400> SEQUENCE: 150
```

```
tgcatttttt aaatattcgc ccactggagg ttaaagggac cgt                    43

<210> SEQ ID NO 151
<211> LENGTH: 19
<212> TYPE: DNA
<213> ORGANISM: Artificial Sequence
<220> FEATURE:
<223> OTHER INFORMATION: HPV 18 L2 LAMP Forward Primer 3

<400> SEQUENCE: 151
ctttagtatc tgccacgga                                               19

<210> SEQ ID NO 152
<211> LENGTH: 18
<212> TYPE: DNA
<213> ORGANISM: Artificial Sequence
<220> FEATURE:
<223> OTHER INFORMATION: HPV 18 L2 LAMP Back Primer 3

<400> SEQUENCE: 152
tacaggcaca tcccaaga                                                18

<210> SEQ ID NO 153
<211> LENGTH: 15
<212> TYPE: DNA
<213> ORGANISM: Artificial Sequence
<220> FEATURE:
<223> OTHER INFORMATION: DNA aptamer conserved sequence

<400> SEQUENCE: 153
caatgtacag tattg                                                   15
```